(12) United States Patent
Duchateau et al.

(10) Patent No.: US 10,087,453 B2
(45) Date of Patent: Oct. 2, 2018

(54) MODIFIED DIATOMS FOR BIOFUEL PRODUCTION

(71) Applicant: CELLECTIS, Paris (FR)

(72) Inventors: Philippe Duchateau, Paris (FR); Fayza Daboussi, Chelles (FR); David Sourdive, Levallois-Perret (FR); Jean-Charles Epinat, Les Lilas (FR)

(73) Assignee: CELLECTIS, Paris (FR)

( * ) Notice: Subject to any disclaimer, the term of this patent is extended or adjusted under 35 U.S.C. 154(b) by 332 days.

(21) Appl. No.: 14/899,107

(22) PCT Filed: Jun. 25, 2014

(86) PCT No.: PCT/EP2014/063393
§ 371 (c)(1),
(2) Date: Dec. 16, 2015

(87) PCT Pub. No.: WO2014/207043
PCT Pub. Date: Dec. 31, 2014

(65) Prior Publication Data
US 2016/0130599 A1 May 12, 2016

(30) Foreign Application Priority Data
Jun. 25, 2013 (DK) .................. 2013 70354

(51) Int. Cl.
| | | |
|---|---|---|
| *C12N 15/82* | (2006.01) | |
| *C12P 7/64* | (2006.01) | |
| *C12N 9/16* | (2006.01) | |
| *C12N 9/12* | (2006.01) | |
| *C12N 9/10* | (2006.01) | |
| *C12N 9/02* | (2006.01) | |
| *C12N 9/04* | (2006.01) | |
| *C12N 15/79* | (2006.01) | |

(52) U.S. Cl.
CPC ......... *C12N 15/8247* (2013.01); *C12N 9/001* (2013.01); *C12N 9/0006* (2013.01); *C12N 9/0071* (2013.01); *C12N 9/1029* (2013.01); *C12N 9/1241* (2013.01); *C12N 9/16* (2013.01); *C12N 15/79* (2013.01); *C12P 7/64* (2013.01); *C12P 7/6427* (2013.01); *C12Y 101/01008* (2013.01); *C12Y 103/01009* (2013.01); *C12Y 114/19006* (2013.01); *C12Y 203/01* (2013.01); *C12Y 207/07009* (2013.01); *C12Y 301/02022* (2013.01)

(58) Field of Classification Search
None
See application file for complete search history.

(56) References Cited

U.S. PATENT DOCUMENTS 8,846,370 B2 * 9/2014 Brown .................. C12N 9/16
435/252.3

FOREIGN PATENT DOCUMENTS

| WO | 2012/082731 A2 | 6/2012 |
| WO | 2013/034648 A1 | 3/2013 |
| WO | 2014/076571 A2 | 5/2014 |

OTHER PUBLICATIONS

Rayza Daboussi et al., "Genome Engineering Empowers the Diatom Phaeodactylum tricornutum for Biotechnology," Nature Communications, vol. 5, 4831 (2014).
Randor Radakovits, et al., "Genetic Engineering of Fatty Acid Chain Length in Phaeodactylum tricornutum," Metabolic Engineering, vol. 13, pp. 89-95 (2011).
Randor Radakovits, et al., "Genetic Engineering of Algae for Enhanced Biofuel Production," Eukaryotic Cell, vol. 9, No. 4, pp. 486-501 (2010).

* cited by examiner

*Primary Examiner* — Suzanne M Noakes
*Assistant Examiner* — Jae W Lee
(74) *Attorney, Agent, or Firm* — Arrigo, Lee, Guttmann & Mouta-Bellum LLP

(57) ABSTRACT

The invention provides engineered diatoms and methods of producing oil using diatoms. The invention also provides methods of modifying the lipids quantity and/or quality produced by diatom organisms through genome engineering. Also provided are oils, fuels, oleochemicals, chemical precursors, and other compounds manufactured from such modified diatoms.

20 Claims, 24 Drawing Sheets
Specification includes a Sequence Listing.

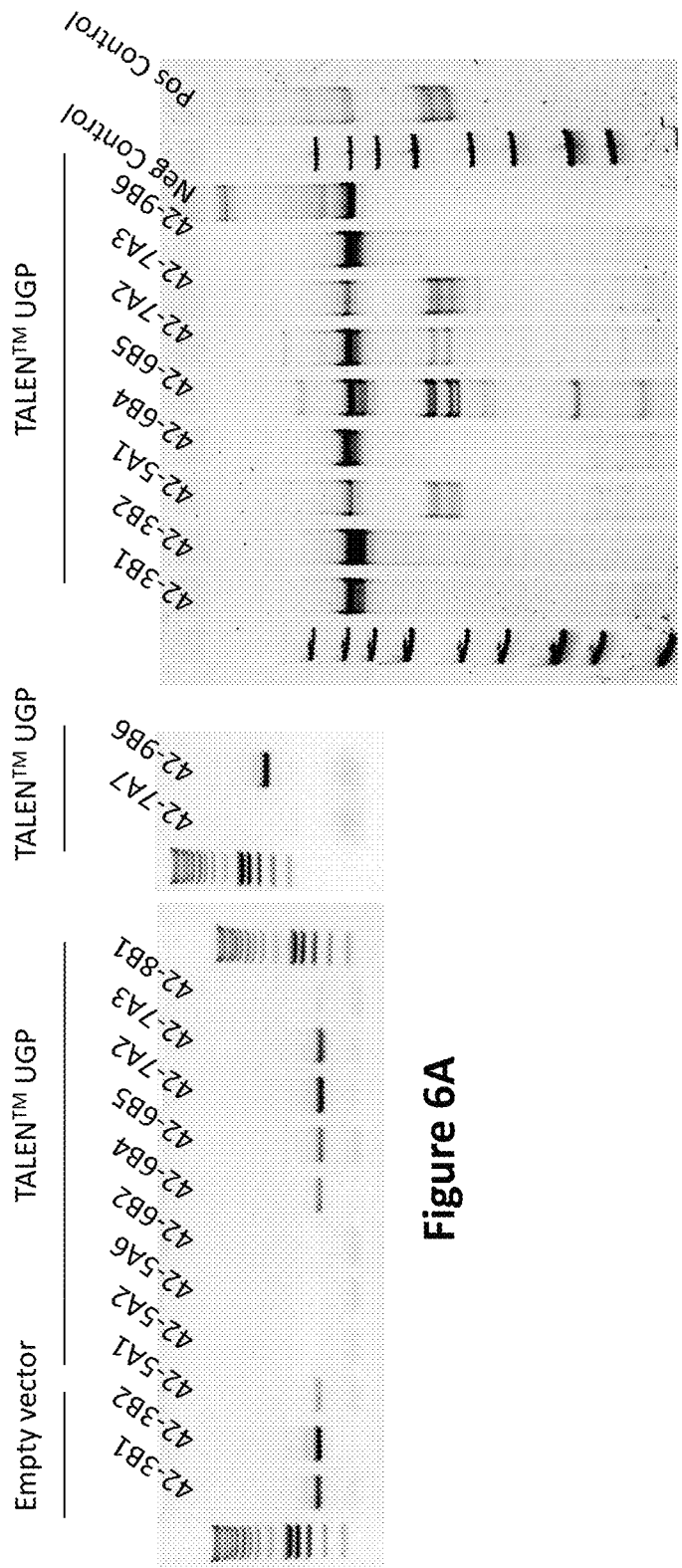

```
Query:    1   ctgtgcgtcggttgaatcggctaactcgctgcgtttcgatgacgacgagccagtc   60
              ||||||||||||||||||||||||||||||||||||||||||||||||||||||||
Target:   1   ctgtgcgtcggttgaatcggctaactcgcgtttcgatgacgacgagccagtc     60

Query:    61  tacttattctttgtgctactgtaggatctctctgcatgttctctcactgtgaatttgcgt  120
              ||||||||||||||||||||||||||||||||||||||||||||||||||||||||||||
Target:   61  tacttattctttgtgctactgtaggatctctctgcatgttctctcactgtgaatttgcgt  120

Query:    121 tcctttcaggc-aaaatgaagccggaggctgtgctcccatcgctattg------------  167
              |||||||||||  ||||||||||||||||||||||||||||||||||
Target:   121 tcctttcaggcaaaaatgaaggcgaggctgtgctccatcggcgattgccgccttcgagt  180

Query:    168 -----------------cgggtgattccggtgattccggtgattccggaatgatttggaagactctattgcgc  206
                               |||||||||||||||||||||||||||||||||||||||||||||
Target:   181 cgacctatggtagtctcgcctcgggtgattccggaatgatttggaagactctattgcgc  240

Query:    207 ccgt-ccccagctggacaagaccgcggagctggatattgcaccaacgccaccctcttg   265
              |||| ||||||||||||||||||||||||||||||||||||||||||||||||||||||
Target:   241 ccgtcccccagctggacaagaccgcggagctggatattgcaccaacgccaccctcttg   300

Query:    266 ccgagacggtagttctcaaactcaatggtggactggtggcacgggtatggtcgtggacaag  325
              ||||||||||||||||||||||||||||||||||||||||||||||||||||||||||||
Target:   301 ccgagacggtagttctcaaactcaatggtggactggtggcacgggtatgggtc--tggacaag  359

Query:    326 gccgaagtccctcgttgccagtcaaggggacgacacctttttgtattgtaccgcc-aa  384
              |||||||||||||||||||||||||||||||||||| |||||||| ||| ||||||| ||
Target:   360 gcc-aagtccct-gttgccagtcaaggggac-gacacctttttgatttgaccgccaaa  416

Query:    385 caagt  389
              |||||
Target:   417 caagt  421
```

Figure 7

```
Time (ms):   14
Length:      421
Score:       1907.0
Query:       H3Q3I4A01CHNFM, Length: 398
Target:      Pcr_Delta_6_Elongase_Deep,    Length: 420

Query:    1 tatcactcagaagcgcatccgttggttcccattgcgcctactctacggactcttg  60
            |||||||||||||||||||||||||||||||||||||||||||||||||||||||
Target:   1 tatcactcagaagcgcatccgttggttcccattgcgcctactctacggactcttg  60

Query:   61 atggtggcgggacaggcctactttcgcacacgcgaaccactccgggcgcggacctccctc 120
            ||||||||||||||||||||||||||||||||||||||||||||||||||||||||||||
Target:  61 atggtggcgggacaggcctactttcgcacacgcgaaccactccgggcgcggacctccctc 120

Query:  121 gcggcctggaatctcttctgccctctttccctcgtcg------------------------ 160
            ||||||||||||||||||||||||||||||||||||
Target: 121 gcggcctggaatctcttctgccctctttccctcgtcgcaatgctccggacctttccc 180

Query:  161 --gcttgtacacaacctcgcgacgctcacgtccggg-aaatctctgcgccaatccgcaa 217
              |||||||||||||||||||||||||||||||||| ||||||||||||||||||||||
Target: 181 cagcttgtacacaacctcgcgacgctcacgtccgggaaaatctctgcgccaatccgcaa 240

Query:  218 gccacctacggatccggatccaccggattgtgggtacaactctctttattctgtccaattt 277
            |||||||||||||||||||||||||||||||||||||||||||||||||||||||||| |
Target: 241 gccacctacggatccggatccaccggattgtgggtacaactcttttattctgtccaaa-tt 299

Query:  278 cccgtacgttcttttttgcagacatgtgtgggcggtggactcacatatatacata 337
            |||||||||||||||||||||||||||||||||||||||||||||||||||||||
Target: 300 cccgtacgttcttttttgcagacatgtgtggggcggtggactcacatatatacata 359

Query:  338 cacacacacagatactgacacttgctgccttatacccttccagtgaactcattg 397
            |||||||||||||||||||||||||||||||||||||||||||||||||||||
Target: 360 cacacacacagatactgacacttgctgccttatacccttccagtgaactcattg 419
```

MODIFIED DIATOMS FOR BIOFUEL PRODUCTION

SEQUENCE LISTING

The instant application contains a Sequence Listing which has been submitted in ASCII format via EFS-Web and is hereby incorporated by reference in its entirety. Said ASCII copy, created on Jun. 22, 2018, is named Revised_ST25.txt and is 152,137 bytes in size.

FIELD OF THE INVENTION

The invention provides engineered diatoms and methods of producing oil using diatoms. The invention also provides methods of modifying the lipids quantity and/or quality produced by diatom organisms through genome engineering. Also provided are oils, fuels, oleochemicals, chemical precursors, and other compounds manufactured from such modified diatoms.

BACKGROUND OF THE INVENTION

Concerns about rises in prices of fossil fuels have prompted intense interest in the development of engineered microorganisms as attractive sources for the production of biofuel. Photosynthetic algae have been of considerable interest as a possible biofuel resource for decades. Diatoms are one of the most ecologically successful unicellular phytoplankton on the planet, being responsible for approximately 20% of global carbon fixation, representing a major participant in the marine food web. They are able to accumulate abundant amounts of lipid suitable for conversion to liquid fuels and because of their high potential to produce large quantities and varieties of lipids and good growth efficiencies, they are considered as one of the best classes of algae for renewable biofuel production (Kroth 2007; Saade and Bowler 2009).

Nevertheless, relatively little is known about lipid metabolism in these algae. Extensive knowledge on complex lipid metabolism pathways is gained mostly from studies of plant or animal models. Genetic engineering of diatoms lipid gene is indispensable to understand the complex lipid metabolism and improve lipid production. However, despite the recent publication of *Thalassiosira pseudonana* (Armbrust, Berges et al. 2004) and *Phaeodactylum tricornutum* genomes (Bowler, Allen et al. 2008), very few genetic tools to explore diatoms genetics are available at this time: annotations of the diatoms genomes remain essentially based on putative open reading frames without confirmation of actual gene function. For instance, the direct manipulation of target genes by homologous recombination has proven difficult and the generation of loss of function mutants by insertional or chemical mutagenesis is challenging in diatoms because they are diploid organisms. This considerably limits the use of these organisms for biofuel applications. One genetic engineering study has succeeded to increase the amount of lipid within diatom. However, this was made by random integration of two transgenes involved in lipid metabolism (Radakovits, Eduafo et al. 2011).

SUMMARY OF THE INVENTION

Based on genome comparison and protein homology search, the inventors selected several target genes involved in lipid metabolism and, for the first time, selectively inactivated them in order to create new diatom strains for biofuel production. Generation of modified diatoms was facilitated by using specific rare-cutting endonuclease, in particular TAL-nucleases, MBBBD-nucleases and/or CRISPR/Cas9-nucleases, allowing specific gene targeting within the diatom genome. The inventors thereby generated diatoms in which inactivation of the selected genes induces an increase quantity and/or quality of lipid content.

BRIEF DESCRIPTION OF FIGURES

FIG. 6A-B: Molecular characterization of clones from the transformation of the *Phaeodactylum tricornutum* (Pt) strain with the TALE-Nuclease targeting the UGPase gene (experiment 2). (FIG. 6A) Amplification of the UGPase locus by PCR surrounding the TALE-Nuclease cleavage site and migration of the PCR products on an agarose gel. On the 11 clones tested, five were not amplified by PCR (42-5A2, 42-5A6, 42-6B2, 42-8B1 and 42-7A7). The other clones presented a PCR product at the expected size. The clones 42-3B1 and 42-3B2 correspond to controls resulting from the transformation with the empty vector. (FIG. 6B) T7 assay performed on the 6 clones from the transformation with the UGP_TALE-Nuclease and 2 clones from the transformation with the empty vector. The negative control corresponds to a PCR performed on the clone 37-3B1 (transformed with the empty plasmid), not digested by the T7 enzyme. The T7 positive control corresponds to a PCR product carrying mutagenic events. The clones 42-5A1, 42-6B5, 42-7A2 and 42-7A3 are positive for T7 assay.

FIG. 7: Example of a mutagenic event induced by the TALE-Nuclease targeting the UDP glucose pyrophosphorylase gene (UGPase) (Query=SEQ ID NO: 54 and Target=SEQ ID NO: 55).

FIG. 11: Example of a mutagenic event induced by the TALE-Nuclease targeting the elongase gene (Query=SEQ ID NO: 56 and Target=SEQ ID NO: 57).

FIG. 13: Example of a mutagenic event induced by TALE-Nuclease within endogenous Glycerol 3 Phosphate deshydrogenase (G3PDH) (Query=SEQ ID NO: 58 and Target=SEQ ID NO: 59).

FIG. 14: Example of a mutagenic event induced by TALE-Nuclease within endogenous omega 3 desaturase gene (Query=SEQ ID NO: 60 and Target=SEQ ID NO: 61).

FIG. 15: Example of a mutagenic event induced by TALE-Nuclease within endogenous palmitoyl protein thioesterase gene (Query=SEQ ID NO: 62 and Target=SEQ ID NO: 63).

FIG. 16: Example of a mutagenic event induced by TALE-Nuclease within endogenous Enoyl ACP reductase gene (Query=SEQ ID NO: 64 and Target=SEQ ID NO: 65).

DETAILED DESCRIPTION OF THE INVENTION

Figure 1:
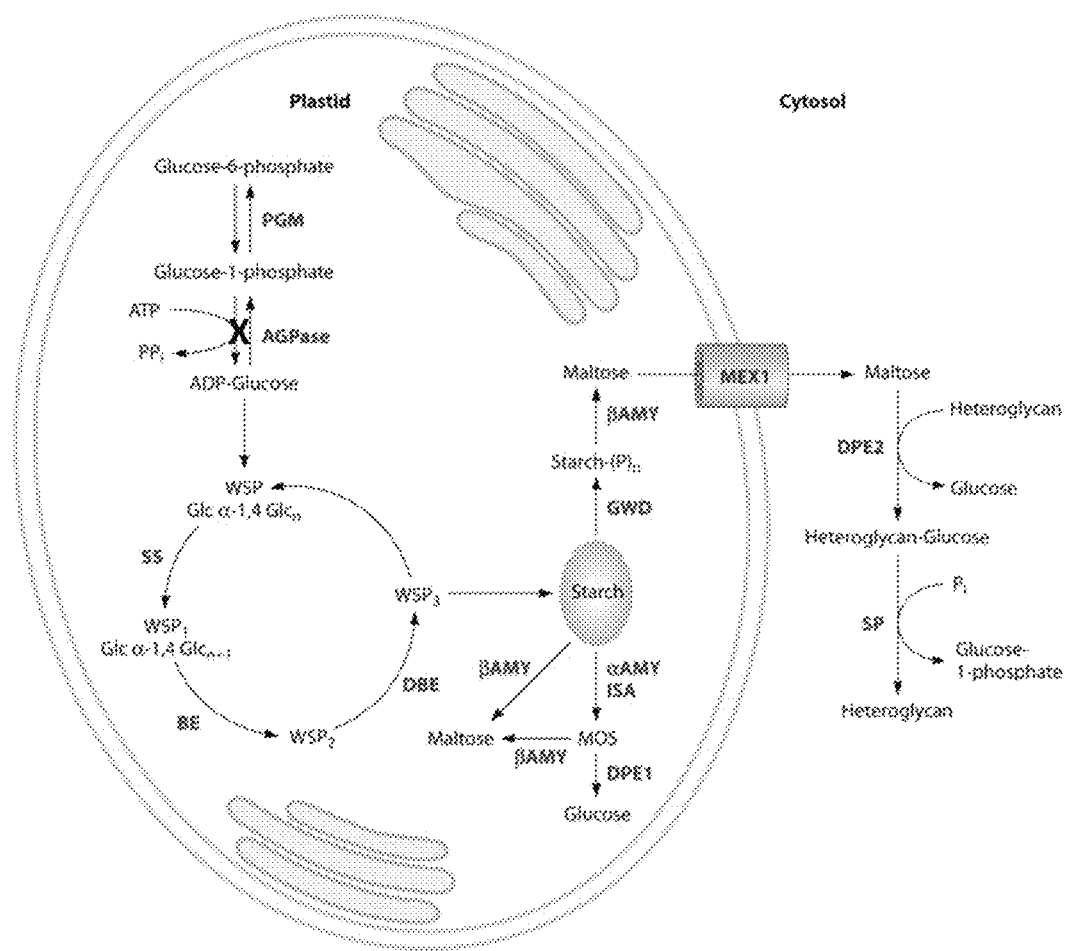
FIG. 1: Starch metabolism in green microalgae. Glucans are added to the water soluble polysaccharide (WSP) by α-1,4 glycosidic linkages (WSP1) until a branching enzyme highly branches the ends (WSP2). Some of these branches are trimmed (WSP3), and this process is repeated until a starch granule is formed. Phosphorolytic [Starch-(P)n] and hydrolytic degradation pathways are shown. αAMY, α-amylase; AGPase, ADP-glucose pyrophosphorylase; βAMY, β-amylases; BE, branching enzymes; DBE, debranching enzymes; DPE, disproportionating enzyme (1 and 2) α-1,4 glucanotransferase; Glc, glucose; GWD, glucan-water dikinases; ISA, isoamylases; MEX1, maltose transporter; MOS, malto-oligosaccharides; PGM, plastidial phosphoglucomutase; P, phosphate; Pi, inorganic phosphate; PPi, pyrophosphate; SP, starch phosphorylases; SS, starch synthases. (Radakovits, Jinkerson et al. 2010)

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986). The present invention relates to a modified diatom strain with high lipid quantity and/or quality content especially for biofuel production. In particular, the present invention relates to a modified diatom strain in which a gene involved in lipid metabolism has been inactivated. By inactivated, it is meant, that the gene encodes a non-functional protein or does not express the protein. Said gene is preferably inactivated by a rare-cutting endonuclease, more preferably by a TALE-nuclease, a MBBD-nuclease or a CRISPR/Cas9 nuclease.

Another option for gene inactivation is the use of RNA silencing to knock down gene expression (De Riso, Raniello et al. 2009) and particularly small-hairpin RNA (shRNA) that target nucleic acid encoding protein involved in lipid metabolism. Recent improvements in gene knockdown strategies include the development of high-throughput artificial-micro-RNA (armiRNA) techniques that are reportedly more specific and stable (Molnar, Bassett et al. 2009; Zhao, Wang et al. 2009). Another inactivation tool can be a double strand DNA, repressor molecules or dominant negative inhibitor protein capable of interrupting protein expression or function.

As a result, inactivation of said gene induces the production of an increased amount, storage and/or quality of lipids in diatom.

Diatoms are unicellular phototrophs identified by their species-specific morphology of their amorphous silica cell wall, which vary from each other at the nanometer scale. Diatoms includes as non limiting examples: *Phaeodactylum, Fragilariopsis, Thalassiosira, Coscinodiscus, Arachnoidiscusm, Aster omphalus, Navicula, Chaetoceros, Chorethron, Cylindrotheca fusiformis, Cyclotella, Lampriscus, Gyrosigma, Achnanthes, Cocconeis, Nitzschia, Amphora*, and *Odontella*.

In a more preferred embodiment, diatoms according to the invention are from the species: *Thalassiosira pseudonana* or *Phaeodactylum tricornutum*.

Figure 2:
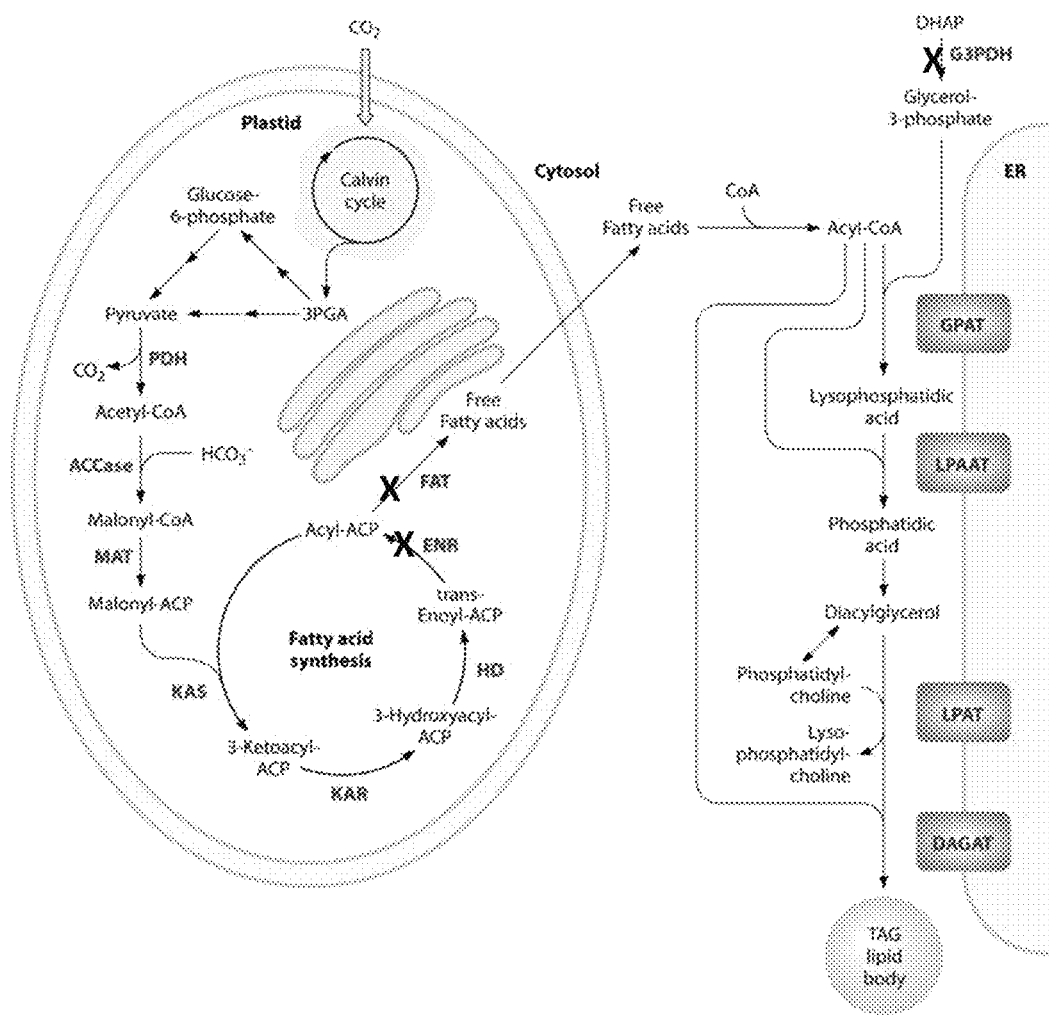
FIG. 2: Representative pathways of microalgal lipid biosynthesis. Free fatty acids are synthesized in the chloroplast, while TAGs may be assembled at the ER. ACCase, acetyl-CoA carboxylase; ACP, acyl carrier protein; CoA, coenzyme A; DAGAT, diacylglycerol acyltransferase; DHAP, dihydroxyacetone phosphate; ENR, enoyl-ACP reductase; FAT, fatty acyl-ACP thioesterase; G3PDH, gycerol-3-phosphate dehydrogenase; GPAT, glycerol-3-phosphate acyltransferase; HD, 3-hydroxyacyl-ACP dehydratase; KAR, 3-ketoacyl-ACP reductase; KAS, 3-ketoacyl-ACP synthase; LPAAT, lyso-phosphatidic acid acyltransferase; LPAT, lyso-phosphatidylcholine acyltransferase; MAT, malonyl-CoA: ACP transacylase; PDH, pyruvate dehydrogenase complex; TAG, triacylglycerols. (Radakovits, Eduafo et al. 2011)
Figure 3:
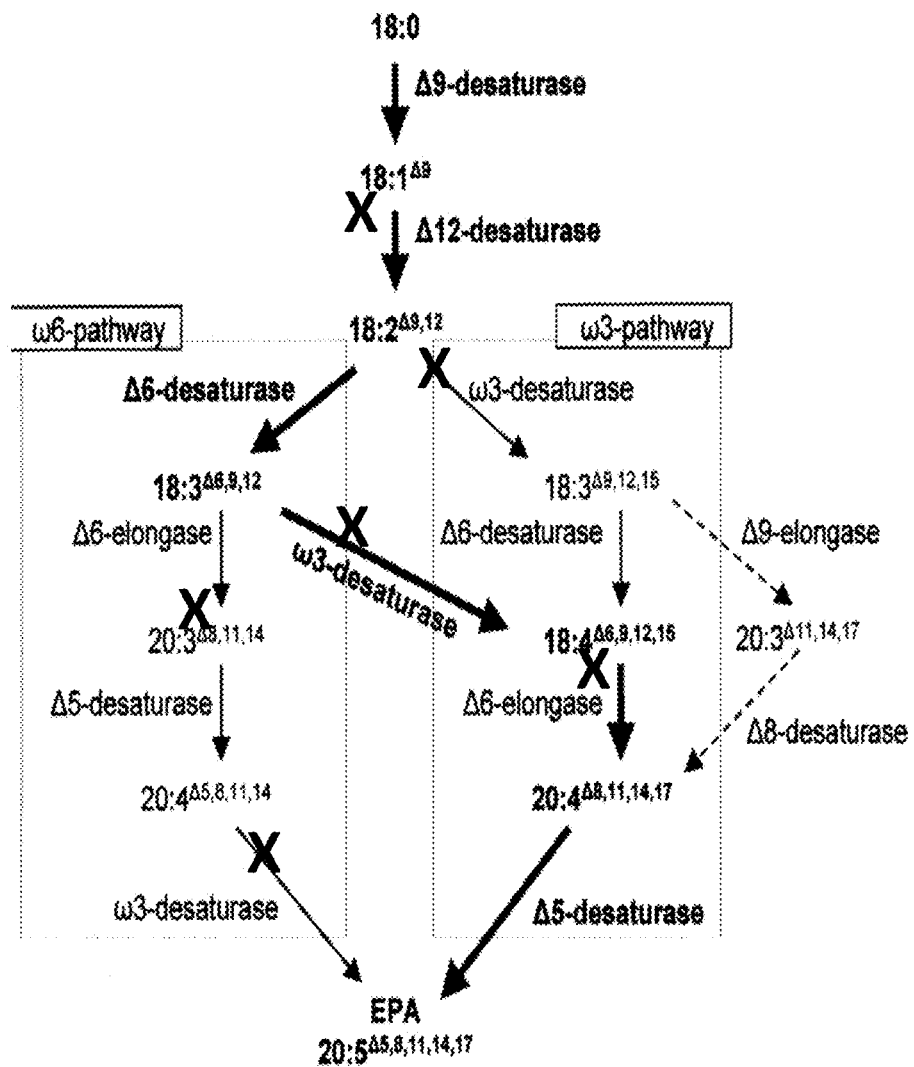
FIG. 3: Possible biosynthetic routes leading to eicosapentaenoic acid (EPA) biosynthesis in *Phaeodactylum tricornutum*. The classical ω6- and ω3-pathways are framed and the alternative ω3-pathway (involving Δ9-elongation and Δ8-desaturation) is shown with broken arrows. (Domergue, Lerchl et al. 2002)

By "genes involved in lipid metabolism" is meant any putative gene from the diatoms genomes that has similarity with a gene characterized in the literature encoding a protein taking part one biochemical reactions of lipid biosynthesis and catabolism, in particular one of the pathways illustrated in FIG. 1, 2 or 3, as well as pathways that modify the length and/or saturation of fatty acids (see for review, (Radakovits, Jinkerson et al. 2010).

The invention envisions that many genes involved in lipid biosynthesis can be subjected to knock-out or knock-in, individually or collectively, in order to increase the production or storage (internal accumulation) of lipids and/or to improve the quality of the lipids.

The genes encoding enzymes involved in the pathways of fatty acid synthesis can encode proteins having for instance acetyl-CoA carboxylase, fatty acid synthase, 3-ketoacyl_acyl-carrier protein synthase III, glycerol-3-phospate deshydrogenase (G3PDH), Enoyl-acyl carrier protein reductase (Enoyl-ACP-reductase), glycerol-3-phosphate acyltransferase, lysophosphatidic acyl transferase or diacylglycerol acyltransferase, phospholipid:diacylglycerol acyltransferase, phoshatidate phosphatase, fatty acid thioesterase such as palmitoyl protein thioesterase, or malic enzyme activities (see FIG. 2).

Another strategy to induce lipid accumulation within diatom is to decrease lipid catabolism. Genes involved in the activation of both triacylglycerol and free fatty acids, as well as genes directly involved in β-oxidation of fatty acids can be inactivated to increase cellular lipid content. For example, acyl-CoA synthetase, 3-ketoacyl-CoA thiolase, acyl-CoA oxidase activity, phosphoglucomutase, can be inactivated. Lipases are enzymes that de-esterify carboxyl esters, such as triacylglycerols and phospholipids. Many of putative lipase can be found in diatoms. As non limiting example in *P. tricornutum* Phatrdraft_44231 which encodes a putative tricaylglycerol lipase, Phatrdraft_50397 can be inactivated to induce lipid accumulation.

According to the invention, the cellular lipid content of the diatoms can also be increased by inactivating metabolic pathways leading to the accumulation of energy-rich storage compounds, such as chrysolaminarin (β-1, 3-glucan). For instance, UDP-glucose pyrophosphorylase, ADP-glucose pyrophosphorylase, isoamylase genes can be inactivated in these diatoms strains (see FIG. 1).

In addition, the quality of lipids can be increased with regard to suitability as biofuel, by modifying genes involved in the carbon chain length and the degree of unsaturation of the fatty acids which can affect the cold flow and oxidative stability properties of the biofuel derived from the feedstock of the diatom. Examples of these are delta 12 desaturase, delta 9 desaturase, omega 3 desaturase and elongase enzymes (see FIG. 3).

In another aspect, as non-limiting examples, thioesterases enzymes, such as acyl-ACP thioesterases specific for shorter chain length fatty acids can be overexpressed to improve cold flow properties (Hu, Sommerfeld et al. 2008; Radakovits, Jinkerson et al. 2010).

Here, the present inventors have more particularly identified a selection of putative genes in the diatoms genomes encoding putative enzymes selected from the group consisting of: glycerol-3-phosphate deshydrogenase, ω3-desaturase, palmitoyl protein thioesterase, Enoyl ACP reductase, Δ12 desaturase, UDP-glucose pyrophosphorylase and elongase.

They have designed rare-cutting endonuclease capable of targeting these genes or gene sequences having at least 70%, preferably at least 75%, 80%, 85%, 90%, 95% sequence identity with any one of the sequences selected from the group consisting of: SEQ ID NO: 3, 14, 22, 30, 36, 42 and 48. In particular embodiment, the rare-cutting endonuclease is capable of cleaving target sequence selected from the group consisting of: SEQ ID NO: 6, 17, 25, 33, 39, 45 and 51.

The resulting diatoms modified according to the invention can produce an increased amount of lipid per cell of at least 10% compared to the wild type strain, particularly at least 20, 30, 40, 50%, more preferably at least 75%, 100%, 200%, 300% compared to the wild type strain. In another words, the present invention relates to modified diatoms with a lipid content of at least 30%, preferably at least 40%, 50%, 60%, 70%, 80,% of dry weight.

In particular embodiment, the present invention relates to modified diatoms which preferably produce an increased amount of shorter chain length fatty acids compared to wild type, preferably fatty acids having chain of 12, 14, 16, 18, 20 carbons, preferably between 16 and 20, more preferably between 16 and 18 carbons, again more preferably between 12 and 16 carbons. In another particular embodiment, the present invention relates to modified diatoms which preferably produce fatty acids with a lower degree of unsaturation, preferably modified diatoms produce an increase amount of fatty acids with no more than 5 preferably 4, 3, 2 or 1 double bond(s) between carbon atoms, more preferably fatty acids with no double bonds between carbon atoms (saturated fatty acids).

By increased amount of product, it is meant that the modified diatoms present an increase production of at least 10%, preferably of at least 20%, 30%, 40% or 50%, more preferably at least 75%, 100%, 200%, 300% compared to the wild type strain.

The lipid content analysis can be performed following protocol previously described in (Vieler, Wilhelm et al. 2007; Lamaziere, Wolf et al. 2012; Lamaziere, Wolf et al. 2013).

Due to the ease of the present genetic engineering method, modified diatom strains can comprise simultaneous modifications to modulate the lipid metabolic pathway, for instance simultaneous activation and/or inactivation of several key enzymes involved in lipid metabolism.

In particular embodiment, the modified diatoms can comprise one inactivated lipid gene by insertion of a transgene. In particular embodiment, said transgene encodes for an enzyme involved in the lipid metabolism. In this case, both inactivation of endogenous gene and overexpression of the transgene can improve the production and the quality of lipid within diatoms. As non-limiting example, said modified diatom can comprise an inactivated gene selected from the group consisting of: glycerol-3-phosphate deshydrogenase, ω3-desaturase, palmitoyl protein thioesterase, eonyl ACP reductase, elongase, UDP-glucose pyrophosphorylase and Δ12 desaturase genes, and a transgene comprising at least one thioesterase gene.

The lipid gene according to the present invention can be modified by introducing into the diatom a DNA binding domain which specifically targets the lipid gene of interest. In particular, the method for lipid gene targeted modification in diatom can comprise: selecting a target sequence within a gene of a diatom strain putatively involved in lipid metabolism; providing a DNA binding domain to target said gene; introducing said DNA binding domain into diatom; optionally selecting diatom producing an increased amount, storage and/or quality of lipids. Said DNA binding domain can be as non limiting examples a TALE binding domain or a MBBBD binding domain. Said DNA binding domain can be fused with a transcription activator or a repressor (i. e. a transcription regulator) or a protein that interacts with or modifies other proteins implicating in DNA processing. Non limiting examples of DNA processing activities can be for example creating or modifying epigenetic regulatory elements, making site-specific insertions, deletions, or repairs in DNA, controlling gene expression, and modifying chromatin structure.

In a particular aspect of the invention, the lipid gene according to the present invention can be modified by introducing into the diatom a rare-cutting endonuclease which specifically cleaves the lipid gene of interest. In particular, the method for lipid gene targeted modification in diatom can comprise: selecting a target sequence within a gene of a diatom strain putatively involved in lipid metabolism; providing a rare-cutting endonuclease to target and inactivate said gene; introducing said rare-cutting endonuclease into diatom; optionally selecting diatom in which said putative gene involved in lipid metabolism has been inactivated and producing an increased amount, storage and/or quality of lipids. Said rare-cutting endonuclease can be as non-limiting example, a TALE-nuclease, a MBBBD-nuclease or a CRISPR/Cas9 nuclease which is capable of targeting specifically the selected target sequence. Preferably, selected target sequence is comprised within a putative gene involved in the lipid metabolism as described above. In particular, said target sequence is comprised within a gene selected from the group consisting of: glycerol-3-phosphate deshydrogenase, ω3-desaturase, palmitoyl protein thioesterase, eonyl ACP reductase, elongase, UDP-glucose pyrophosphorylase and Δ12 desaturase genes. More particularly, said rare-cutting endonuclease is capable of targeting a gene having at least 70%, preferably at least 75%, 80%, 85%, 90%, 95% sequence identity with any one of the sequences selected from the group consisting of: SEQ ID NO: 3, 14, 22, 30, 36, 42 and 48. In particular embodiment, the rare-cutting endonuclease is capable of cleaving target sequence selected from the group consisting of: SEQ ID NO: 6, 17, 25, 33, 39, 45 and 51. By "cleavage", it is meant a double strand break or single strand break in the target sequence. It is also encompassed in the present invention said TALE-nucleases, preferably said TALE-nuclease encoding by the plasmid sequence selected from the group consisting of: SEQ ID NO: 4, 5, 15, 16, 23, 24, 31, 32, 37, 38, 43, 44, 49 and 50.

Said modified target sequence can result from NHEJ events or homologous recombination. The double strand breaks caused by said rare-cutting endonucleases are commonly repaired through the distinct mechanisms of homologous recombination or non-homologous end joining (NHEJ). Although homologous recombination typically uses the sister chromatid of the damaged DNA as a donor matrix from which to perform perfect repair of the genetic lesion, NHEJ is an imperfect repair process that often results in changes to the DNA sequence at the site of the double strand break. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts.

In a particular embodiment of the methods envisaged herein the mutagenesis is increased by transfecting the cell with a further transgene coding for a catalytic domain. In a more preferred embodiment, said catalytic domain is a DNA end-processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise a protein domain or catalytically active derivate of the protein domain selected from the group consisting of hExoI (EXO1_HUMAN), Yeast ExoI (EXO1_YEAST), E. coli ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a more preferred embodiment, said catalytic domain has an exonuclease activity, in particular a 3'-5' exonuclease activity. In a more preferred embodiment, said catalytic domain has TREX exonuclease activity, more preferably TREX2 activity. In another preferred embodiment, said catalytic domain is encoded by a single chain TREX polypeptide. In a particular embodiment, said catalytic domain is fused to the N-terminus or C-terminus of said rare-cutting endonuclease. It has been found that the coupling of the enzyme SCTREX2 with an endonuclease such as a TALE-nuclease ensures high frequency of targeted mutagenesis (WO2012054858, WO2013009525).

Endonucleolytic breaks are known to stimulate homologous recombination. Therefore, in particular embodiments, said modified target sequence can result to donor matrix insertion (knock-in) into chosen loci of the genome. In particular embodiments, the knock-in diatom is made by introducing into said diatom a genome engineering nuclease as described above, to induce a cleavage within or adjacent to target sequence, and a donor matrix comprising a transgene to introduce said transgene by a knock-in event. Said donor matrix comprises a sequence homologous to at least a portion of the target nucleic acid sequence, such that homologous recombination occurs between the target DNA sequence and the donor matrix. In particular embodiments, said donor matrix comprises first and second portions which are homologous to region 5' and 3' of the target nucleic acid, respectively. Following cleavage of the target nucleic acid sequence, a homologous recombination event is stimulated between the genome containing the target nucleic acid sequence and the donor matrix. Preferably, homologous sequences of at least 50 bp, preferably more than 100 bp and more preferably more than 200 bp are used within said donor matrix. Therefore, the donor matrix is preferably from 200 bp to 6000 bp, more preferably from 1000 bp to 2000 bp.

Depending on the location of the targeted sequence wherein cleavage event has occurred, such donor matrix can be used to knock-out a gene, e.g. when the donor matrix is located within the open reading frame of said gene, or to introduce new sequences or genes of interest. Sequence insertions by using such donor matrix can be used to modify a targeted existing gene, by correction or replacement of said gene (allele swap as a non-limiting example), or to up- or down-regulate the expression of the targeted gene (promoter swap as non-limiting example), said targeted gene correction or replacement conferring one or several commercially desirable traits.

In particular embodiment, said donor matrix can comprise a transgene encoding an enzyme involved in the lipid metabolism. Said donor matrix can be inserted in the target sequence by homologous recombination. The transgene replaces and inactivates the target gene. In this case, both inactivation of endogenous gene and overexpression of the transgene can improve the production and the quality of lipid within diatoms. As non limiting example, said donor matrix can comprise a thioesterase gene and the target sequence can be selected from the group consisting of: glycerol-3-phosphate deshydrogenase, ω3-desaturase, palmitoyl protein thioesterase, Enoyl ACP reductase, Δ12 desaturase, UDP-glucose pyrophosphorylase and elongase genes.

Molecules can be introduced into the diatom by transformation method well-known in the art. In various embodiments, nucleotide sequence for example vector encoding rare-cutting endonuclease and/or donor matrix can be introduced into diatom nuclei by for example without limitation, electroporation, magnetophoresis, micropartile bombardment. Direct introduction of purified endonucleases of the present invention in diatom can be considered.

Transformation methods require effective selection markers to discriminate successful transformants cells. The majority of the selectable markers include genes with a resistance to antibiotics. Only few publications refer to selection markers usable in Diatoms. (Dunahay, Jarvis et al. 1995) report the use of the neomycin phosphotransferase II (nptII), which inactivates G418 bp phosphorylation, in *Cyclotella cryptica, Navicula saprophila* and *Phaeodactylum tricornutum* species. (Falciatore, Casotti et al. 1999; Zaslayskaia, Lippmeier et al. 2001) report the use of the Zeocin or Phleomycin resistance gene (Sh ble), acting by stochiometric binding, in *Phaeodactylum tricornutum* and *Cylindrotheca fusiformis* species. In (Falciatore, Casotti et al. 1999; Zaslayskaia, Lippmeier et al. 2001), the use of N-acetyltransferase 1 gene (Nat1) conferring the resistance to Nourseothricin by enzymatic acetylation is reported in *Phaeodactylum tricornutum* and *Thalassiosira pseudonana*. It is understood that use of the previous specific selectable markers are comprised in the scope of the present invention and that use of other genes encoding other selectable markers including, for example and without limitation, genes that participate in antibiotic resistance. In a more preferred embodiment, the vector encoding for selectable marker and the vector encoding for rare-cutting endonuclease are different vectors.

Increase lipid synthesis can result in a reduction of cell division. In such case, modification of lipid gene expression can be beneficial if they can be controlled by an inducible promoter that can be activated for instance once the modified diatoms have grown to a high density and have entered stationary phase. Thus, in particular embodiments, the gene encoding a rare-cutting endonuclease or the transgene according to the present invention can be placed under the control of a promoter. An inducible promoter is a promoter which initiates transcription only when it is exposed to some particular (typically external) stimulus. Particularly preferred for the present invention are: a light-regulated promoter, nitrate reductase promoter, eukaryotic metallothionine promoter, which is induced by increased levels of heavy metals, prokaryotic lacZ promoter which is induced in response to isopropyl-β-D-thiogalacto-pyranoside (IPTG), steroid-responsive promoter, tetracycline-dependent promoter and eukaryotic heat shock promoter which is induced by increased temperature.

In another aspect, it is also encompassed in the scope of the present invention, a modified algal cell obtained or obtainable by the methods described above. In particular embodiments, such modified algal cells are characterized by the presence of a sequence encoding a rare-cutting endonuclease transgene and a modification in a targeted lipid gene, preferably in both alleles.

The present invention also relates to methods to produce biofuel using the modified diatoms described above.

In particular, the present invention relates to a method for producing lipids comprising one or several of the steps of:
(a) cultivating a modified diatom strain as described above in a adapted culture medium,
(b) optionally, harvesting modified diatom strains,
(c) extracting the lipids from the diatoms.

Several extraction methods for lipids are well-known in the art: physical extraction, chemical extraction, supercritical fluid extraction, in situ extraction, ultrasonic assisted extraction or pulsed electric field technology. Physical methods destruct the algal cells and consist of sonication, homogenization, French pressing, expelling and beads milling. For the chemical solvent extraction, several extractors and mixtures are known; for example, hexane, chloroform, methanol, isopropanol and acetone. For the supercritical fluid extraction, the extraction medium is in many cases CO2. In the in situ extraction, the algae are not harvested and do not need to be dewatered or dried. The lipids are extracted from living cells (Frenz, Largeau et al. 1989; King 1996; Lee, Yoon et al. 1998; Sievers 1998; Hejazi and Wijffels 2004; Herrero, Jaime et al. 2006; Doucha and Livansky 2008; Wei, Gao et al. 2008; Shen, Yuan et al. 2009; Mercer and Armenta 2011).

The present invention also relates to a method comprising the step of producing biofuel from the lipids produced by diatoms, especially triacylglycerol compounds.

The biofuel production can be performed as described in (Kröger and Müller-Langer 2012), WO2009063296). The biofuel production can be realized via (trans)esterification, in situ transesterification wherein the algae medium is directly mixed with the solvent, catalyst and alcohol, by hydroprocessing from algal lipids called hydroprocessed esters and fatty acids. The present invention also relates to a step of transforming the extracted lipids into a cosmetic or a food product, especially for their high content of essential fatty acids, more particularly as containing omega-3 fatty acids, such as docosahexaenoic acid (DHA) and Eicosapentaenoic acid (EPA or icosapentaenoic acid). The present invention also encompasses other uses of the modified diatoms or their extracted lipids. In particular, the modified diatoms according to the invention can be cultivated for their oil contents and directly used under their algal forms, as an essential source of fatty acids in animal alimentation, in particular to breed fish or shellfish.

Definitions

By "gene" it is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns and a 3' untranslated region. The gene may further be comprised of terminators, enhancers and/or silencers.

By "genome" it is meant the entire genetic material contained in a cell such as nuclear genome, chloroplastic genome, mitochondrial genome.

As used herein, the term "locus" is the specific physical location of a DNA sequence (e.g. of a gene) on a nuclear, mitochondria or choloroplast genome. As used in this specification, the term "locus" usually refers to the specific physical location of an endonuclease's target sequence. Such a locus, which comprises a target sequence that is recognized and cleaved by an endonuclease according to the invention, is referred to as "locus according to the invention".

By "target sequence" is intended a polynucleotide sequence that can be processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria or chloroplasts as non-limiting examples. The nucleic acid target sequence is defined by the 5' to 3' sequence of one strand of said target.

As used herein, the term "transgene" refers to a sequence inserted at in an algal genome. Preferably, it refers to a sequence encoding a polypeptide. Preferably, the polypeptide encoded by the transgene is either not expressed, or expressed but not biologically active, in the diatom in which the transgene is inserted. Most preferably, the transgene encodes a polypeptide useful for increasing the quantity and/or the quality of the lipid in the diatom. Also, the transgene can be a sequence inserted in an algae genome for producing an interfering RNA.

By "homologous" it is meant a sequence with enough identity to another one to lead to homologous recombination between sequences, more particularly having at least 95% identity, preferably 97% identity and more preferably 99%.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

By "DNA binding domain", it is meant a protein domain capable of binding a target nucleic acid sequence, preferably a DNA molecule. The DNA binding domain recognizes and binds nucleic acid at specific polynucleotide sequences, further referred to as "nucleic acid target sequence". Transcription Activator like Effector (TALE) are proteins from the bacterial species *Xanthomonas* comprise a plurality of repeat sequences, each repeat comprising di-residues in position 12 and 13 (RVD) that are specific to each nucleotide base of the nucleic acid targeted sequence. TALE binding domain is composed by a variable number of 33-35 amino acid repeat modules. These repeat modules are nearly identical to each other except for two variable amino acids located at positions 12 and 13 (i.e. Repeat Variable Di residues, RVD). The nature of residues 12 and 13 determines base preferences of individual repeat module. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. Binding domains with similar base-per-base nucleic acid binding properties (modular base-per-base specific nucleic acid binding domains (MBBBD) can also be derived from new modular proteins recently discovered by the applicant in a different bacterial species. Said MBBBD can be engineered, for instance, from the newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica* (Lackner, Moebius et al. 2011).

By "rare-cutting endonuclease", it is meant any wild type or variant enzyme capable of catalyzing the hydrolysis (cleavage) of bonds between nucleic acids within a DNA or RNA molecule, preferably a DNA molecule. A rare-cutting endonucelase is highly specific, recognizing nucleic acid target sites ranging from 10 to 45 base pairs (bp) in length, usually ranging from 10 to 35 base pairs in length. The endonuclease according to the present invention recognizes and cleaves nucleic acid at specific polynucleotide sequences, further referred to as "nucleic acid target sequence".

"TALE-nuclease" or "MBBBD-nuclease" refers to engineered proteins resulting from the fusion of a nucleic acid binding domain typically derived from Transcription Activator like Effector proteins (TALE) or MBBBD binding domain, with an endonuclease catalytic domain. Such catalytic domain is preferably a nuclease domain and more preferably a domain having endonuclease activity, like for instance I-Tevl, ColE7, NucA and Fok-I. In a more preferred embodiment, said nuclease is a monomeric TALE-Nuclease or MBBBD-nuclease. A monomeric Nuclease is a Nuclease that does not require dimerization for specific recognition and cleavage, such as the fusions of engineered TALE repeats with the catalytic domain of I-Tevl described in WO2012138927. TALE-nuclease have been already described and used to stimulate gene targeting and gene modifications (Boch, Scholze et al. 2009; Moscou and Bogdanove 2009; Christian, Cermak et al. 2010). Such engineered TAL-nucleases are commercially available under the trade name TALEN™ (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the proto-spacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010).

Are also encompassed in the scope of the present invention rare-cutting endonuclease variants which present a sequence with high percentage of identity or high percentage of homology with sequences of rare-cutting endonuclease described in the present application, at nucleotidic or polypeptidic levels. By high percentage of identity or high percentage of homology it is intended 70%, more preferably 75%, more preferably 80%, more preferably 85%, more preferably 90%, more preferably 95, more preferably 97%, more preferably 99% or any integer comprised between 70% and 99%.

By "vector" is intended to mean a nucleic acid molecule capable of transporting another nucleic acid to which it has been linked. A vector which can be used in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those skilled in the art and commercially available. Some useful vectors include, for example without limitation, pGEM13z. pGEMT and pGEMTEasy {Promega, Madison, Wis.); pSTBluel (EMD Chemicals Inc. San Diego, Calif.); and pcDNA3.1, pCR4-TOPO, pCR-TOPO-II, pCRBlunt-II-TOPO (Invitrogen, Carlsbad, Calif.). Preferably said vectors are expression vectors, wherein the sequence(s) encoding the rare-cutting endonuclease of the invention is placed under control of appropriate transcriptional and translational control elements to permit production or synthesis of said rare-cutting endonuclease. Therefore, said polynucleotide is comprised in an expression cassette. More particularly, the vector comprises a replication origin, a promoter operatively linked to said polynucleotide, a ribosome-binding site, an RNA-splicing site (when genomic DNA is used), a polyadenylation site and a transcription termination site. It also can comprise an enhancer. Selection of the promoter will depend upon the cell in which the polypeptide is expressed. Preferably, when said rare-cutting endonuclease is a heterodimer, the two polynucleotides encoding each of the monomers are included in two vectors to avoid intraplasmidic recombination events. In another embodiment the two polynucleotides encoding each of the monomers are included in one vector which is able to drive the expression of both polynucleotides, simultaneously. In some embodiments, the vector for the expression of the rare-cutting endonucleases according to the invention can be operably linked to an algal-specific promoter. In some embodiments, the algal-specific promoter is an inducible promoter. In some embodiments, the algal-specific promoter is a constitutive promoter. Promoters that can be used include, for example without limitation, a Pptcal promoter (the $CO_2$ responsive promoter of the chloroplastic carbonic anyhydrase gene, ptcal, from *P. tricornutum*), a NITI promoter, an AMTI promoter, an AMT2 promoter, an AMT4 promoter, a RHI promoter, a cauliflower mosaic virus 35S promoter, a tobacco mosaic virus promoter, a simian virus 40 promoter, a ubiquitin promoter, a PBCV-I VP54 promoter, or functional fragments thereof, or any other suitable promoter sequence known to those skilled in the art. In another more preferred embodiment according to the present invention the vector is a shuttle vector, which can both propagate in *E. coli* (the construct containing an appropriate selectable marker and origin of replication) and be compatible for propagation or integration in the genome of the selected algae.

The term "promoter" as used herein refers to a minimal nucleic acid sequence sufficient to direct transcription of a nucleic acid sequence to which it is operably linked. The term "promoter" is also meant to encompass those promoter elements sufficient for promoter-dependent gene expression controllable for cell-type specific expression, tissue specific expression, or inducible by external signals or agents; such elements may be located in the 5' or 3' regions of the naturally-occurring gene.

By "inducible promoter" it is mean a promoter that is transcriptionally active when bound to a transcriptional activator, which in turn is activated under a specific condition(s), e.g., in the presence of a particular chemical signal or combination of chemical signals that affect binding of the transcriptional activator, e.g., $CO_2$ or $NO_2$, to the inducible promoter and/or affect function of the transcriptional activator itself.

The term "transfection" or "transformation" as used herein refer to a permanent or transient genetic change, preferably a permanent genetic change, induced in a cell following incorporation of non-host nucleic acid sequences.

The term "host cell" refers to a cell that is transformed using the methods of the invention. In general, host cell as used herein means an algal cell into which a nucleic acid target sequence has been modified.

By "catalytic domain" is intended the protein domain or module of an enzyme containing the active site of said enzyme; by active site is intended the part of said enzyme at which catalysis of the substrate occurs. Enzymes, but also their catalytic domains, are classified and named according to the reaction they catalyze. The Enzyme Commission number (EC number) is a numerical classification scheme for enzymes, based on the chemical reactions they catalyze (http://www.chem.qmul.ac.uk/iubmb/enzyme/).

By "mutagenesis" is understood the elimination or addition of at least one given DNA fragment (at least one nucleotide) or sequence, bordering the recognition sites of rare-cutting endonuclease.

By "NHEJ" (non-homologous end joining) is intended a pathway that repairs double-strand breaks in DNA in which the break ends are ligated directly without the need for a homologous template. NHEJ comprises at least two different processes. Mechanisms involve rejoining of what remains of the two DNA ends through direct re-ligation {Critchlow, 1998 #17} or via the so-called microhomology-mediated end joining (Ma, Kim et al. 2003) that results in small insertions or deletions and can be used for the creation of specific gene knockouts.

The term "Homologous recombination" refers to the conserved DNA maintenance pathway involved in the repair of DSBs and other DNA lesions. In gene targeting experiments, the exchange of genetic information is promoted between an endogenous chromosomal sequence and an exogenous DNA construct. Depending of the design of the targeted construct, genes could be knocked out, knocked in, replaced, corrected or mutated, in a rational, precise and efficient manner. The process requires homology between the targeting construct and the targeted locus. Preferably, homologous recombination is performed using two flanking sequences having identity with the endogenous sequence in order to make more precise integration as described in WO9011354.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of", "chosen from" and the like include mixtures of the specified materials.

Where a numerical limit or range is stated herein, the endpoints are included. Also, all values and sub-ranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1: Increased Lipid Content in Diatoms Using TALE-Nuclease Targeting the UDP Glucose Pyrophosphorylase (UGPase) Gene In order to determine the impact of UGPase gene inactivation on lipid content in diatoms, one engineered TALE-Nuclease to induce targeted mutagenesis in UGPase gene (SEQ ID NO: 3) in diatoms, one engineered TALE-Nuclease, called UGP TALE-Nuclease encoded by the pCLS19745 (SEQ ID NO: 4) and pCLS19749 (SEQ ID NO: 5) plasmids designed to cleave the DNA sequence 5'TGC-CGCCTTCGAGTCGACCTATGG-TAGTCTCGTCTCGGGTGATTCCGGAA-3' (SEQ ID NO: 6) were used. These TALE-Nuclease encoding plasmids were co-transformed with a plasmid conferring resistance to nourseothricin (NAT) in a wild type diatom strain. The individual clones resulting from the transformation were screened for the presence of mutagenic events which lead to UGPase gene inactivation. The identified clones were analyzed for their lipid contents using Bodipy labeling 493/503 (Molecular Probe).

Materials and Methods

Culture Conditions

*Phaeodactylum tricornutum* Bohlin clone CCMP2561 was grown in filtered Guillard's f/2 medium without silica [(40°/°° w/v Sigma Sea Salts S9883, supplemented with 1× Guillard's f/2 marine water enrichment solution (Sigma G0154)] in a Sanyo incubator (model MLR-351) at a constant temperature (20+/−0.5° C.). The incubator is equipped with white cold neon light tubes that produce an illumination of about 120 µmol photons $m^{-2}$ $s^{-1}$ and a photoperiod of 12 h light: 12 h darkness (illumination period from 9 AM to 9 PM). Liquid cultures were made in vented cap flasks put on an orbital shaker (Polymax 1040, Heidolph) with a rotation speed of 30 revolutions $min^{-1}$ and an angle of 5°.

Genetic Transformation $5.10^7$ cells were collected from exponentially growing liquid cultures (concentration of about $10^6$ cells/ml) by centrifugation (3000 rpm for 10 minutes at 20° C.). The supernatant was discarded and the cell pellet resuspended in 500 µl of fresh f/2 medium. The cell suspension was then spread on the center one-third of a 10 cm 1% agar plate containing 20°/°° sea salts supplemented with f/2 solution without silica. Two hours later, transformation was carried out using microparticle bombardment (Biolistic PDS-1000/He Particle Delivery System (BioRad)). The protocol is adapted from Falciatore et al., (1999) and Apt et al., (1999) with minor modifications. Briefly, M17 tungstene particles 1.1 µm diameter, BioRad) were coated with 9 µg of a total amount of DNA composed of 1.5 µg (experiment 2) or 3 µg (experiment 1) of each monomer of TALE-Nucleases (pCLS19745 and pCLS19749), 3 µg of the NAT selection plasmid (pCLS16604) (SEQ ID NO: 1) and 3 µg of an empty vector (pCLS0003) (SEQ ID NO: 2) using 1.25M CaCl2 and 20 mM spermidin according to the manufacturer's instructions. As a negative control, beads were coated with a DNA mixture containing 3 µg of the NAT selection plasmid (pCLS16604) and 6 µg of an empty vector (pCLS0003) (SEQ ID NO: 2). Agar plates with the diatoms to be transformed were positioned at 7.5 cm from the stopping screen within the bombardment chamber (target shelf on position two). A burst pressure of 1550 psi and a vacuum of 25 Hg/in were used. After bombardment, plates were incubated for 48 hours with a 12 h light: 12 h dark photoperiod.

Selection

Two days post transformation, bombarded cells were gently scrapped with 700 µl of f/2 medium without silica and spread on two 10 cm 1% agar plates (20°/°° sea salts supplemented with f/2 medium without silica) containing 300 µg $ml^{-1}$ nourseothricin (Werner Bioagents). Plates were then placed in the incubator under a 12 h light: 12 h darkness cycle for at least three weeks. 3 to 4 weeks after transformation, on average, resistant colonies resulting from a stable transformation were re-streaked on fresh 10 cm 1% agar plates containing 300 µg·$ml^{-1}$ nourseothricin.

Characterization

A-Colony Screening

Resistant colonies were picked and dissociated in 20 µl of lysis buffer (1% TritonX-100, 20 mM Tris-HCl pH8, 2 mM EDTA) in an eppendorf tube. Tubes were vortexed for at least 30 sec and then kept on ice for 15 min. After heating for 10 min at 85° C., tubes were cooled down at RT and briefly centrifuged to pellet cells debris. Supernatants were used immediately or stocked at 4° C. 50 of a 1:5 dilution in milliQ H$_2$O of the supernatants, were used for each PCR reaction. Specific primers for TALE-Nuclease screens: TALE-Nuclease_For 5'-AATCTCGCCTATTCATGGTG-3' (SEQ ID NO: 7) and HA_Rev 5'-TAATCTGGAACATCG-TATGGG-3' (SEQ ID NO: 8). TALE-Nuclease_For 5'-AATCTCGCCTATTCATGGTG-3' (SEQ ID NO: 7) and STag_Rev 5'-TGTCTCTCGAACTTGGCAGCG-3' (SEQ ID NO: 9).

B-Identification of Mutagenic Events

The UGPase target was amplified using a 1:5 dilution of the colony lysates with sequence specific primers flanked by adaptators needed for HTS sequencing on a 454 sequencing system (454 Life Sciences) and the two following primers: UGP_For 5'-CCATCTCATCCCTGCGTGTCTC-CGACTCAG-Tag-GTTGAATCGGAATCGCTAACTCG-3' (SEQ ID NO: 10) and UGP_Rev 5'-CCTATCCCCTGT-GTGCCTTGGCAGTCTCAG—Tag-GACTTGTTTGGCGGTCAAATCC-3' (SEQ ID NO: 11).

The PCR products were purified on magnetic beads (Agencourt AMPure XP, Beckman Coulter) and quantified with a NanoDrop 1000 spectrophotometer (Thermo Scientifioc). 50 ng of the amplicons were denatured and then annealed in 10 µl of the annealing buffer (10 mM Tris-HCl pH8, 100 mM NaCl, 1 mM EDTA) using an Eppendorf MasterCycle gradient PCR machine. The annealing program is as follows: 95° C. for 10 min; fast cooling to 85° C. at 3° C./sec; and slow cooling to 25° C. at 0.3° C./sec. The totality of the annealed DNA was digested for 15 min at 37° C. with 0.5 µl of the T7 Endonuclease I (10 U/µl) (M0302, Biolabs) in a final volume of 200 (1xNEB buffer 2, Biolabs). 10 µl of the digestion were then loaded on a 10% polyacrylamide MiniProtean TBE precast gel (BioRad). After migration the gel was stained with SYBRgreen and scanned on a Gel Doc XR+ apparatus (BioRad).

C-Measure of the Mutagenesis Frequency by Deep Sequencing

The UGPase target was amplified with specific primers flanked by adaptators needed for HTS sequencing on the 454 sequencing system (454 Life Sciences) using the primer UGP_For 5'-5'-CCATCTCATCCCTGCGTGTCTC-CGACTCAG-Tag-GTTGAATCGGAATCGCTAACTCG-3'-3' (SEQ ID NO: 12) and UGP_Rev 5'-CCTATCCCCT-GTGTGCCTTGGCAGTCTCAG-GACTTGTTTGGCGGTCAAATCC-3' (SEQ ID NO: 13). 5000 to 10 000 sequences per sample were analyzed.

D-Phenotypic Characterization of UDP KO Clones by Bodipy Labeling

Cells were re-suspended at the density of 5.10$^5$ cells/ml and washed twice in culture medium (filtered Guillard's f/2 medium without silica). The bodipy labeling was performed with 10 µM of final concentration of Bodipy 493/503 (Molecular Probe) in presence of 10% of DMSO during 10 minutes at room temperature in the dark. The fluorescence intensity was measured by flow cytometry at 488 nM (MACSQuant Analyzer, Miltenyi Biotec).

E-Lipid Content Analysis

The lipid content analysis was performed by the APLILIPID company (Applied Lipidomics Investigation) using protocol previously described in (Vieler, Wilhelm et al. 2007; Lamaziere, Wolf et al. 2012; Lamaziere, Wolf et al. 2013).

Results

Three independent experiments were performed using the TALE-Nuclease targeting the UGPase gene. For each of them, the presence of mutagenic events in the clones obtained three weeks after diatoms transformation was analyzed.

Figure 4:
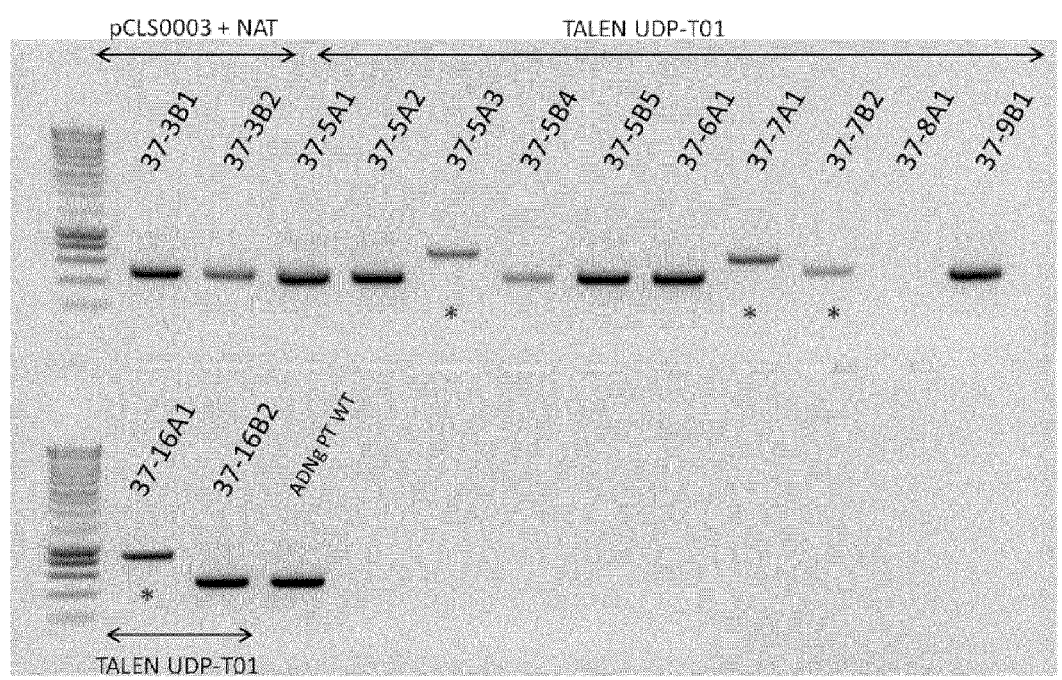
FIG. 4: Molecular characterization of clones from the transformation of the *Phaeodactylum tricornutum* (Pt) strain with the TALE-Nuclease targeting the UGPase gene. Amplification of the UGPase locus by PCR surrounding the TALE-Nuclease cleavage site and migration of the PCR products on agarose gel. Four clones presented a PCR product with a higher size than the one expected (37-5A3, 37-7A1, 37-7B2 and 37-16A1), one clone was not amplified (37-8A1) and 7 presented a PCR band at the expected size as observed in the two clones from the transformation with the empty vector (37-3B1 and 37-3B2).
Figure 5:
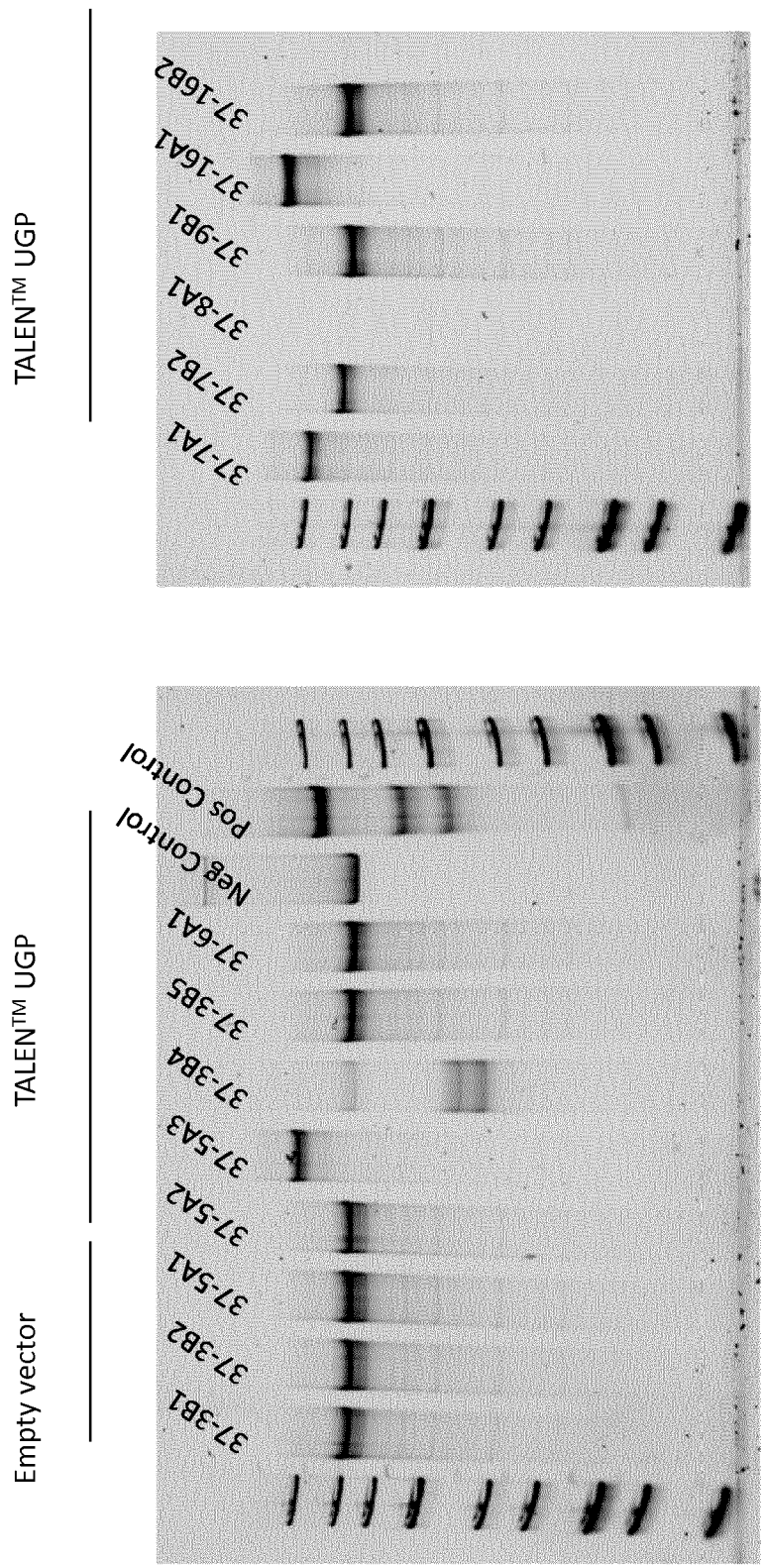
FIG. 5: Molecular characterization of clones from the transformation of the *Phaeodactylum tricornutum* (Pt) strain with the TALE-Nuclease targeting the UGPase gene (experiment 1). T7 assay performed on the 12 clones from the transformation with UGP_TALE-Nuclease and 2 clones from the transformation with the empty vector. The negative control corresponds to a PCR carried out on the clone 37-3B1 (transformed with the empty plasmid), not digested by the T7 enzyme. The T7 positive control corresponds to a PCR product carrying mutagenic events. The clone 37-5B4 is positive for T7 assay.

For the first experiment, 18 clones were obtained in the condition corresponding to diatoms transformed with TALE-Nuclease encoding plasmids (condition 1). Finally, 6 clones resulting from the transformation with the empty vector were obtained (condition 2). The UGPase target amplification was performed on 12 clones obtained in the condition 1 and 2 clones obtained in the condition 2. On the 12 clones tested, 4 present a PCR band higher than expected showing a clear mutagenic event, 1 presents no amplification of the UGPase target, 7 present a band at the wild type size. A T7 assay was assessed on these 12 clones (FIG. 4). One clone among them was positive in T7 assay which reflects the presence of mutagenic events (FIG. 5). As expected no signal was detected in the 2 clones from the condition corresponding to empty vector (condition 2).

For the second experiment, 62 clones were obtained in the condition corresponding to diatoms transformed with TALE-Nuclease encoding plasmids (condition 1). Among them, 36 were tested for the presence of the DNA sequences encoding both TALE-Nuclease monomers. 11/36 (i.e. 30.5%) were positive for both TALE-Nuclease monomers DNA sequences. Finally, 38 clones resulting from the transformation with the empty vector were obtained (condition 2). The UGPase target amplification was performed on 11 clones obtained in the condition 1 and 2 clones obtained in the condition 2. On the 11 clones tested, 5 present no amplification of the UGPase target, 6 present a band at the wild type size (FIG. 6).

In order to identify the nature of the mutagenic event in the 4 clones displaying a higher PCR amplification product from experiment 1 (FIG. 4), we sequenced these fragments. All of them present an insertion of 261 bp (37-5A3), 228 bp (37-7A1), 55 bp (37-7B2) and 330 bp (37-16A1), respectively leading to the presence of stop codon in the coding sequence. The clone 37-3B4 presenting a positive signal for T7 assay was characterized by Deep sequencing. The mutagenesis frequency in this clone was 86% with several type of mutagenic event (either insertion or deletion). An example of mutated sequences is presented in FIG. 7.

Figure 8:
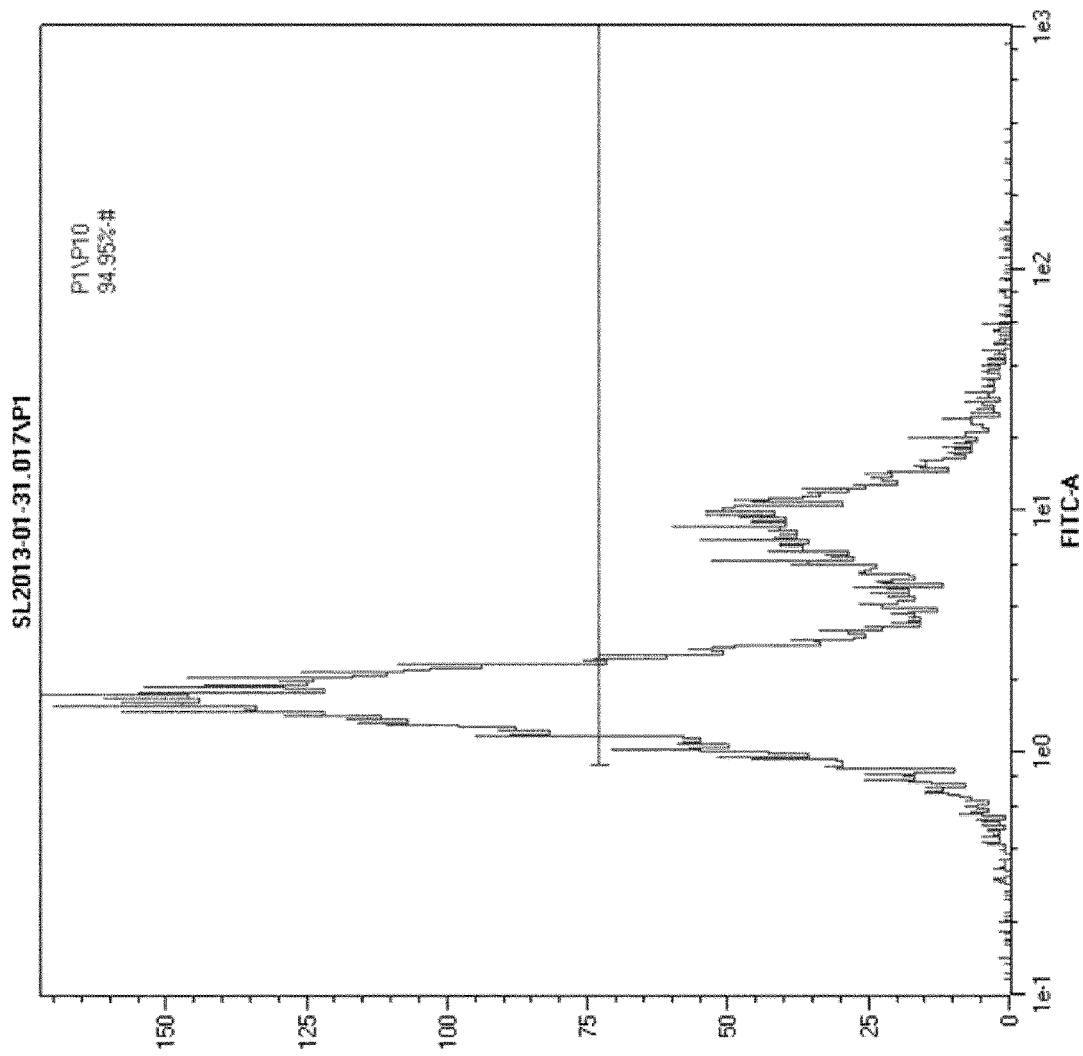
FIG. 8: Molecular characterization of clones from the transformation of the Pt strain with the TALE-Nuclease targeting the UGPase gene. Clone 37-7 A1: 100% mutated on the UGPase gene, clone 37-3B1 from transformation with the empty vector and the Pt wild type strain were labeled with the lipid probe (Bodipy (493/503), Molecular Probe). The fluorescence intensity was measured by flow cytometry. The graphs represent the number of cells function of the fluorescence intensity for 3 independent experiments.
Figure 8:
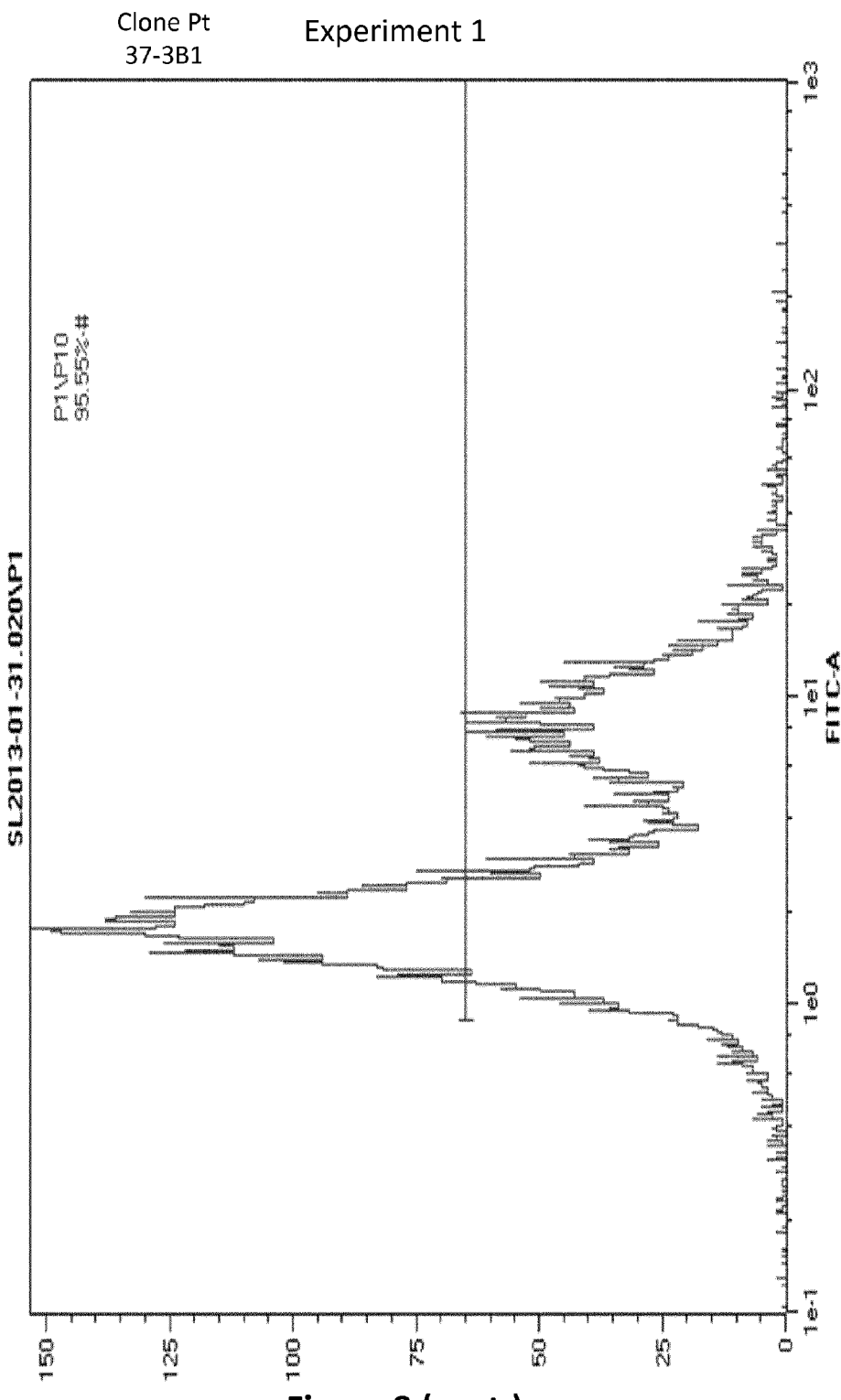
Figure 8:
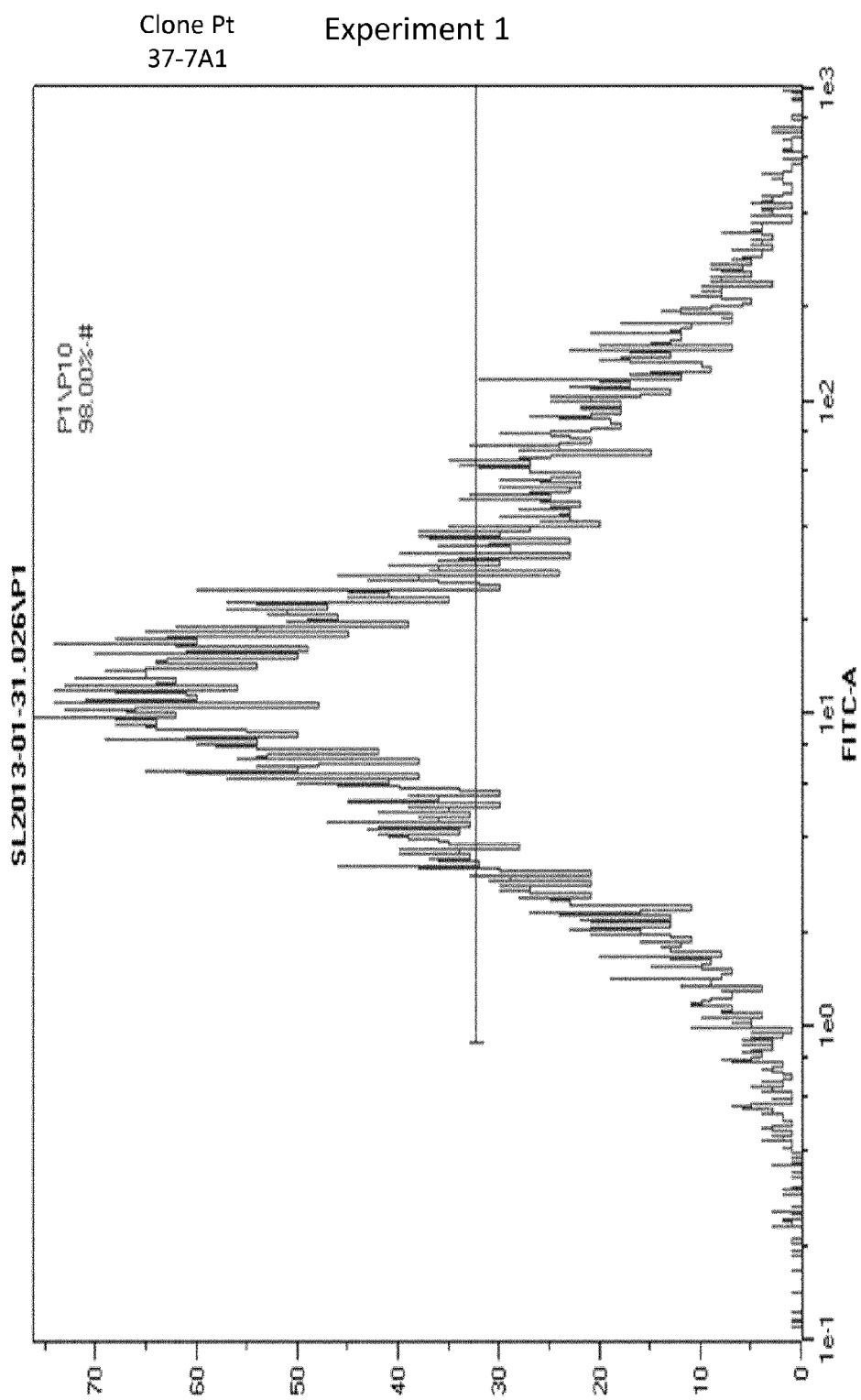
Figure 8:
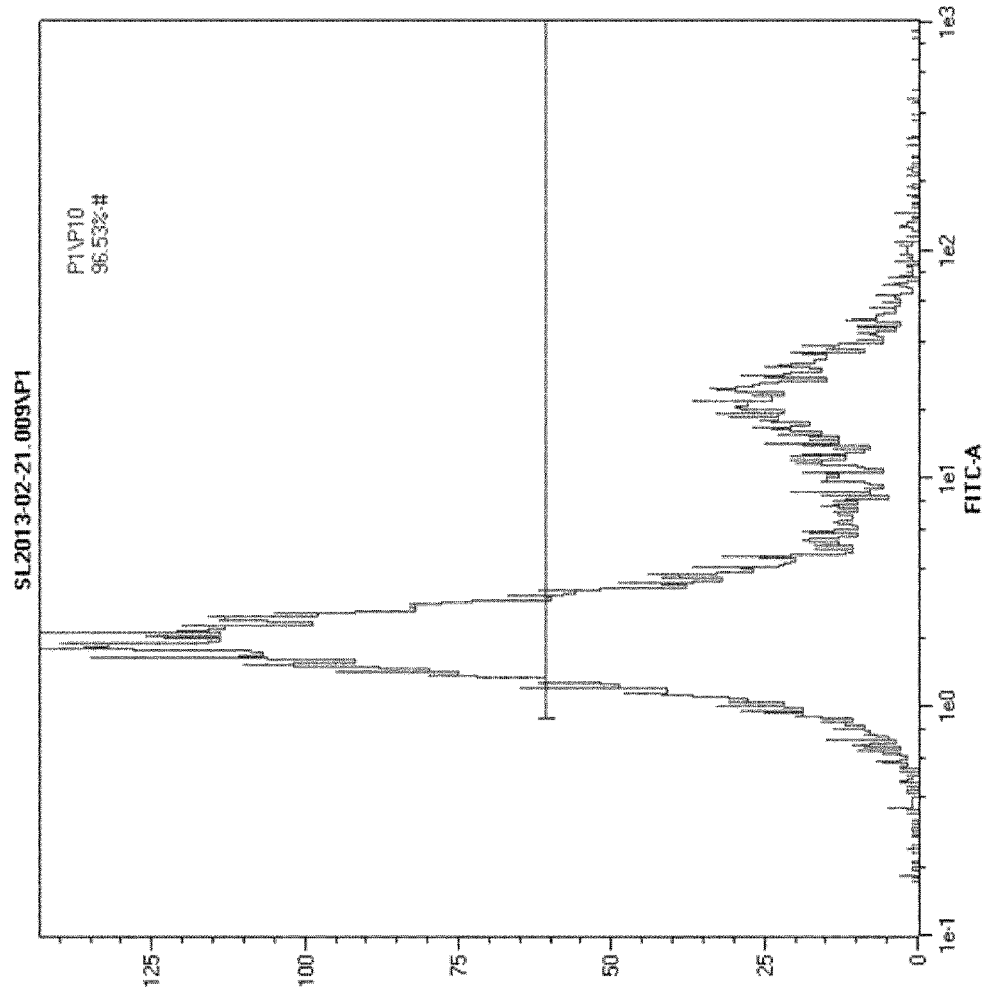
Figure 8:
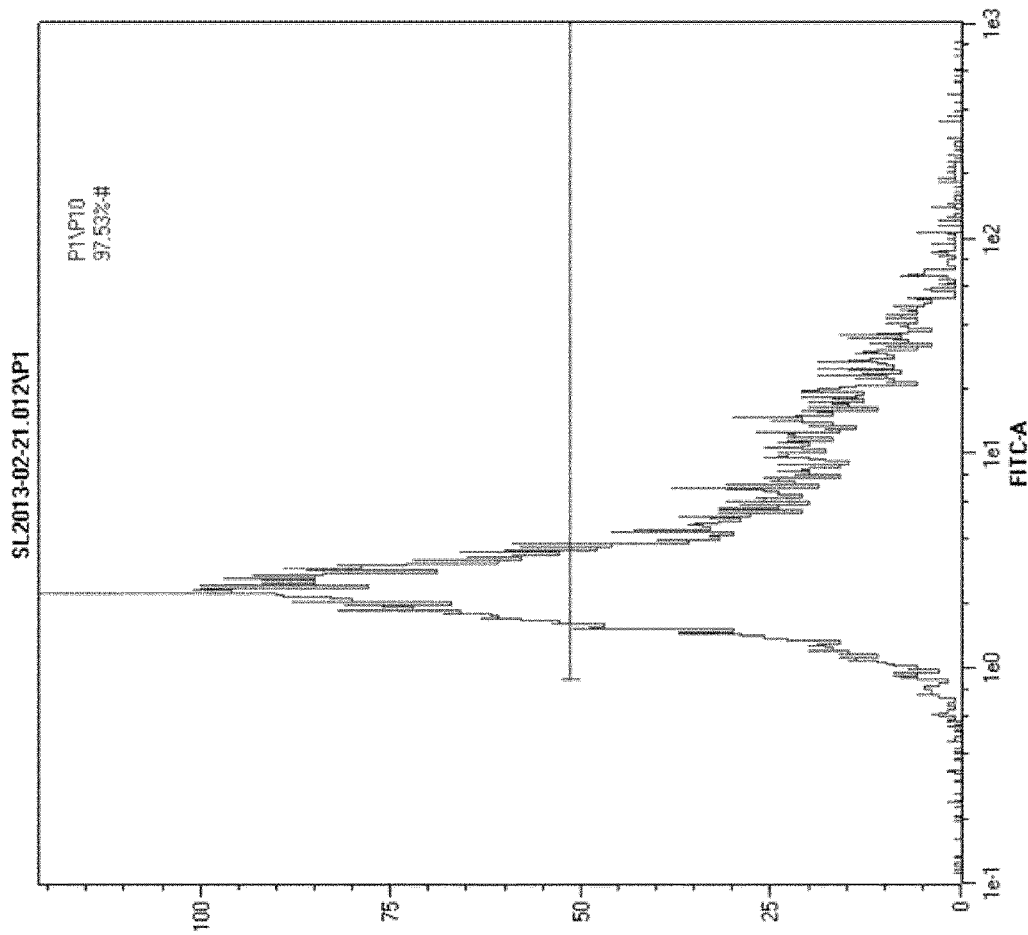
Figure 8:
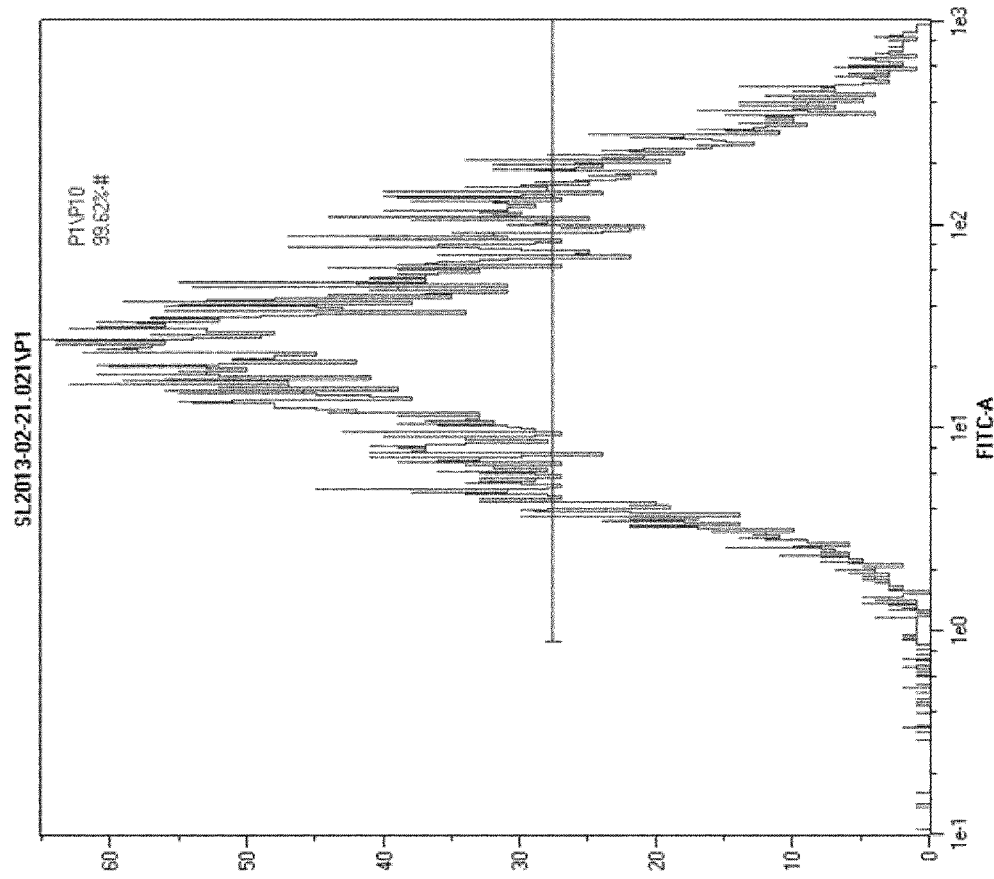
Figure 8:
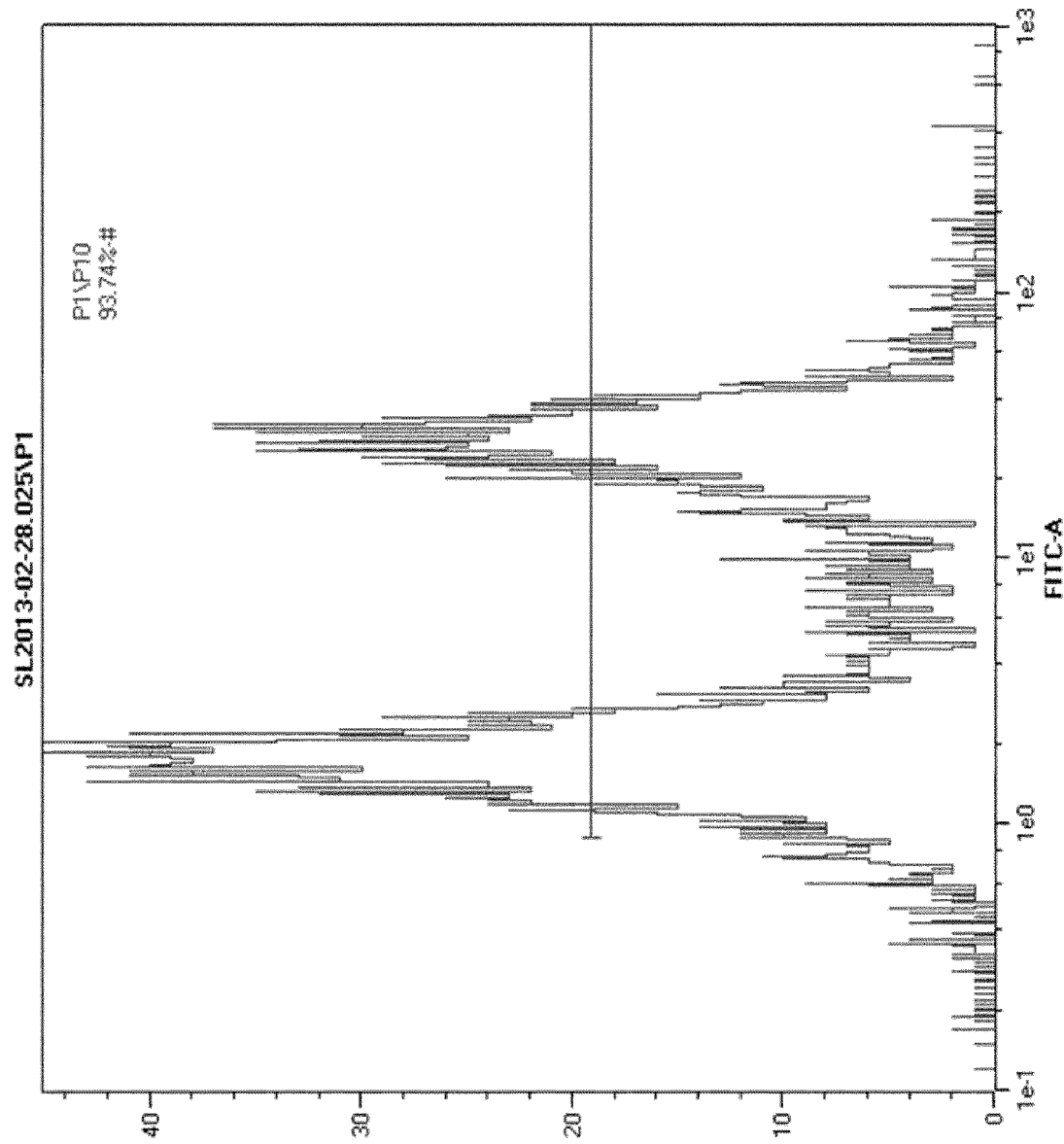
Figure 8:
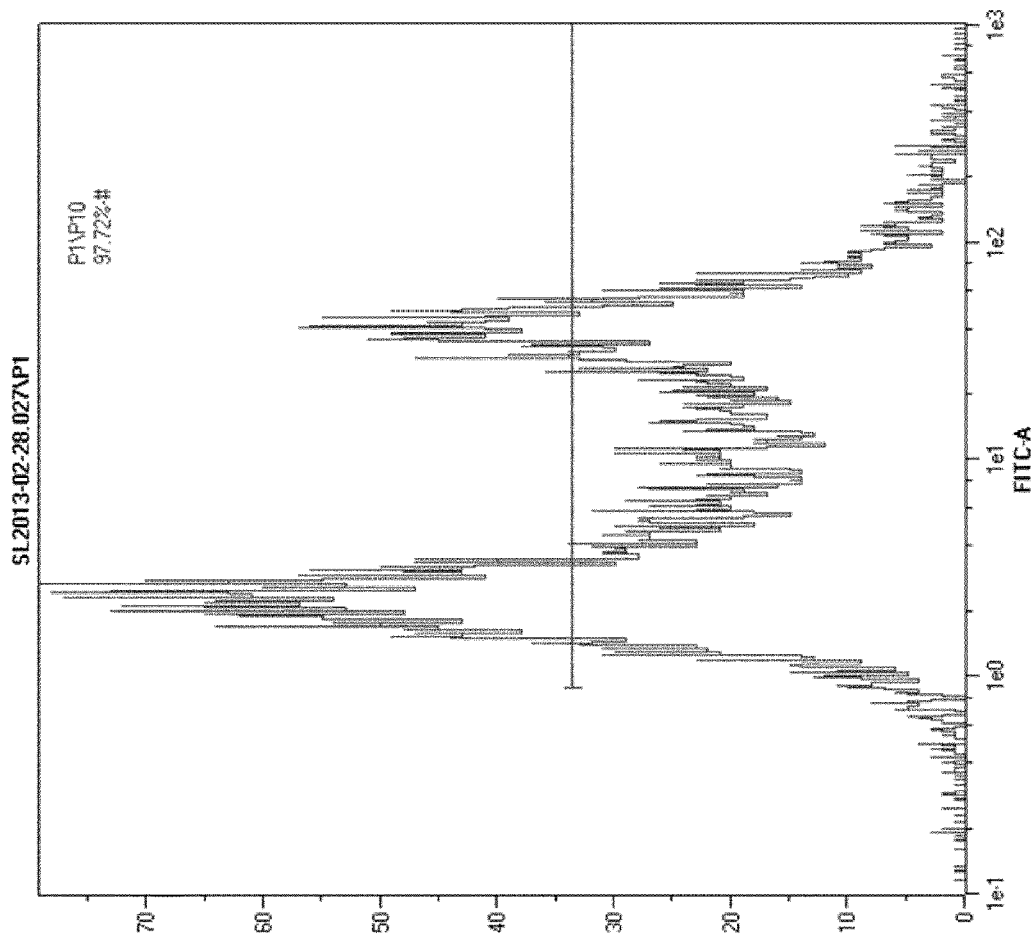
Figure 8:
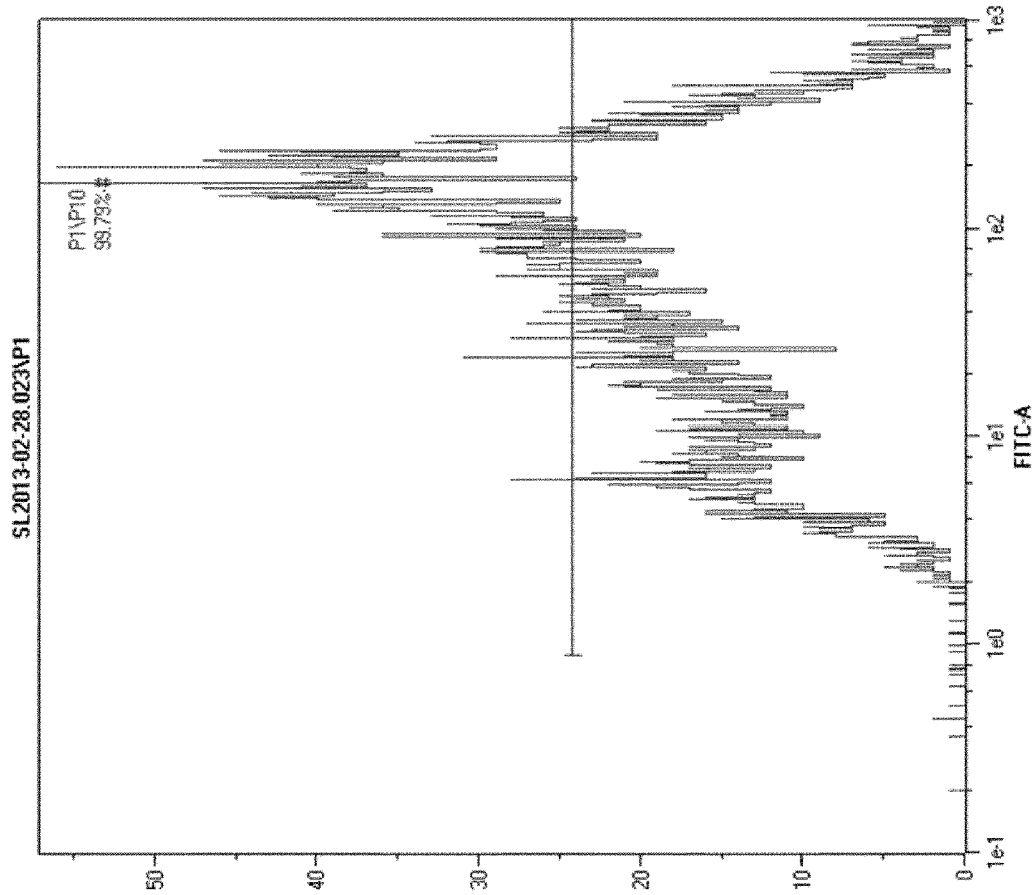

To investigate the impact of UGPase gene inactivation on lipid content, a Bodipy labeling (Molecular Probe) was performed on one clone harboring a mutagenic event in the UGPase target (37-7A1). In parallel, the *Phaeodactylum tricornutum* wild type strain and one clone resulting from the transformation with the empty vector were tested. The results are presented in FIG. 8. We observed an increase of the fluorescence intensity in the clone presenting an inactivation of the UGPase gene compared to the two control strains. This experiment was reproduced 3 times and a shift in the fluorescence intensity was observed at each time. As Bodipy labeling reflects the lipid content of the cells, these results demonstrated a robust and reproducible increase of the lipid content of the mutated strains.

Figure 9:
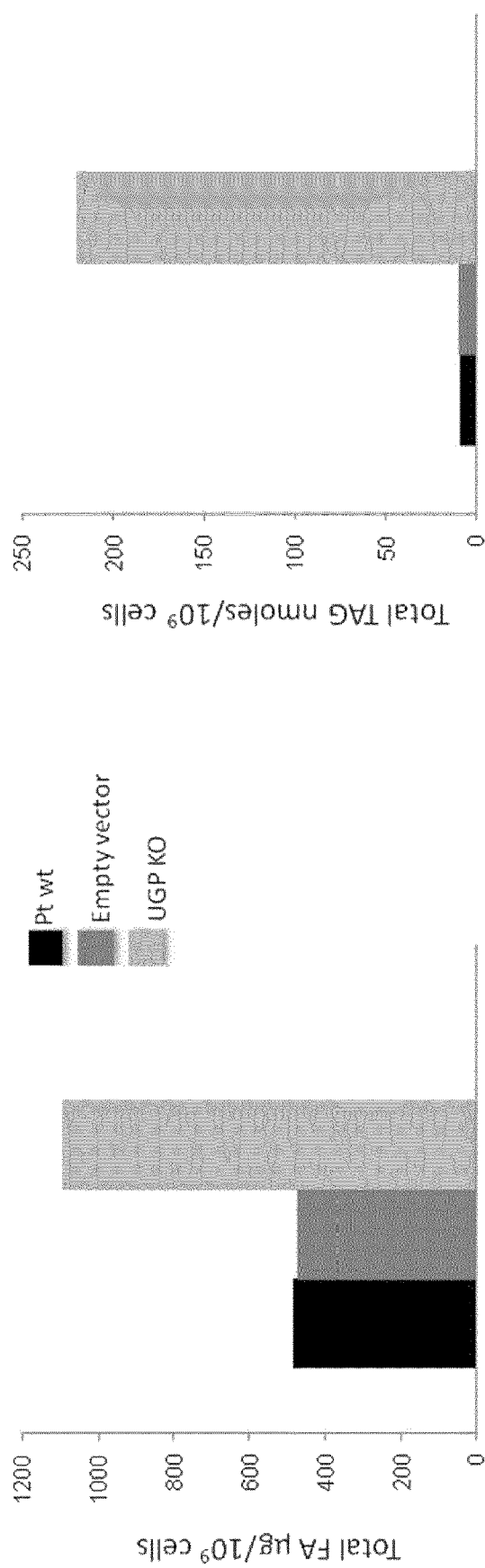
FIG. 9: Quantitative analysis of the fatty acid (FA) and the triacylglycerol (TAG) content in the transgenic diatoms strain corresponding to the mutant UGPase KO (37-7A1) and its associated controls empty vector and Pt wild type.

In order to perform quantitative analysis of the fatty acid (FA) and the triacylglycerol (TAG) content, the wet pellets of diatoms corresponding to the mutants 37-7A1 and its associated controls empty vector and *Phaeodactylum tricornutum* wild type were brought to the APlipid company for an extensive lipidomic analysis. When compared to the controls (Pt-wt parental strain and resistant clone), the mutant 37-7A1 (UGPase) presents a 2 fold increase of its FA content reported to the total number of cells. The content of TAG (in nmoles and reported to the total number of cells) is increased by a factor 24 for the mutant 37-7A1 (FIG. 9).

Thus, a TALE nuclease targeting the UGPase gene induces a reproducible (2 independent experiments), and at high frequency, targeted mutagenesis (up to 100%). Moreover, the inactivation of the UGPase gene leads to a strong and reproducible increase of lipid content in bodipy labeling. The quantification reveals an increase of 2 fold of fatty acid and 24 fold of TAG in the clone UGPase knock out compare to controls.

Example 2: Targeted Mutagenesis Induced by a TALE-Nuclease Targeting a Putative Elongase Gene In order to determine the impact of the putative elongase gene (SEQ ID NO: 14) inactivation on lipid content in diatoms, one engineered TALE-Nuclease, called elongase_TALE-Nuclease encoded by the pCLS19746 (SEQ ID NO: 15) and pCLS19750 (SEQ ID NO: 16) plasmids designed to cleave the DNA sequence 5'-TCTTTTC-CCTCGTCGGCatgctccggaccttCCCCAGCTTGTACA-CAA-3' (SEQ ID NO: 17) was used. Although this TALE-nuclease targets a sequence coding a protein with unknown function, this target presents 86% of sequence identity with the mRNA of the fatty acid elongase 6 (ELOVL6) in *Taeniopygia guttata*, and 86% of sequence identity with the elongation of very long chain fatty acids protein 6-like (LOC100542840) in *meleagris gallopavo*.

These TALE-Nuclease encoding plasmids were co-transformed with a plasmid conferring resistance to nourseothricin (NAT) in a wild type diatom strain. The individual clones resulting from the transformation were screened for the presence of mutagenic events which lead to elongase gene inactivation.

Materials and Methods

*Phaeodactylum tricornutum* Bohlin clone CCMP2561 was grown and transformed according to the methods described in example 1 with M17 tungstene particles (1.1 µm diameter, BioRad) coated with 9 µg of a total amount of DNA composed of 1.5 µg of each monomer of TALE-Nucleases (pCLS19746 (SEQ ID NO: 15) and pCLS19750 (SEQ ID NO: 16), 3 µg of the NAT selection plasmid (pCLS16604) (SEQ ID NO: 1) and 3 µg of an empty vector (pCLS0003) (SEQ ID NO: 2) using 1.25M CaCl2 and 20 mM spermidin according to the manufacturer's instructions.

Characterization

A-Colony Screening

After selection, resistant colonies were picked and dissociated according to the method described in example 1. Supernatants were used were used for each PCR reaction. Specific primers for TALE-Nuclease screens: TALE-Nuclease_For 5'-AATCTCGCCTATTCATGGTG-3' (SEQ ID NO: 7) and HA_Rev 5'-TAATCTGGAACATCGTATGGG-3' (SEQ ID NO: 8). TALE-Nuclease_For 5'-AATCTCGCCT-ATTCATGGTG-3' (SEQ ID NO: 7) and S-Tag_Rev 5'-TGTCTCTCGAACTTGGCAGCG-3' (SEQ ID NO: 9).

B-Identification of Mutagenic Event

The elongase target was amplified using a 1:5 dilution of the lysis colony with sequence specific primers flanked by adaptators needed for HTS sequencing on the 454 sequencing system (454 Life Sciences) and the two following primers: elongase_For 5'-CCATCTCATCCCTGCGT-GTCTCCGACTCAG-Tag-AAGCGCATCCGTTGGTTCC-3' (SEQ ID NO: 18) and elongase_Rev 5'-CCTATCCCCT-GTGTGCCTTGGCAGTCTCAG TCAATGAGTTCACTGGAAAGGG-3' (SEQ ID NO: 19).

The PCR products were purified on magnetic beads (Agencourt AMPure XP, Beckman Coulter) and quantified with a NanoDrop 1000 spectrophotometer (Thermo Scientifioc). 50 ng of the amplicons were denatured and then annealed in 10 µl of annealing buffer (10 mM Tris-HCl pH8, 100 mM NaCl, 1 mM EDTA) using an Eppendorf Master-Cycle gradient PCR machine. The annealing program is as follows: 95° C. for 10 min; fast cooling to 85° C. at 3° C./sec; and slow cooling to 25° C. at 0.3° C./sec. The totality of the annealed DNA was digested for 15 min at 37° C. with 0.5 µl of the T7 Endonuclease I (10 U/µl) (M0302 Biolabs) in a final volume of 20 µl (1×NEB buffer 2, Biolabs). 10 µl of the digestion were then loaded on a 10% polyacrylamide MiniProtean TBE precast gel (BioRad). After migration the gel was stained with SYBRgreen and scanned on a Gel Doc XR+ apparatus (BioRad).

C-Measure of the Mutagenesis Frequency by Deep Sequencing

The elongase target was amplified with sequence specific primers flanked by adaptators needed for HTS sequencing on the 454 sequencing system (454 Life Sciences) using the primer Delta 6 elongase_For 5'-AAGCGCATCCGTTGGT-TCC-3' (SEQ ID NO: 20) and Delta 6 elongase_Rev 5'-TCAATGAGTTCACTGGAAAGGG-3' (SEQ ID NO: 21). 5000 to 10 000 sequences per sample were analyzed.

D-Lipid Content Analysis

The lipid content analysis was performed by the APLILIPID company (Applied Lipidomics Investigation) using protocol previously described in (Vieler, Wilhelm et al. 2007; Lamaziere, Wolf et al. 2012; Lamaziere, Wolf et al. 2013).

Results

Three weeks after the transformation of the diatoms, 62 clones were obtained in the condition corresponding to the transformation performed with the TALE-Nuclease encoding plasmids (condition 1). Among them, 35 were tested for the presence of both TALE-Nuclease monomers DNA sequences. 11/27 (i.e. 40.7%) were positive for both TALE-Nuclease monomers DNA sequences. Finally, 38 clones resulting from the transformation with the empty vector were obtained (condition 2).

Figure 10:
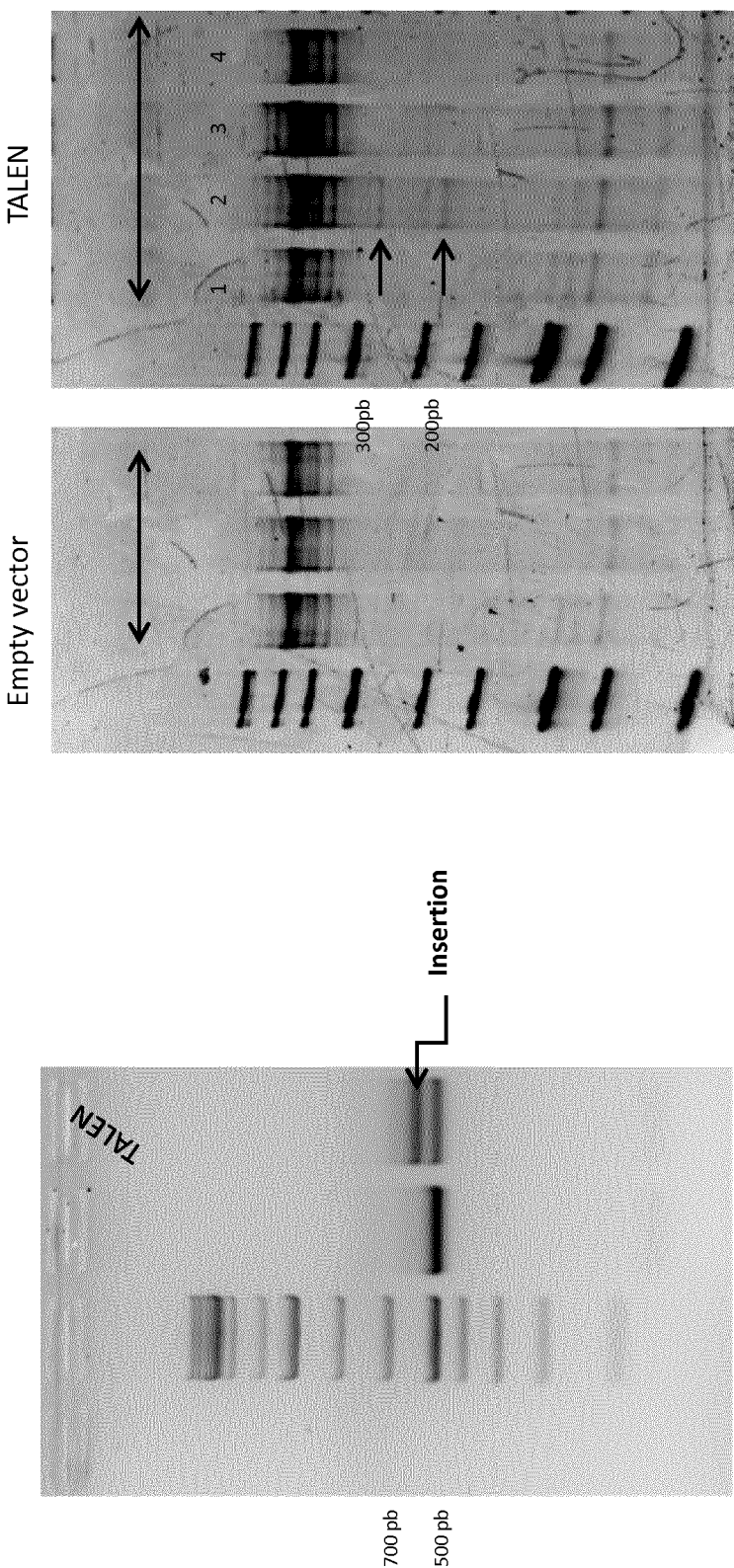
FIG. 10: Mutagenesis induced by the TALE-Nuclease targeting the putative elongase gene. A PCR surrounding the putative elongase specific target was performed. In the left panel, the clone presenting in equal proportions a PCR band at the expected size and another one with a higher size discloses a clear mutagenic event. A T7 assay was assessed on 4 clones resulting from the transformation with the elongase TALE-Nuclease and on 3 clones resulting from the transformation with the empty vector. The clone 2 is positive for the T7 assay.

The 11 clones, positive for both TALE-Nuclease monomers DNA sequences were tested with the T7 assay. The *Phaeodactylum tricornutum* wild type strain, as well as four clones resulting from the transformation with the empty vector, were tested in parallel. Four clones presented no amplification. Because the amplification of another locus is possible, the quality of the lysates is not questioned. So the absence of amplification could suggest the presence of a large mutagenic event at the elongase locus. One clone showed in equal proportions a PCR product at the expected size and another one with a higher weight, actually demonstrating a clear mutagenic event (FIG. 10). One clone was positive in the T7 assay, which reflects the presence of mutagenic events and 9 clones presented no signal in the T7 assay. As expected no signal was detected in the condition corresponding to the empty vector or the *Phaeodactylum tricornutum* wild type strain.

In order to identify the nature of the mutagenic event in the clone displaying a higher PCR amplification product, we sequenced this fragment. An insertion of 83 bp was detected leading to presence of stop codon in the coding sequence. The clone presenting a positive T7 signal was characterized by Deep sequencing. The mutagenesis frequency in this clone was 5.9% with one type of mutation (deletion of 22 bp). An example of mutated sequences is presented in FIG. 11.

Figure 12:
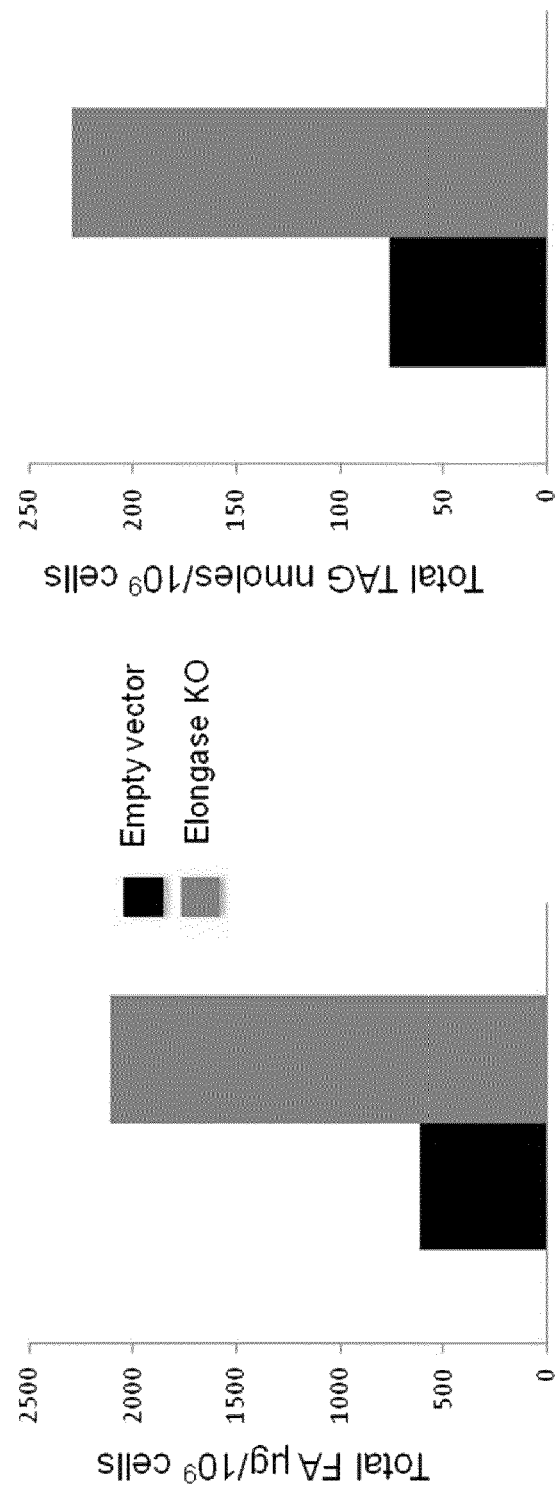
FIG. 12: Quantitative analysis of the fatty acid (FA) and the triacylglycerol (TAG) content in the transgenic diatoms strain corresponding to the mutant Elongase and its associated control empty vector.

In order to perform quantitative analysis of the fatty acid (FA) and the triacylglycerol (TAG) content, the wet pellets of diatoms corresponding to the mutant and its associated control empty vector, were brought to the APlipid company for an extensive lipidomic analysis. When compared to the control (resistant clone), the mutant (Elongase) presents a 3 fold increase of its FA content reported to the total number of cells. The content of TAG (in nmoles and reported to the total number of cells) is increased by a factor 3 for the mutant elongase (FIG. 12).

Thus, a TALE nuclease targeting the Elongase gene induces a high frequency of targeted mutagenesis (up to 50%). To investigate the impact of Elongase gene inactivation on lipid profile, the sub-cloning of the clone with 50% of mutated event will be done. The quantification of lipid content in this clone reveals an increase of 3 fold of fatty acid and 3 fold of TAG in the clone Elongase mutant compare to control.

Example 3: Targeted Mutagenesis Induced by a TALE-Nuclease Targeting the G3PDH Gene In order to determine the impact of the Glycerol-3 Phosphate deshydrogenase (G3PDH) gene (SEQ ID NO: 22) inactivation on lipid content in diatoms, one engineered TALE-Nuclease, called G3PDH_TALE-Nuclease encoded by the pCLS23159 (SEQ ID NO: 23) and pCLS23163 (SEQ ID NO: 24) plasmids designed to cleave the DNA sequence 5'-TTCTGACCAACTCGATAAAGTATGCATCATCGG-TAGCGGTAACTGGGGAA-3' (SEQ ID NO: 25) was used. These TALE-Nuclease encoding plasmids were co-transformed with a plasmid conferring resistance to nourseothricin (NAT) in a wild type diatom strain. The individual clones resulting from the transformation were screened for the presence of mutagenic events which lead to G3PDH gene inactivation.

Materials and Methods

*Phaeodactylum tricornutum* Bohlin clone CCMP2561 was grown and transformed according to the methods described in example 1 with M17 tungstene particles (1.1 μm diameter, BioRad) coated with 9 μg of a total amount of DNA composed of 3 μg of each monomer of TALE-Nucleases (pCLS23159 (SEQ ID NO: 23) and pCLS23163 (SEQ ID NO: 24)), 3 μg of the NAT selection plasmid (pCLS16604) (SEQ ID NO: 1) and 3 μg of an empty vector (pCLS0003) (SEQ ID NO: 2) using 1.25M CaCl2 and 20 mM spermidin according to the manufacturer's instructions. As negative control, beads were coated with a DNA mixture containing 3 μg of the NAT selection plasmid (pCLS16604) and 6 μg of an empty vector (pCLS0003) (SEQ ID NO: 2). Agar plates with the diatoms to be transformed were positioned at 7.5 cm from the stopping screen within the bombardment chamber (target shelf on position two). A burst pressure of 1550 psi and a vacuum of 25 Hg/in were used. After bombardment, plates were incubated for 48 hours with a 12 h light: 12 h dark photoperiod.

Characterization

A-Colony Screening

After selection, resistant colonies were picked and dissociated according to the methods described in example 1. Supernatants were used for each PCR reaction. Specific primers for TALE-Nuclease screens: TALE-Nuclease_For 5'-AATCTCGCCTATTCATGGTG-3' (SEQ ID NO: 7) and Stag_Rev 5'-TGTCTCTCGAACTTGGCAGCG-3' (SEQ ID NO: 9). HA_For 5'-ACCCATACGATGTTCCAGAT-TACGCT-3' (SEQ ID NO: 26) and TALE-Nuclease_Rev 5'-AATCTTGAGAAGTTGGCCTGTGTC-3' (SEQ ID NO: 27).

B-Identification of Mutagenic Event by Deep Sequencing

The G3PDH target was amplified using a 1:5 dilution of the lysis colony with sequence specific primers flanked by adaptators needed for HTS sequencing on the 454 sequencing system (454 Life Sciences) and the two following primers: G3PDH_For 5'-CCATCTCATCCCTGCGT-GTCTCCGACTCAG-Tag-TCTGCTACTGCTCATCCG-CACC-3' (SEQ ID NO: 28) and G3PDH_Rev 5'-CCTATC-CCCTGTGTGCCTTGGCAGTCTCAG-TCGCGACAGGCTTCTGCTAGATC-3' (SEQ ID NO: 29). 5000 to 10 000 sequences per sample were analyzed.

E-Lipid Content Analysis

The lipid content analysis was performed by the APLILIPID company (Applied Lipidomics Investigation) using protocol previously described in (Vieler, Wilhelm et al. 2007; Lamaziere, Wolf et al. 2012; Lamaziere, Wolf et al. 2013).

Results

Figure 13:
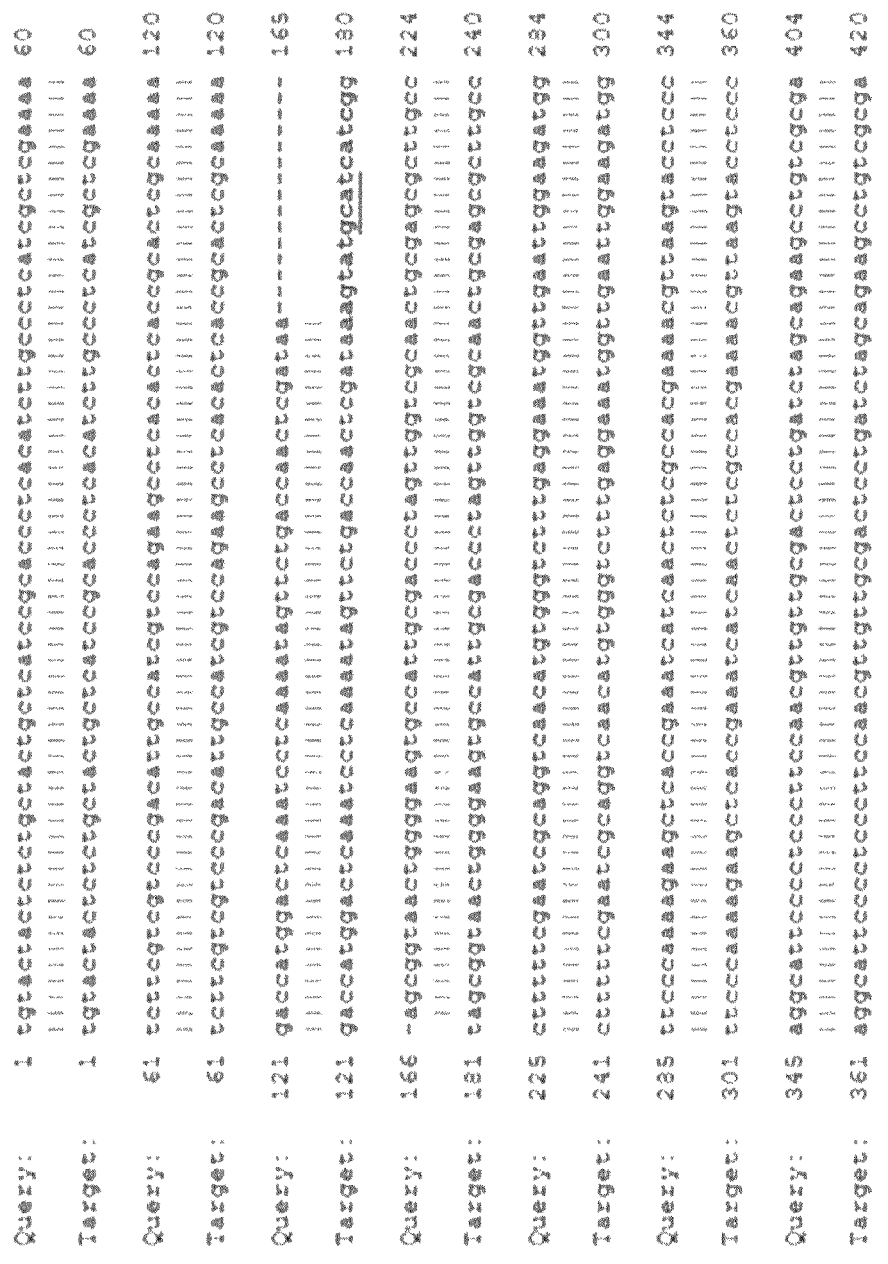

Three weeks after the transformation of the diatoms, 13 clones were obtained in the condition corresponding to the transformation performed with the TALE-Nuclease encoding plasmids (condition 1). Among them, 7 were tested for the presence of both TALE-Nuclease monomers DNA sequences. 7/13 (i.e. 53.8%) were positive for both TALE-Nuclease monomers DNA sequences. Among them, one present 33% of frequency of targeted mutagenesis at the recognition TALE-Nuclease site. An example of mutated sequences is presented in FIG. 13. As expected no signal was detected in the condition corresponding to the empty vector or the *Phaeodactylum tricornutum* wild type strain.

Thus, a TALE nuclease targeting the G3PDH gene induces a high frequency of targeted mutagenesis (up to 33%).

Example 4: Targeted Mutagenesis Induced by a TALE-Nuclease Targeting the Omega3 Desaturase Gene In order to determine the impact of the Omega 3 desaturase gene (SEQ ID NO: 30) inactivation on lipid content in diatoms, one engineered TALE-Nuclease, called Omega3 desaturase_TALE-Nuclease encoded by the pCLS23158 (SEQ ID NO: 31) and pCLS23162 (SEQ ID NO: 32) plasmids designed to cleave the DNA sequence 5'-TTTTC-CACAACACTGTTAATGCCTTTTCGTTGCGCATAC-CGAGTACCCA-3' (SEQ ID NO: 33) was used. These TALE-Nuclease encoding plasmids were co-transformed with a plasmid conferring resistance to nourseothricin (NAT) in a wild type diatom strain. The individual clones resulting from the transformation were screened for the presence of mutagenic events which lead to Omega3 desaturase gene inactivation.

Materials and Methods

*Phaeodactylum tricornutum* Bohlin clone CCMP2561 was grown and transformed according to the method described in example 1, with M17 tungstene particles (1.1 μm diameter, BioRad) coated with 9 μg of a total amount of DNA composed of 1.5 μg of each monomer of TALE-Nucleases (pCLS23158 (SEQ ID NO: 31) and pCLS23162 (SEQ ID NO: 32)), 3 μg of the NAT selection plasmid (pCLS16604) (SEQ ID NO: 1) and 3 μg of an empty vector (pCLS0003) (SEQ ID NO: 2) using 1.25M CaCl2 and 20 mM spermidin according to the manufacturer's instructions. As negative control, beads were coated with a DNA mixture containing 3 μg of the NAT selection plasmid (pCLS16604) and 6 μg of an empty vector (pCLS0003) (SEQ ID NO: 2).

Characterization

A-Colony Screening

After selection, resistant colonies were picked and dissociated according to the method described in example 1. Supernatants were used for each PCR reaction. Specific primers for TALE-Nuclease screens: TALE-Nuclease_For 5'-AATCTCGCCTATTCATGGTG-3' (SEQ ID NO: 7) and Stag_Rev 5'-TGTCTCTCGAACTTGGCAGCG-3' (SEQ ID NO: 9). HA_For 5'-ACCCATACGATGTTCCAGATTACGCT-3' (SEQ ID NO: 26) and TALE-Nuclease_Rev 5'-AATCTTGAGAAGTTGGCCTGTGTC-3' (SEQ ID NO: 27).

B-Identification of Mutagenic Event by Deep Sequencing

The Omega3 desaturase target was amplified using a 1:5 dilution of the lysis colony with sequence specific primers flanked by adaptators needed for HTS sequencing on the 454 sequencing system (454 Life Sciences) and the two following primers: Omega3 desaturase_For 5'-CCATCTCATCCTGCGTGTCTCCGACTCAG-Tag-GCGTGTGCTCACCTGTTGTCC-3' (SEQ ID NO: 34) and Omega3 desaturase_Rev 5'-CCTATCCCCTGTGTGCCTTGGCAGTCTCAG-AAGCATGCGCTTCACTTCGCTC-3' (SEQ ID NO: 35). 5000 to 10 000 sequences per sample were analyzed.

Results

Three weeks after the transformation of the diatoms, 9 clones were obtained in the condition corresponding to the transformation performed with the TALE-Nuclease encoding plasmids (condition 1). Among them, 6 were tested for the presence of both TALE-Nuclease monomers DNA sequences. 6/9 (i.e. 66%) were positive for both TALE-Nuclease monomers DNA sequences. The targeted mutagenesis frequency was determined by Deep sequencing on 3 out of the 6 clones. All of them present a high frequency of mutagenic event at the TALE-Nuclease recognition site: 14; 70 and 90%. An example of mutated sequences is presented in FIG. 14. As expected no signal was detected in the condition corresponding to the empty vector or the *Phaeodactylum tricornutum* wild type strain.

Thus, a TALE nuclease targeting the Omega3 desaturase gene induces a high frequency of targeted mutagenesis (up to 90%).

Example 5: Targeted Mutagenesis Induced by a TALE-Nuclease Targeting the Putative Palmitoyl Protein Thioesterase Gene (PPT)

In order to determine the impact of the PPT gene (SEQ ID NO: 36) inactivation on lipid content in diatoms, one engineered TALE-Nuclease, called PPT_TALE-Nuclease encoded by the pCLS19744 (SEQ ID NO: 37) and pCLS19748 (SEQ ID NO: 38) plasmids designed to cleave the DNA sequence 5'-TGGTCTTTGCCATGGGATGGGAGATTCGTGCTTTAATTCTGGCATGCAA-3' (SEQ ID NO: 39) was used. These TALE-Nuclease encoding plasmids were co-transformed with a plasmid conferring resistance to nourseothricin (NAT) in a wild type diatom strain. The individual clones resulting from the transformation were screened for the presence of mutagenic events which lead to PPT gene inactivation.

Materials and Methods

*Phaeodactylum tricornutum* Bohlin clone CCMP2561 was grown and transformed according to the method described in example 1, with M17 tungstene particles (1.1 µm diameter, BioRad) coated with 9 µg of a total amount of DNA composed of 1.5 µg of each monomer of TALE-Nucleases (pCLS19744 (SEQ ID NO: 37) and pCLS19748 (SEQ ID NO: 38)), 3 µg of the NAT selection plasmid (pCLS16604) (SEQ ID NO: 1) and 3 µg of an empty vector (pCLS0003) (SEQ ID NO: 2) using 1.25M CaCl2 and 20 mM spermidin according to the manufacturer's instructions. As negative control, beads were coated with a DNA mixture containing 3 µg of the NAT selection plasmid (pCLS16604) and 6 µg of an empty vector (pCLS0003) (SEQ ID NO: 2).

Characterization

A-Colony Screening

After selection, resistant colonies were picked and dissociated according to the method described in example 1. Supernatants were used for each PCR reaction. Specific primers for TALE-Nuclease screens: TALE-Nuclease_For 5'-AATCTCGCCTATTCATGGTG-3' (SEQ ID NO: 7) and Stag_Rev 5'-TGTCTCTCGAACTTGGCAGCG-3' (SEQ ID NO: 9). HA_For 5'-ACCCATACGATGTTCCAGATTACGCT-3' (SEQ ID NO: 26) and TALE-Nuclease_Rev 5'-AATCTTGAGAAGTTGGCCTGTGTC-3' (SEQ ID NO: 27).

B-Identification of Mutagenic Event by Deep Sequencing

The PPT target was amplified using a 1:5 dilution of the lysis colony with sequence specific primers flanked by adaptators needed for HTS sequencing on the 454 sequencing system (454 Life Sciences) and the two following primers: PPT_ For 5'-CCATCTCATCCCTGCGTGTCTCCGACTCAG-Tag-GAAGAACAGTCGCACCTGGTGC-3' (SEQ ID NO: 40) and PPT_Rev 5'-CCTATCCCCTGTGTGCCTTGGCAGTCTCAG-TCCGCCCTAACACCTTCCGC-3' (SEQ ID NO: 41). 5000 to 10 000 sequences per sample were analyzed.

Results

Three weeks after the transformation of the diatoms, 11 clones were obtained in the condition corresponding to the transformation performed with the TALE-Nuclease encoding plasmids (condition 1). Among them 3/11 (i.e. 27.3%) were positive for both TALE-Nuclease monomers DNA sequences. The targeted mutagenesis frequency was determined by Deep sequencing on 1 out of the 3 clones. This clone presents a high frequency of mutagenic event at the TALE-Nuclease recognition site: 22%. An example of mutated sequences is presented in FIG. 15. As expected no signal was detected in the condition corresponding to the empty vector or the *Phaeodactylum tricornutum* wild type strain.

Thus, a TALE nuclease targeting the PPT gene induces a high frequency of targeted mutagenesis (up to 22%).

Example 6: Targeted Mutagenesis Induced by a TALE-Nuclease Targeting the Enoyl ACP Reductase Gene In order to determine the impact of the Enoyl ACP reductase gene (SEQ ID NO: 42) inactivation on lipid content in diatoms, one engineered TALE-Nuclease, called Enoyl_ACP_Reductase_TALE-Nuclease encoded by the pCLS23157 (SEQ ID NO: 43) and pCLS23161 (SEQ ID NO: 44) plasmids designed to cleave the DNA sequence 5'—TGTTGCCGATTCCACTGGTTACGGCTGGGCGATCGCCAAAGCTTTGGCCGAAGCAGGA-3' (SEQ ID NO: 45) was used. These TALE-Nuclease encoding plasmids were co-transformed with a plasmid conferring resistance to nourseothricin (NAT) in a wild type diatom strain. The individual clones resulting from the transformation were screened for the presence of mutagenic events which lead to Enoyl ACP reductase gene inactivation.

Materials and Methods

*Phaeodactylum tricornutum* Bohlin clone CCMP2561 was grown and transformed according to the method described in example 1, with M17 tungstene particles (1.1 µm diameter, BioRad) coated with 9 µg of a total amount of DNA composed of 1.5 µg of each monomer of TALE-Nucleases (pCLS23157 (SEQ ID NO: 43) and pCLS23161 (SEQ ID NO: 44), 3 µg of the NAT selection plasmid (pCLS16604) (SEQ ID NO: 1) and 3 µg of an empty vector (pCLS0003) (SEQ ID NO: 2) using 1.25M CaCl2 and 20 mM spermidin according to the manufacturer's instructions. As negative control, beads were coated with a DNA mixture containing 3 µg of the NAT selection plasmid (pCLS16604) and 6 µg of an empty vector (pCLS0003) (SEQ ID NO: 2).

Characterization

A-Colony Screening

After selection, resistant colonies were picked and dissociated according to the method described in example 1. Supernatants were used for each PCR reaction. Specific primers for TALE-Nuclease screens: TALE-Nuclease_For 5'-AATCTCGCCTATTCATGGTG-3' (SEQ ID NO: 7) and Stag_Rev 5'-TGTCTCTCGAACTTGGCAGCG-3' (SEQ ID NO: 9). HA_For 5'-ACCCATACGATGTTCCAGAT-TACGCT-3' (SEQ ID NO: 26) and TALE-Nuclease_Rev 5'-AATCTTGAGAAGTTGGCCTGTGTC-3' (SEQ ID NO: 27).

B-Identification of Mutagenic Event by Deep Sequencing

The Enoyl ACP reductase target was amplified using a 1:5 dilution of the lysis colony with sequence specific primers flanked by adaptators needed for HTS sequencing on the 454 sequencing system (454 Life Sciences) and the two following primers: Enoyl ACP reductase _For 5'-CCATCTCATC-CCTGCGTGTCTCCGACTCAG-Tag-GGACTGTTTCGC-TACGGTACATC-3' (SEQ ID NO: 46) and Enoyl ACP reductase_Rev 5'-CCTATCCCCTGTGTGCCTTGGCA-GTCTCAG-GAAATGGTGTATCCGTCCAATCC-3' (SEQ ID NO: 47). 5000 to 10 000 sequences per sample were analyzed.

Results

Figure 16:
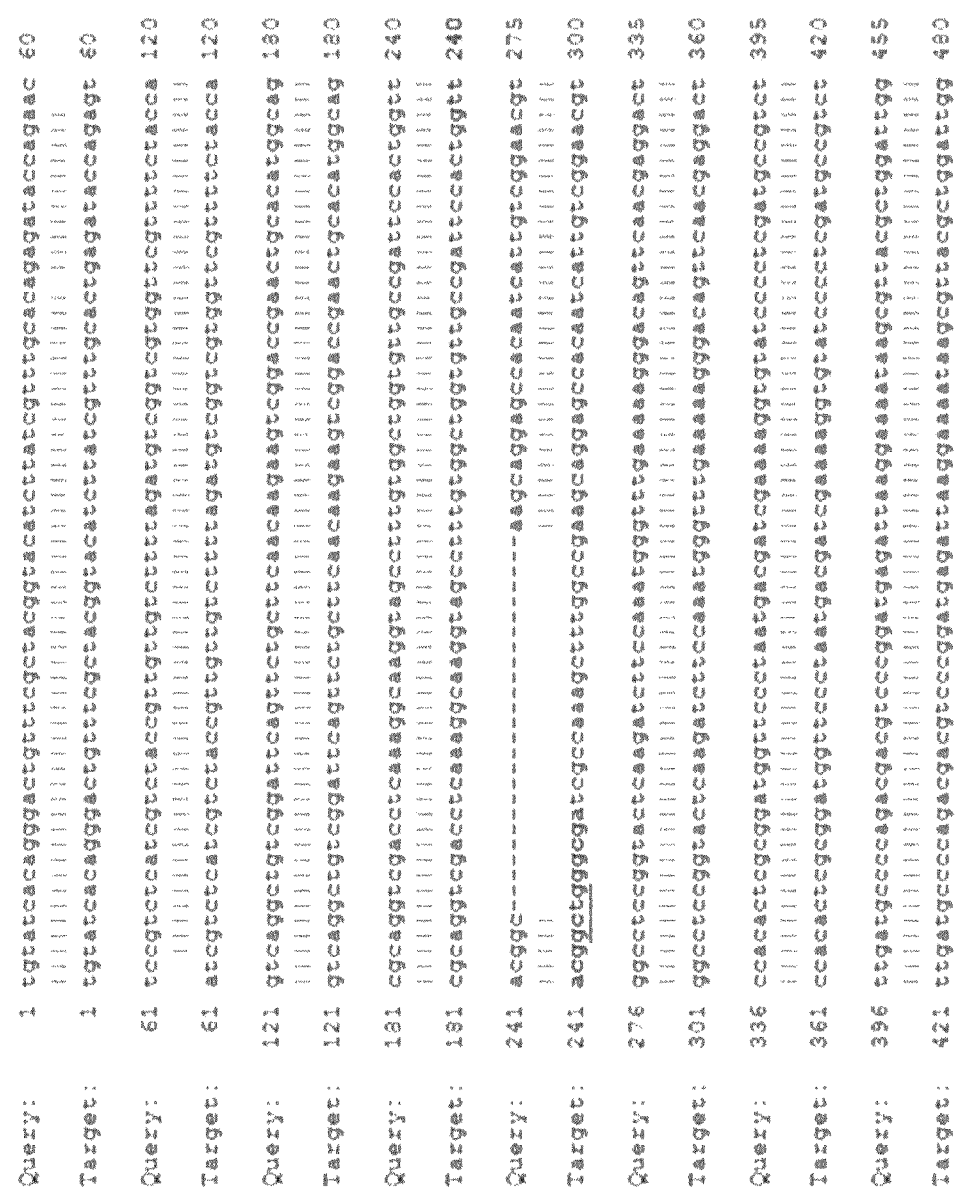

Three weeks after the transformation of the diatoms, 14 clones were obtained in the condition corresponding to the transformation performed with the TALE-Nuclease encoding plasmids (condition 1). Among them 2/14 (i.e. 14%) were positive for both TALE-Nuclease monomers DNA sequences. The targeted mutagenesis frequency was determined by Deep sequencing on 1 out of the 2 clones. This clone presents a frequency of mutagenic event at the TALE-Nuclease recognition site: 12%. An example of mutated sequences is presented in FIG. 16. As expected no signal was detected in the condition corresponding to the empty vector or the *Phaeodactylum tricornutum* wild type strain.

Thus, a TALE nuclease targeting the Enoyl ACP reductase gene induces a high frequency of targeted mutagenesis (up to 12%).

Example 7: Targeted Mutagenesis Induced by a TALE-Nuclease Targeting the Delta 12 Fatty Acid Desaturase Gene In order to determine the impact of the Delta 12 fatty acid desaturase gene (SEQ ID NO: 48) inactivation on lipid content in diatoms, one engineered TALE-Nuclease, called Delta 12 desaturase_TALE-Nuclease encoded by the pCLS19743 (SEQ ID NO: 49) and pCLS19747 (SEQ ID NO: 50) plasmids designed to cleave the DNA sequence 5'-TAGCTCCCAAGAGTGCCACCAGCTCTACTGGCA-GTGCTACCCTTAGCCAA-3' (SEQ ID NO: 51) was used.

These TALE-Nuclease encoding plasmids were co-transformed with a plasmid conferring resistance to nourseothricin (NAT) in a wild type diatom strain. The individual clones resulting from the transformation were screened for the presence of mutagenic events which lead to Delta 12 fatty acid desaturase gene inactivation.

Materials and Methods

*Phaeodactylum tricornutum* Bohlin clone CCMP2561 was grown and transformed according to the method described in example 1 with M17 tungstene particles (1.1 µm diameter, BioRad) coated with 9 µg of a total amount of DNA composed of 1.5 µg of each monomer of TALE-Nucleases (pCLS19743 (SEQ ID NO: 49) and pCLS19747 (SEQ ID NO: 50)), 3 µg of the NAT selection plasmid (pCLS16604) (SEQ ID NO: 1) and 3 µg of an empty vector (pCLS0003) (SEQ ID NO: 2) using 1.25M CaCl2 and 20 mM spermidin according to the manufacturer's instructions. As negative control, beads were coated with a DNA mixture containing 3 µg of the NAT selection plasmid (pCLS16604) and 6 µg of an empty vector (pCLS0003) (SEQ ID NO: 2).

Characterization

A-Colony Screening

After selection, resistant colonies were picked and dissociated according to the method described in example 1. Supernatants were used for each PCR reaction. Specific primers for TALE-Nuclease screens: TALE-Nuclease_For 5'-AATCTCGCCTATTCATGGTG-3' (SEQ ID NO: 7) and Stag_Rev 5'-TGTCTCTCGAACTTGGCAGCG-3' (SEQ ID NO: 9). HA_For 5'-ACCCATACGATGTTCCAGAT-TACGCT-3' (SEQ ID NO: 26) and TALE-Nuclease_Rev 5'-AATCTTGAGAAGTTGGCCTGTGTC-3' (SEQ ID NO: 27).

B-Identification of Mutagenic Event by Deep Sequencing

The Delta 12 fatty acid desaturase target was amplified using a 1:5 dilution of the lysis colony with sequence specific primers flanked by adaptators needed for HTS sequencing on the 454 sequencing system (454 Life Sciences) and the two following primers: Delta12 desaturase_For 5'-CCATCTCATCCCTGCGTGTCTCCGACTCAG-Tag-CTCGTCGGTGGTCCGTATTGG-3' (SEQ ID NO: 52) and Delta12 desaturase_Rev 5'-CCTATCCCCTGTGTGC-CTTGGCAGTCTCAG-TGGCGAGATCGCGCATCAGG-3' (SEQ ID NO: 53). 5000 to 10 000 sequences per sample were analyzed.

Results

Three weeks after the transformation of the diatoms, the clones obtained corresponding to the transformation performed with the TALE-Nuclease encoding plasmids (condition 1) were screened for the presence of both TALE-Nuclease monomers DNA sequences. The targeted mutagenesis frequency would be determined by Deep sequencing on the positive clones.

REFERENCES

Armbrust, E. V., J. A. Berges, et al. (2004). "The genome of the diatom *Thalassiosira pseudonana*: ecology, evolution, and metabolism." *Science* 306(5693): 79-86.

Boch, J., H. Scholze, et al. (2009). "Breaking the code of DNA binding specificity of TAL-type III effectors." *Science* 326(5959): 1509-12.

Bowler, C., A. E. Allen, et al. (2008). "The *Phaeodactylum* genome reveals the evolutionary history of diatom genomes." *Nature* 456(7219): 239-44.

Christian, M., T. Cermak, et al. (2010). "Targeting DNA double-strand breaks with TAL effector nucleases." *Genetics* 186(2): 757-61.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." Trends *Biochem Sci* 23(10): 394-8.

De Riso, V., R. Raniello, et al. (2009). "Gene silencing in the marine diatom *Phaeodactylum tricornutum*." *Nucleic Acids Res* 37(14): e96.

Deltcheva, E., K. Chylinski, et al. (2011). "CRISPR RNA maturation by trans-encoded small RNA and host factor RNase III." *Nature* 471(7340): 602-7.

Domergue, F., J. Lerchl, et al. (2002). "Cloning and functional characterization of *Phaeodactylum tricornutum* front-end desaturases involved in eicosapentaenoic acid biosynthesis." *Eur J Biochem* 269(16): 4105-13.

Doucha, J. and K. Livansky (2008). "Influence of processing parameters on disintegration of *Chlorella* cells in various types of homogenizers." *Appl Microbiol Biotechnol* 81(3): 431-40.

Dunahay, T. G., E. E. Jarvis, et al. (1995). "Genetic transformation of the diatoms *Cyclotella Cryptica* and *Navicula Saprophila*." *Journal of Phycology* 31(6): 1004-1012.

Falciatore, A., R. Casotti, et al. (1999). "Transformation of Nonselectable Reporter Genes in Marine Diatoms." *Mar Biotechnol (NY)* 1(3): 239-251.

Frenz, J., C. Largeau, et al. (1989). "Hydrocarbon recovery by extraction with a biocompatible solvent from free and immobilized culture of *Botryococcus braunii*." *Enz. Microb. Technol.* 11(11): 727-724.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Hejazi, M. A. and R. H. Wijffels (2004). "Milking of microalgae." *Trends Biotechnol* 22(4): 189-94.

Herrero, M., L. Jaime, et al. (2006). "Optimization of the extraction of antioxidants from *Dunaliella salina* microalga by pressurized liquids." *J Agric Food Chem* 54(15): 5597-603.

Hu, Q., M. Sommerfeld, et al. (2008). "Microalgal triacylglycerols as feedstocks for biofuel production: perspectives and advances." *Plant J* 54(4): 621-39.

Jinek, M., K. Chylinski, et al. (2012). "A programmable dual-RNA-guided DNA endonuclease in adaptive bacterial immunity." *Science* 337(6096): 816-21.

King, J. (1996). "Supercritical Fluid Technology in oil and Lipid chemistry." *AOCS Press, Champain*, IL, USa.

Kröger, M. and F. Müller-Langer (2012). "Review on possible algal-biofuel production processes." *Biofuels* 3(3): 333-349.

Kroth, P. (2007). "Molecular biology and the biotechnological potential of diatoms." *Adv Exp Med Biol* 616: 23-33.

Lackner, G., N. Moebius, et al. (2011). "Complete genome sequence of *Burkholderia rhizoxinica*, an Endosymbiont of *Rhizopus microsporus*." *J Bacteriol* 193(3): 783-4.

Lamaziere, A., C. Wolf, et al. (2013). "Lipidomics of hepatic lipogenesis inhibition by omega 3 fatty acids." *Prostaglandins Leukot Essent Fatty Acids* 88(2): 149-54.

Lamaziere, A., C. Wolf, et al. (2012). "Application of lipidomics to assess lipogenesis in drug development and pre-clinical trials." *Curr Pharm Biotechnol* 13(5): 736-45.

Lee, S. G., B. D. Yoon, et al. (1998). "Isolation of a novel pentachlorophenol-degrading bacterium, *Pseudomonas* sp. Bu34." *J Appl Microbiol* 85(1): 1-8.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mali, P., L. Yang, et al. (2013). "RNA-guided human genome engineering via Cas9." *Science* 339(6121): 823-6.

Mercer, P. and R. Armenta (2011). "Developments in oil extraction from microalgae." *Eur. J. lipid Sci. Technol.* 113(5): 539-547.

Molnar, A., A. Bassett, et al. (2009). "Highly specific gene silencing by artificial microRNAs in the unicellular alga *Chlamydomonas reinhardtii*." *Plant J* 58(1): 165-74.

Moscou, M. J. and A. J. Bogdanove (2009). "A simple cipher governs DNA recognition by TAL effectors." *Science* 326(5959): 1501.

Radakovits, R., P. M. Eduafo, et al. (2011). "Genetic engineering of fatty acid chain length in *Phaeodactylum tricornutum*." *Metab Eng* 13(1): 89-95.

Radakovits, R., R. E. Jinkerson, et al. (2010). "Genetic engineering of algae for enhanced biofuel production." *Eukaryot Cell* 9(4): 486-501.

Saade, A. and C. Bowler (2009). "Molecular tools for discovering the secrets of diatoms." *Biosciences* 59(9): 757-765.

Shen, Y., W. Yuan, et al. (2009). "Heterotrophic culture of *Chlorella* protothecoides in various nitrogen sources for lipid production." *Appl Biochem Biotechnol* 160(6): 1674-84.

Sievers, U. (1998). "Enegy optimization of supercritical fluid extraction processes with separation at supercritical pressure." *Chem. Eng. Process.* 37(5): 451-460.

Sorek, R., C. M. Lawrence, et al. (2013). "CRISPR-Mediated Adaptive Immune Systems in Bacteria and Archaea." *Annu Rev Biochem* 82: 237-66.

Vieler, A., C. Wilhelm, et al. (2007). "The lipid composition of the unicellular green alga *Chlamydomonas reinhardtii* and the diatom *Cyclotella meneghiniana* investigated by MALDI-TOF MS and TLC." *Chem Phys Lipids* 150(2): 143-55.

Wei, F., G. Z. Gao, et al. (2008). "Quantitative determination of oil content in small quantity of oilseed rape by ultrasound-assisted extraction combined with gas chromatography." *Ultrason Sonochem* 15(6): 938-42.

Zaslayskaia, L. A., J. C. Lippmeier, et al. (2001). "Trophic conversion of an obligate photoautotrophic organism through metabolic engineering." *Science* 292(5524): 2073-5.

Zhao, T., W. Wang, et al. (2009). "Gene silencing by artificial microRNAs in *Chlamydomonas*." *Plant J* 58(1): 157-64.

The invention claimed is:

1. A diatom strain, which has been genetically modified in a gene involved in lipid metabolism selected from the group consisting of: delta-12 desaturase, omega-3 desaturase, palmitoyl protein thioesterase and Enoyl ACP reductase, wherein said gene has been inactivated, and wherein said diatom strain produces an increased amount, storage and/or quality of lipids in comparison with its wild type, and has a lipid content of at least 40% of its dry weight.

2. The diatom according to claim 1, further comprising a transgene encoding a gene involved in lipid metabolism.

3. The diatom according to claim 1, wherein said gene modification has been made by expressing a TALE-nuclease, MBBBD-nuclease and/or CRISPR/Cas9 nuclease capable of targeting a sequence within said selected gene involved in lipid metabolism.

4. The diatom according to claim 1, wherein said TALE-nuclease, MBBBD-nuclease and/or CRISPR/Cas9 nuclease targets a sequence within a gene having at least 80% sequence identity with any one of the sequences selected from the group consisting of: SEQ ID NO: 30, 36, 42 and 48.

5. The diatom according to claim 1, wherein said TALE-nuclease, MBBBD-nuclease and/or CRISPR/Cas9 nuclease targets a sequence having at least 80% sequence identity with any one of the sequences selected from the group consisting of: SEQ ID NO: 33, 39, 45 and 51.

6. The diatom according to claim 1, wherein said diatom is from the genus: *Thalassiosira* sp. or *Phaeodactylum* sp.

7. The diatom of claim 6, wherein said diatom is selected from the species: *Thalassiosira pseudonana* or *Phaeodactylum tricornutum*.

8. A method for modifying the quality of lipids produced by a diatom comprising the step of:
   (a) cultivating in an adapted culture medium the diatom strain of claim 1 in which a gene involved in lipid metabolism has been inactivated by an endonuclease;
   (b) harvesting said cultivated diatom strain;
   (c) extracting the lipids from said harvested diatoms.

9. The method according to claim 8, wherein said method comprises the preliminary steps of:
   (i) selecting a target sequence within a gene of a diatom strain putatively involved in lipid metabolism;
   (ii) engineering a TALE-nuclease, a MBBBD-nuclease and/or CRISPR/Cas9 nuclease to target and inactivate said gene;
   (iii) introducing said TALE-nuclease, MBBBD-nuclease and/or CRISPR/Cas9 nuclease into said diatom;
   (iv) selecting the diatoms, in which said putative gene involved in lipid metabolism has been inactivated, producing an increased quality of lipids.

10. The method according to claim 8, wherein an exonuclease, Trex2, is further introduced into the diatom to increase mutagenesis.

11. The method according to claim 9, wherein said target sequence is selected within a gene having at least 80% sequence identity with any one of the sequences selected from the group consisting of: SEQ ID NO: 30, 36, 42 and 48.

12. The method according to claim 8, wherein said endonuclease is a TALE-nuclease, a MBBBD-nuclease and/or CRISPR/Cas9 nuclease.

13. The method according to claim 12, wherein said TALE-nuclease, MBBBD-nuclease and/or CRISPR/Cas9 nuclease targets a sequence having at least 80% sequence identity with any one of the sequence selected from the group consisting of: SEQ ID NO: 33, 39, 45 and 51.

14. The method according to claim 8, further comprising introducing into the diatom a donor matrix comprising at least one homologous region to the target sequence such that homologous recombination occurs between said donor matrix and said target sequence.

15. The method according to claim 14, wherein said donor matrix comprises a transgene encoding a gene involved in lipid metabolism.

16. The method according to claim 8, wherein said diatom produces an increased amount of shorter chain length fatty acids and/or fatty acid with a low degree of saturation.

17. The method to claim 16, wherein said increased amount of shorter chain length fatty acids and/or fatty acid with a low degree of saturation is suitable for producing biofuel.

18. The method according to claim 17, further comprising the step of producing biofuel from the extracted lipids.

19. The method according to claim 8, wherein said lipid has high content of omega-3 fatty acids, docosahexaenoic acid (DHA) and Eicosapentaenoic acid (EPA or icosapentaenoic acid).

20. The method according to claim 19, further comprising the step of transforming the extracted lipids into a cosmetic or a food product.

* * * * *

SEQUENCE LISTING

<160> NUMBER OF SEQ ID NOS: 65

<210> SEQ ID NO 1
<211> LENGTH: 4246
<212> TYPE: DNA
<213> ORGANISM: artificial sequence
<220> FEATURE:
<223> OTHER INFORMATION: pCLS16604

<400> SEQUENCE: 1

| | | | | | |
|---|---|---|---|---|---|
| gtggcacttt | tcgggggaaat | gtgcgcggaa | ccctatttg | tttatttttc | taaatacatt | 60 |
| caaatatgta | tccgctcatg | agacaataac | cctgataaat | gcttcaataa | tattgaaaaa | 120 |
| ggaagagtat | gagtattcaa | catttccgtg | tcgcccttat | tccctttttt | gcggcatttt | 180 |
| gccttcctgt | ttttgctcac | ccagaaacgc | tggtgaaagt | aaaagatgct | gaagatcagt | 240 |
| tgggtgcacg | agtgggttac | atcgaactgg | atctcaacag | cggtaagatc | cttgagagtt | 300 |
| ttcgccccga | agaacgtttt | ccaatgatga | gcacttttaa | agttctgcta | tgtggcgcgg | 360 |
| tattatcccg | tattgacgcc | gggcaagagc | aactcggtcg | ccgcatacac | tattctcaga | 420 |
| atgacttggt | tgagtactca | ccagtcacag | aaaagcatct | tacggatggc | atgacagtaa | 480 |
| gagaattatg | cagtgctgcc | ataaccatga | gtgataacac | tgcggccaac | ttacttctga | 540 |
| caacgatcgg | aggaccgaag | gagctaaccg | cttttttgca | caacatgggg | gatcatgtaa | 600 |
| ctcgccttga | tcgttgggaa | ccggagctga | atgaagccat | accaaacgac | gagcgtgaca | 660 |
| ccacgatgcc | tgtagcaatg | gcaacaacgt | tgcgcaaact | attaactggc | gaactactta | 720 |
| ctctagcttc | ccggcaacaa | ttaatagact | ggatggaggc | ggataaagtt | gcaggaccac | 780 |
| ttctgcgctc | ggcccttccg | gctggctggt | ttattgctga | taaatctgga | gccggtgagc | 840 |
| gtgggtctcg | cggtatcatt | gcagcactgg | ggccagatgg | taagccctcc | cgtatcgtag | 900 |
| ttatctacac | gacggggagt | caggcaacta | tggatgaacg | aaatagacag | atcgctgaga | 960 |
| taggtgcctc | actgattaag | cattggtaac | tgtcagacca | agtttactca | tatatacttt | 1020 |
| agattgattt | aaaacttcat | ttttaattta | aaaggatcta | ggtgaagatc | ctttttgata | 1080 |
| atctcatgac | caaaatccct | taacgtgagt | tttcgttcca | ctgagcgtca | gaccccgtag | 1140 |
| aaaagatcaa | aggatcttct | tgagatcctt | tttttctgcg | cgtaatctgc | tgcttgcaaa | 1200 |
| caaaaaaacc | accgctacca | gcggtggttt | gtttgccgga | tcaagagcta | ccaactcttt | 1260 |
| ttccgaaggt | aactggcttc | agcagagcgc | agataccaaa | tactgtcctt | ctagtgtagc | 1320 |
| cgtagttagg | ccaccacttc | aagaactctg | tagcaccgcc | tacatacctc | gctctgctaa | 1380 |
| tcctgttacc | agtggctgct | gccagtggcg | ataagtcgtg | tcttaccggg | ttggactcaa | 1440 |
| gacgatagtt | accggataag | gcgcagcggt | cgggctgaac | ggggggttcg | tgcacacagc | 1500 |
| ccagcttgga | gcgaacgacc | tacaccgaac | tgagatacct | acagcgtgag | ctatgagaaa | 1560 |
| gcgccacgct | tcccgaaggg | agaaaggcgg | acaggtatcc | ggtaagcggc | agggtcggaa | 1620 |
| caggagagcg | cacgagggag | cttccagggg | gaaacgcctg | gtatctttat | agtcctgtcg | 1680 |
| ggtttcgcca | cctctgactt | gagcgtcgat | ttttgtgatg | ctcgtcaggg | gggcggagcc | 1740 |
| tatgaaaaaa | cgccagcaac | gcggcctttt | tacggttcct | ggccttttgc | tggccttttg | 1800 |
| ctcacatgtt | ctttcctgcg | ttatcccctg | attctgtgga | taaccgtatt | accgcctttg | 1860 |
| agtgagctga | taccgctcgc | cgcagccgaa | cgaccgagcg | cagcgagtca | gtgagcgagg | 1920 |
| aagcggaaga | gcgcccaata | cgcaaaccgc | ctctccccgc | gcgttggccg | attcattaat | 1980 |
| gcagctggca | cgacaggttt | cccgactgga | aagcgggcag | tgagcgcaac | gcaattaatg | 2040 |

```
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagctcga aattaaccct cactaaaggg aacaaaagct ggtaccccgc tttggtttca   2220
cagtcaggaa taacactagc tcgtcttcac catggatgcc aatctcgccc attcatggtg   2280
tataaaagtt caacatccaa agctagaact tttggaaaga gaagaatgt ccgaataggg    2340 cacggcgtgc cgtattgttg gagtggacta gcagaaagtg aggaaggcac aggatgagtt   2400
tcctcgagac acatagcttc agcgtcgtgt aggctaggca gaggtgagtt ttctcgagac   2460
ataccttcag cgtcgtcttc actgtcacag tcaactgaca gtaatcgttg atccggagag   2520
attcaaaatt caatctgttt ggacctggat aagacacaag agcgacatcc tgacatgaac   2580
gccgtaaaca gcaaatcctg gttgaacacg tatccttttg ggggcctcca gctacgacgc   2640
tcgccccagc tggggcttcc ttactataca cagcgcatat ttcacggttg ccagaagtca   2700
agtcgaggtc gatccatatg accactcttg acgacacggc ttaccggtac cgcaccagtg   2760
tcccggggga cgccgaggcc atcgaggcac tggatgggtc cttcaccacc gacaccgtct   2820
tccgcgtcac cgccaccggg gacggcttca ccctgcggga ggtgccggtg acccgcccc    2880 tgaccaaggt gttccccgac gacgaatcgg acgacgaatc ggacgacggg gaggacggcg   2940
acccggactc ccggacgttc gtcgcgtacg gggacgacgg cgacctggcg ggcttcgtgg   3000
tcgtctcgta ctccggctgg aaccgccggc tgaccgtcga ggacatcgag gtcgccccgg   3060
agcaccgggg gcacgggtc gggcgcgcgt tgatggggct cgcgacggag ttcgcccgcg    3120
agcggggcgc cgggcacctc tggctggagg tcaccaacgt caacgcaccg gcgatccacg   3180
cgtaccggcg gatggggttc accctctgcg gcctggacac cgccctgtac gacggcaccg   3240
cctcggacgg cgagcaggcg ctctacatga gcatgccctg ccctgagcg gccgacggta    3300 tcgataagct tgatatcgaa ttcctgcagc ccggggggatc cactagttct agagcggccg   3360
caacaactac ctcgactttg gctgggacac tttcagtgag acaagaagc ttcagaagcg    3420 tgctatcgaa ctcaaccagg gacgtgcggc acaaatgggc atccttgctc tcatggtgca   3480
cgaacagttg ggagtctcta tccttcctta aaaatttaat tttcattagt tgcagtcact   3540
ccgctttggt ttcacagtca ggaataaacac tagctcgtct tcaccgcggt ggagctccaa   3600
ttcgccctat agtgagtcgt attacaattc actggccgtc gttttacaac gtcgtgactg   3660
ggaaaaccct ggcgttaccc aacttaatcg ccttgcagca catcccccett tcgccagctg   3720 gcgtaatagc gaagaggccc gcaccgatcg cccttcccaa cagttgcgca gcctgaatgg   3780
cgaatgggac gcgccctgta gcggcgcatt aagcgcggcg ggtgtggtgg ttacgcgcag   3840
cgtgaccgct acacttgcca gcgccctagc gcccgctcct ttcgctttct tcccttcctt   3900
tctcgccacg ttcgccggct ttccccgtca gctctaaat cggggggctcc ctttagggtt   3960 ccgatttagt gctttacggc acctcgaccc caaaaaactt gattagggtg atggttcacg   4020
tagtgggcca tcgccctgat agacggtttt tcgcccttg acgttggagt ccacgttctt   4080
taatagtgga ctcttgttcc aaactggaac aacactcaac cctatctcgg tctattcttt   4140
tgatttataa gggattttgc cgatttcggc ctattggtta aaaatgagc tgatttaaca   4200 aaaatttaac gcgaattttta acaaaatatt aacgcttaca atttag                4246
```

<210> SEQ ID NO 2
<211> LENGTH: 5428
<212> TYPE: DNA

<213> ORGANISM: artificial sequence
<220> FEATURE:
<223> OTHER INFORMATION: pCLS003

<400> SEQUENCE: 2

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgcc ccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattctgc     960
agatatccag cacagtggcg gccgctcgag tctagagggc ccgtttaaac ccgctgatca    1020
gcctcgactg tgccttctag ttgccagcca tctgttgttt gcccctcccc cgtgccttcc    1080
ttgaccctgg aaggtgccac tcccactgtc ctttcctaat aaaatgagga aattgcatcg    1140
cattgtctga gtaggtgtca ttctattctg ggggtgggg tggggcagga cagcaagggg    1200
gaggattggg aagacaatag caggcatgct ggggatgcgg tgggctctat ggcttctgag    1260
gcggaaagaa ccagctgggg ctctaggggg tatccccacg cgccctgtag cggcgcatta    1320
agcgcggcgg gtgtggtggt tacgcgcagc gtgaccgcta cacttgccag cgccctagcg    1380
cccgctcctt tcgctttctt cccttccttt ctcgccacgt tcgccggctt tccccgtcaa    1440
gctctaaatc gggggctccc tttagggttc cgatttagtg ctttacggca cctcgacccc    1500
aaaaaacttg attagggtga tggttcacgt agtgggccat cgccctgata gacggttttt    1560
cgccctttga cgttggagtc acgttctttt aatagtggac tcttgttcca aactggaaca    1620
acactcaacc ctatctcggt ctattctttt gatttataag gattttgcc gatttcggcc    1680
tattggttaa aaaatgagct gatttaacaa aaatttaacg cgaattaatt ctgtggaatg    1740
tgtgtcagtt agggtgtgga aagtccccag gctccccagc aggcagaagt atgcaaagca    1800
tgcatctcaa ttagtcagca accaggtgtg gaaagtcccc aggctcccca gcaggcagaa    1860
gtatgcaaag catgcatctc aattagtcag caaccatagt cccgccccta actccgccca    1920
tcccgcccct aactccgccc agttccgccc attctccgcc ccatggctga ctaatttttt    1980
ttatttatgc agaggccgag gccgcctctg cctctgagct attccagaag tagtgaggag    2040
gcttttttgg aggcctaggc ttttgcaaaa agctcccggg agcttgtata tccatttcg    2100
gatctgatca agagacagga tgaggatcgt ttcgcatgat tgaacaagat ggattgcacg    2160
caggttctcc ggccgcttgg gtggagaggc tattcggcta tgactgggca acagacaa     2220
```

```
tcggctgctc tgatgccgcc gtgttccggc tgtcagcgca ggggcgcccg gttcttttg     2280 tcaagaccga cctgtccggt gccctgaatg aactgcagga cgaggcagcg cggctatcgt     2340
ggctggccac gacgggcgtt ccttgcgcag ctgtgctcga cgttgtcact gaagcgggaa     2400
gggactggct gctattgggc gaagtgccgg ggcaggatct cctgtcatct caccttgctc     2460
ctgccgagaa agtatccatc atggctgatg caatgcggcg gctgcatacg cttgatccgg     2520
ctacctgccc attcgaccac caagcgaaac atcgcatcga gcgagcacgt actcggatgg     2580
aagccggtct tgtcgatcag gatgatctgg acgaagagca tcaggggctc gcgccagccg     2640
aactgttcgc caggctcaag gcgcgcatgc ccgacgcgcg ggatctcgtc gtgacccatg     2700
gcgatgcctg cttgccgaat atcatggtgg aaaatggccg cttttctgga ttcatcgact     2760
gtggccggct gggtgtggcg gaccgctatc aggacatagc gttggctacc cgtgatattg     2820
ctgaagagct tggcggcgaa tgggctgacc gcttcctcgt gctttacggt atcgccgctc     2880
ccgattcgca gcgcatcgcc ttctatcgcc ttcttgacga gttcttctga gcgggactct     2940
ggggttcgaa atgaccgacc aagcgacgcc caacctgcca tcacgagatt tcgattccac     3000
cgccgccttc tatgaaaggt tgggcttcgg aatcgttttc cgggacgccg gctggatgat     3060
cctccagcgc ggggatctca tgctggagtt cttcgcccac cccaacttgt ttattgcagc     3120
ttataatggt tacaaataaa gcaatagcat cacaaatttc acaaataaag catttttttc     3180
actgcattct agttgtggtt tgtccaaact catcaatgta tcttatcatg tctgtatacc     3240
gtcgacctct agctagagct tggcgtaatc atggtcatag ctgtttcctg tgtgaaattg     3300
ttatccgctc acaattccac acaacatacg agccggaagc ataaagtgta aagcctgggg     3360
tgcctaatga gtgagctaac tcacattaat tgcgttgcgc tcactgcccg ctttccagtc     3420
gggaaacctg tcgtgccagc tgcattaatg aatcggccaa cgcgcgggga gaggcggttt     3480
gcgtattggg cgctcttccg cttcctcgct cactgactcg ctgcgctcgg tcgttcggct     3540
gcggcgagcg gtatcagctc actcaaaggc ggtaatacgg ttatccacag aatcagggga     3600
taacgcagga agaacatgt gagcaaaagg ccagcaaaag gccaggaacc gtaaaaaggc     3660
cgcgttgctg gcgtttttcc ataggctccg ccccctgac gagcatcaca aaaatcgacg     3720
ctcaagtcag aggtggcgaa acccgacagg actataaaga taccaggcgt ttccccctgg     3780
aagctccctc gtgcgctctc ctgttccgac cctgccgctt accggatacc tgtccgcctt     3840
tctcccttcg ggaagcgtgg cgctttctca tagctcacgc tgtaggtatc tcagttcggt     3900
gtaggtcgtt cgctccaagc tgggctgtgt gcacgaaccc cccgttcagc ccgaccgctg     3960
cgccttatcc ggtaactatc gtcttgagtc aacccggta agacacgact tatcgccact     4020
ggcagcagcc actggtaaca ggattagcag agcgaggtat gtaggcggtg ctacagagtt     4080
cttgaagtgg tggcctaact acggctacac tagaagaaca gtatttggta tctgcgctct     4140
gctgaagcca gttaccttcg gaaaaagagt tggtagctct tgatccggca acaaaccac     4200 cgctggtagc ggtttttttg tttgcaagca gcagattacg cgcagaaaaa aaggatctca     4260
agaagatcct ttgatctttt ctacggggtc tgacgctcag tggaacgaaa actcacgtta     4320
agggattttg gtcatgagat tatcaaaaag gatcttcacc tagatccttt taaattaaaa     4380
atgaagtttt aaatcaatct aaagtatata tgagtaaact tggtctgaca gttaccaatg     4440
cttaatcagt gaggcaccta tctcagcgat ctgtctattt cgttcatcca tagttgcctg     4500
actccccgtc gtgtagataa ctacgatacg ggagggctta ccatctggcc ccagtgctgc     4560
```

```
aatgataccg cgagacccac gctcaccggc tccagattta tcagcaataa accagccagc    4620
cggaagggcc gagcgcagaa gtggtcctgc aactttatcc gcctccatcc agtctattaa    4680
ttgttgccgg gaagctagag taagtagttc gccagttaat agtttgcgca acgttgttgc    4740
cattgctaca ggcatcgtgg tgtcacgctc gtcgtttggt atggcttcat tcagctccgg    4800
ttcccaacga tcaaggcgag ttacatgatc ccccatgttg tgcaaaaaag cggttagctc    4860
cttcggtcct ccgatcgttg tcagaagtaa gttggccgca gtgttatcac tcatggttat    4920
ggcagcactg cataattctc ttactgtcat gccatccgta agatgctttt ctgtgactgg    4980
tgagtactca accaagtcat tctgagaata gtgtatgcgg cgaccgagtt gctcttgccc    5040
ggcgtcaata cgggataata ccgcgccaca tagcagaact ttaaaagtgc tcatcattgg    5100
aaaacgttct cgggggcgaa aactctcaag gatcttaccg ctgttgagat ccagttcgat    5160
gtaacccact cgtgcaccca actgatcttc agcatctttt actttcacca gcgtttctgg    5220
gtgagcaaaa acaggaaggc aaaatgccgc aaaaaaggga ataagggcga cacggaaatg    5280
ttgaatactc atactcttcc ttttcaata ttattgaagc atttatcagg gttattgtct    5340
catgagcgga tacatatttg aatgtattta gaaaaataaa caaataggggg ttccgcgcac    5400 atttccccga aaagtgccac ctgacgtc                                      5428

<210> SEQ ID NO 3
<211> LENGTH: 3613
<212> TYPE: DNA
<213> ORGANISM: Phaeodactylum tricornutum

<400> SEQUENCE: 3
ttcgaaagac gaacaacgag cctcccgaat atcctacggt tggttgctta ataacattgc      60
tttgacaact caagatgcct tctttcgatc ccattcgtgc aaaaatggaa gccggaggct     120
gtgctccatc ggcgattgcc gccttcgagt cgacctatgg tagtctcgtc tcgggtgatt     180
ccggaatgat tttggaagac tctattgcgc ccgtccccca gctggacaag accgcggagc     240
tggatattgc acccaacgcc acccttcttg ccgagacggt agttctcaaa ctcaatggtg     300
gactcggcac gggtatgggt ctggacaagg ccaagtccct gttgccagtc aaggggggacg     360 acaccttttt ggatttgacc gccaaacaag tcattcaaat gcgtaaggaa tacggtttga     420
acgtcaagtt tatgctcatg aattcgtttt ctacttccga cgataccttg agcttttga     480 gttccaaata ccctgatctt gcttccgagg aaggtttaga aatgatgcaa ataaggtcc     540 ccaagttgaa cgcggagact ctcgagccgg catcttgtga atccgatccg gaaaatgagt     600
ggtgtccgcc gggacacggt gacttgtacg cggccttggt tggctctggt cgtcttgatg     660
ccctgctcaa ggaagggttc aaatatatgt ttgtctccaa ttcggacaac cttggtgcta     720
gcctggacct tgaaattctg acttactttg ccgagaagaa tgtacccttc ttgatggagt     780
gctgcgaacg tacagaaaac gacaaaaagg gagggcactt ggccgtccgc aaatccgatg     840
gacaacttat tcttcgggaa tctgctatgt gcgctgaaga ggatgaagat gcattcagtg     900
atatcagcaa gcaccgcttt ttcaacacca acaatttgtg ggttcgtctc gataaactca     960
aggagatcat cgaccgcaat ggcggcttta ttcctctgcc catgatcaaa aacaaaaaga    1020
cggtcgaccc caaggacgac tcgtcgaccc cggtactgca gttggaaacc gctatgggtg    1080
ccgctattga atgtttcgaa ggcgccagcg cggtggttgt tcctcgcaca cgctttgcgc    1140
ccgtcaaaaa gtgcagcgat ctgctcttgc tgcgctccga tgcatacttg ctcgtggacc    1200
acaagccggt actcaatcca gcctgcaacg ggagcgcgcc cgtgatcaat ctcgacagca    1260
```

-continued

```
aactatacaa gctggtcggc gccttggaag aagcaaccca ggacggcatt ccgtccctcg    1320
tcaagtgcga caaattgact atcaagggtt tggtccggat gtcgaaaaag accaagtttg    1380
tgggtgatgt caagattgtc aactcgagcg ccgaatctaa gtttgtgccc accggtgaag    1440
taacagggga acacgatctg acgtctaatg ctggtcttgg caagctaaag cccacctctg    1500
tttcaacagc accaattgcg ggacaaaagc ctggtacttc aggactccgg aagaaggttg    1560
ccgaattcaa gaaggaaaac taccttaaca attttgtaca agctgctttt gacgccatca    1620
aggccagtgg tacggacata tcgaaggggt ccttggtaat tggtggtgat ggtcgctact    1680
tcaaccctga agcaatccaa atacttattc agatgggtgt tgctaacggc gtcagacgtt    1740
tctggattgg acaggacggc ctcttgtcga cacccgccgt ttctgcgatc attcgggaag    1800
gcggcccgcg ttggcaaaag gcatttggag cctttatttt gacggctagt cacaatcccg    1860
gtggcccaac ggaagatttt ggtatcaagt acaactgcga acatggtgag cccgctccgg    1920
agaggatgac ggatgaaatt tacgccaaca caacgacgat taagtcctac aagatttgta    1980
aggaattccc caacattgac attggcgctg cgggccactc caagatcatg tctgacgacg    2040
gcagcgccga agtcaatatt gaagtaattg attccaccga agctcacgtc aagttgttga    2100
aatctatttt tgatttctcg gccatcagag ggctgttgga tcgccccgac ttttccatgg    2160
tctacgacgc catgcacggt gtcaacgggc cgtacgtaaa aaagtattc tgcgatattc     2220 tggggcagga cctctccgtc acactgaact gtgtccccaa ggacgacttc aacggaggcc    2280
atgccgaccc caacctcacg tacgccaaag agcttgttgc cgtcatgggg cttaatcgca    2340
agggcgaaaa gatcgatatg gcggacgtc ctattcccag ctttggtgcg gccgccgacg     2400
gcgacggaga ccgcaacatg attctgggca cacagttttt tgtcagtccg tccgattcct    2460
tggcagtcat tgttgccaac gccgacacca ttccattctt ccgcacgcaa ggtggactca    2520
agggcgtcgc gcggtccatg ccaacgtccg gcgccgtcga tctcgtcgcc aaggacctga    2580
actacagttt gtttgaaaca cctacgggat ggaaatactt cgggaacctg atggattcca    2640
aagagctttt tgacggtgcc gaatacactc cgtttatttg tggggaagaa tcgttcggca    2700
caggctccga tcacattcgc gaaaaggacg gactttgggc cgtgctggct tggctcagca    2760
ttttggcgca cgccaatact aacagcctaa gtgacacact ggtgaccgtg aagacattg     2820 tcaaggctca ttgggcaaag tacggacgca actactacag ccgctgggat ttcgagaaca    2880
tgaatgcgac caaggcgaac gccatgatgg acaagatgcg ggcggaaaca gacgcgaaca    2940
cgggcaagac ggtgggcaag tactcgatcg aaaagtccga cgactttgtg tacgtggatc    3000
ccgtggacgg ctcggtggcc aagaagcagg ggatgcggtt cctaatgacg gatggctcgc    3060
ggattatttt ccgtttgagt ggcacggcgg gcagtggcgc cacggtccgc atgtacatcg    3120
aacagtacga accgacgaag attgacatgg tggcttcaga ggctttggca gatttgattc    3180
gagtcgcact ggatttatct gacctcaagg gattcctcgg aactgaagaa ccaaccgtaa    3240
ttacgtaact gatgttcgag ctctggcaac acgtcctgct aggtctcagt gtggctaact    3300
aaacgagcca gccagaacag tttcctccgt ctgatatatg aatgatgtga ctcgctcagg    3360
aatcgattcg taattgtcga gtagagcaac ttaatagtca acaacgata gccctagtgc     3420 aaaatcctcg tctcgtttcg atgggttcat gcatcctaat gcaagctgaa tatttcgttg    3480
tctatccgag taatacaaag agaaaattcg gtatttggga tgagcagggg tgaaattttc    3540
gctatttggg aaaaatcaca ctgtttctaa gtgttttat tttcgcggga aatactttct      3600
```
aagtaatctt ttt                                                    3613

<210> SEQ ID NO 4
<211> LENGTH: 5922
<212> TYPE: DNA
<213> ORGANISM: artificial sequence
<220> FEATURE:
<223> OTHER INFORMATION: pCLS19745 (TALEN UGP)

<400> SEQUENCE: 4

```
gggtacgttt aaacgtatta attaagacct agcatgtgag caaaaggcca gcaaaaggcc     60
aggaaccgta aaaaggccgc gttgctggcg ttttttccata ggctccgccc ccctgacgag    120
catcacaaaa atcgacgctc aagtcagagg tggcgaaacc cgacaggact ataaagatac    180
caggcgtttc ccctggaag ctccctcgtg cgctctcctg ttccgaccct gccgcttacc     240
ggatacctgt ccgcctttct cccttcggga agcgtggcgc tttctcatag ctcacgctgt    300
aggtatctca gttcggtgta ggtcgttcgc tccaagctgg gctgtgtgca cgaacccccc    360
gttcagcccg accgctgcgc cttatccggt aactatcgtc ttgagtccaa cccggtaaga    420
cacgacttat cgccactggc agcagccact ggtaacagga ttagcagagc gaggtatgta    480
ggcggtgcta cagagttctt gaagtggtgg cctaactacg gctacactag aaggacagta    540
tttggtatct gcgctctgct gaagccagtt accttcggaa aaagagttgg tagctcttga    600
tccggcaaac aaaccaccgc tggtagcggt ggttttttg tttgcaagca gcagattacg    660
cgcagaaaaa aaggatctca agaagatcct ttgatctttt ctacggggtc tgacgctcag    720
tggaacgaaa actcacgtta agggattttg gtcatgagat tatcaaaaag gatcttcacc    780
tagatccttt taaattaaaa atgaagtttt aaatcaatct aaagtatata tgagtaaact    840
tggtctgaca gttaccaatg cttaatcagt gaggcaccta tctcagcgat ctgtctattt    900
cgttcatcca tagttgcctg actccccgtc gtgtagataa ctacgatacg ggagggctta    960
ccatctggcc ccagtgctgc aatgataccg cgagacccac gctcaccggc tccagattta   1020
tcagcaataa accagccagc cggaagggcc gagcgcagaa gtggtcctgc aactttatcc   1080
gcctccatcc agtctattaa ttgttgccgg gaagctagag taagtagttc gccagttaat   1140
agtttgcgca acgttgttgc cattgctaca ggcatcgtgg tgtcacgctc gtcgtttggt   1200
atggcttcat tcagctccgg ttcccaacga tcaaggcgag ttacatgatc ccccatgttg   1260
tgcaaaaaag cggttagctc cttcggtcct ccgatcgttg tcagaagtaa gttggccgca   1320
gtgttatcac tcatggttat ggcagcactg cataattctc ttactgtcat gccatccgta   1380
agatgctttt ctgtgactgg tgagtactca accaagtcat tctgagaata gtgtatgcgg   1440
cgaccgagtt gctcttgccc ggcgtcaata cgggataata ccgcgccaca tagcagaact   1500
ttaaaagtgc tcatcattgg aaaacgttct tcggggcgaa aactctcaag gatcttaccg   1560
ctgttgagat ccagttcgat gtaacccact cgtgcaccca actgatcttc agcatctttt   1620
actttcacca gcgtttctgg gtgagcaaaa acaggaaggc aaaatgccgc aaaaaaggga   1680
ataagggcga cacggaaatg ttgaatactc atactcttcc ttttcaata ttattgaagc    1740
atttatcagg gttattgtct catgagcgga tacatatttg aatgtattta gaaaaataaa   1800
caaataggg ttccgcgcac atttccccga aagtgccac ctgacaaact tggtaccata    1860
actagtcgg cgcgccaatc tcgcctattc atggtgtata aagttcaac atccaaagct    1920
agaactttg gaaagagaaa gaatgtccga ataggacg gcgtgccgta ttgttggagt     1980
ggactagcag aaagtgagga aggcacagga tgagtttcct cgagacacat agcttcagcg   2040
```

```
tcgtgtaggc taggcagagg tgagttttct cgagacatac cttcagcgtc gtcttcactg    2100
tcacagtcaa ctgacagtaa tcgttgatcc ggagagattc aaaattcaat ctgtttggac    2160
ctggataaga cacaagagcg acatcctgac atgaacgccg taaacagcaa atcctggttg    2220
aacacgtatc cttttggggg cctccagcta cgacgctcgc cccagctggg gcttccttac    2280
tatacacagc gcatatttca cggttgccag aaccatgggc gatcctaaaa agaaacgtaa    2340
ggtcatcgat tacccatacg atgttccaga ttacgctatc gatatcgccg accccattcg    2400
ttcgcgcaca ccaagtcctg cccgcgagct tctgcccgga ccccaacccg atggggttca    2460
gccgactgca gatcgtgggg tgtctccgcc tgccggcggc ccctggatg gcttgccggc    2520 tcggcggacg atgtcccgga cccggctgcc atctcccccct gcccctcac ctgcgttctc    2580 ggcgggcagc ttcagtgacc tgttacgtca gttcgatccg tcacttttta atacatcgct    2640 tttgattca ttgcctccct tcggcgctca ccatacagag gctgccacag gcgagtggga    2700
tgaggtgcaa tcgggtctgc gggcagccga cgcccccca cccaccatgc gcgtggctgt    2760
cactgccgcg cggccccgc gcgccaagcc ggcgccgcga cgacgtgctg cgcaaccctc    2820
cgacgcttcg ccggcggcgc aggtggatct acgcacgctc ggctacagcc agcagcaaca    2880
ggagaagatc aaaccgaagg ttcgttcgac agtggcgcag caccacgagg cactggtcgg    2940
ccacgggttt acacacgcgc acatcgttgc gttaagccaa cacccggcag cgttagggac    3000
cgtcgctgtc aagtatcagg acatgatcgc agcgttgcca gaggcgacac acgaagcgat    3060
cgttggcgtc ggcaaacagt ggtccggcgc acgcgctctg gaggccttgc tcacggtggc    3120
gggagagttg agaggtccac cgttacagtt ggacacaggc caacttctca agattgcaaa    3180
acgtggcggc gtgaccgcag tggaggcagt gcatgcatgg cgcaatgcac tgacgggtgc    3240
cccgctcaac ttgaccccccc agcaggtggt ggccatcgcc agcaataatg gtggcaagca    3300
ggcgctggag acggtccagc ggctgttgcc ggtgctgtgc caggcccacg gcttgacccc    3360
ggagcaggtg gtggccatcg ccagccacga tggcggcaag caggcgctgg agacggtcca    3420
gcggctgttg ccggtgctgt gccaggccca cggcttgacc ccggagcagg tggtggccat    3480
cgccagccac gatggcggca agcaggcgct ggagacggtc cagcggctgt tgccggtgct    3540
gtgccaggcc cacggcttga cccccagca ggtggtggcc atcgccagca ataatggtgg    3600
caagcaggcg ctggagacgg tccagcggct gttgccggtg ctgtgccagg cccacggctt    3660
gaccccggag caggtggtgg ccatcgccag ccacgatggc ggcaagcagg cgctggagac    3720
ggtccagcgg ctgttgccgg tgctgtgcca ggcccacgc ttgaccccgg agcaggtggt    3780
ggccatcgcc agccacgatg cggcaagca ggcgctggag acggtccagc ggctgttgcc    3840
ggtgctgtgc caggcccacg gcttgacccc cagcaggtg gtggccatcg ccagcaatgg    3900
cggtggcaag caggcgctgg agacggtcca gcggctgttg ccggtgctgt gccaggccca    3960
cggcttgacc ccccagcagg tggtggccat cgccagcaat ggcggtggca agcaggcgct    4020
ggagacggtc cagcggctgt tgccggtgct gtgccaggcc cacggcttga ccccggagca    4080
ggtggtggcc atcgccagcc acgatggcgg caagcaggcg ctggagacgg tccagcggct    4140
gttgccggtg ctgtgccagg cccacggctt gaccccccag caggtggtgg ccatcgccag    4200
caataatggt ggcaagcagg cgctggagac ggtccagcgg ctgttgccgg tgctgtgcca    4260
ggcccacggc ttgaccccgg agcaggtggt ggccatcgcc agcaatattg gtggcaagca    4320
ggcgctggag acggtgcagg cgctgttgcc ggtgctgtgc caggcccacg gcttgacccc    4380
```

-continued

```
ccagcaggtg gtggccatcg ccagcaataa tggtggcaag caggcgctgg agacggtcca      4440
gcggctgttg ccggtgctgt gccaggccca cggcttgacc cccagcagg tggtggccat       4500 cgccagcaat ggcggtggca agcaggcgct ggagacggtc cagcggctgt tgccggtgct     4560
gtgccaggcc cacggcttga ccccggagca ggtggtggcc atcgccagcc acgatggcgg     4620
caagcaggcg ctggagacgg tccagcggct gttgccggtg ctgtgccagg cccacggctt     4680
gaccccccag caggtggtgg ccatcgccag caataatggt ggcaagcagg cgctggagac     4740
ggtccagcgg ctgttgccgg tgctgtgcca ggcccacggc ttgacccctc agcaggtggt     4800
ggccatcgcc agcaatggcg gcggcaggcc ggcgctggag agcattgttg cccagttatc     4860
tcgccctgat ccggcgttgg ccgcgttgac caacgaccac ctcgtcgcct tggcctgcct     4920
cggcgggcgt cctgcgctgg atgcagtgaa aaagggattg ggggatccta tcagccgttc     4980
ccagctggtg aagtccgagc tggaggagaa gaaatccgag ttgaggcaca agctgaagta     5040
cgtgccccac gagtacatcg agctgatcga gatcgcccgg aacagcaccc aggaccgtat     5100
cctggagatg aaggtgatgg agttcttcat gaaggtgtac ggctacaggg gcaagcacct     5160
gggcggctcc aggaagcccg acggcgccat ctacaccgtg gctcccccca tcgactacgg     5220
cgtgatcgtg gacaccaagg cctactccgg cggctacaac ctgcccatcg gccaggccga     5280
cgaaatgcag aggtacgtgg aggagaacca gaccaggaac aagcacatca accccaacga     5340
gtggtggaag gtgtaccccc tccagcgtga ccgagttcaag ttcctgttcg tgtccggcca     5400
cttcaagggc aactacaagg cccagctgac caggctgaac cacatcacca actgcaacgg     5460
cgccgtgctg tccgtggagg agctcctgat cggcggcgag atgatcaagg ccggcacccct    5520 gaccctggag gaggtgagga ggaagttcaa caacggcgag atcaacttcg cggccgactg     5580
ataactcgag cgatcctcta gacgagctcc tcgagcctgc agcagctgaa gctttaagat     5640
ccaatggcaa ggaccaagtg ctggaacttg ttttgctttta gcagatctag atcgagctac     5700
ctcgactttg gctgggacac tttcagtgag gacaagaagc ttcagaagcg tgctatcgaa     5760
ctcaaccagg gacgtgcggc acaaatgggc atccttgctc tcatggtgca cgaacagttg     5820
ggagtctcta tccttcctta aaaatttaat tttcattagt tgcagtcact ccgctttggt     5880
ttcacagtca ggaataacac tagctcgtct tcatatcctg ca                        5922
```

<210> SEQ ID NO 5
<211> LENGTH: 5940
<212> TYPE: DNA
<213> ORGANISM: artificial sequence
<220> FEATURE:
<223> OTHER INFORMATION: pCLS19749 (TALEN UGP)

<400> SEQUENCE: 5

```
gggtacgttt aaacgtatta attaagacct agcatgtgag caaaaggcca gcaaaaggcc        60
aggaaccgta aaaaggccgc gttgctggcg ttttttccata ggctccgccc cctgacgag      120 catcacaaaa atcgacgctc aagtcagagg tggcgaaacc cgacaggact ataaagatac      180
caggcgtttc ccctggaag ctccctcgtg cgctctcctg ttccgaccct gccgcttacc       240
ggatacctgt ccgcctttct cccttcggga agcgtggcgc tttctcatag ctcacgctgt      300
aggtatctca gttcggtgta ggtcgttcgc tccaagctgg gctgtgtgca cgaacccccc      360
gttcagcccg accgctgcgc cttatccggt aactatcgtc ttgagtccaa cccggtaaga    420
cacgacttat cgccactggc agcagccact ggtaacagga ttagcagagc gaggtatgta     480
ggcggtgcta cagagttctt gaagtggtgg cctaactacg gctacactag aaggacagta    540
```

```
tttggtatct gcgctctgct gaagccagtt accttcggaa aaagagttgg tagctcttga      600
tccggcaaac aaaccaccgc tggtagcggt ggttttttg tttgcaagca gcagattacg       660
cgcagaaaaa aaggatctca agaagatcct ttgatctttt ctacggggtc tgacgctcag      720
tggaacgaaa actcacgtta agggattttg gtcatgagat tatcaaaaag gatcttcacc     780
tagatccttt taaattaaaa atgaagtttt aaatcaatct aaagtatata tgagtaaact      840
tggtctgaca gttaccaatg cttaatcagt gaggcaccta tctcagcgat ctgtctattt     900
cgttcatcca tagttgcctg actccccgtc gtgtagataa ctacgatacg ggagggctta     960
ccatctggcc ccagtgctgc aatgataccg cgagacccac gctcaccggc tccagattta   1020
tcagcaataa accagccagc cggaagggcc gagcgcagaa gtggtcctgc aactttatcc   1080
gcctccatcc agtctattaa ttgttgccgg gaagctagag taagtagttc gccagttaat   1140
agtttgcgca acgttgttgc cattgctaca ggcatcgtgg tgtcacgctc gtcgtttggt   1200
atggcttcat tcagctccgg ttcccaacga tcaaggcgag ttacatgatc ccccatgttg   1260
tgcaaaaaag cggttagctc cttcggtcct ccgatcgttg tcagaagtaa gttggccgca   1320
gtgttatcac tcatggttat ggcagcactg cataattctc ttactgtcat gccatccgta   1380
agatgctttt ctgtgactgg tgagtactca accaagtcat tctgagaata gtgtatgcgg   1440
cgaccgagtt gctcttgccc ggcgtcaata cgggataata ccgcgccaca tagcagaact   1500
ttaaaagtgc tcatcattgg aaaacgttct tcggggcgaa aactctcaag gatcttaccg   1560
ctgttgagat ccagttcgat gtaacccact cgtgcaccca actgatcttc agcatctttt   1620
actttcacca gcgtttctgg gtgagcaaaa acaggaaggc aaaatgccgc aaaaaaggga   1680
ataagggcga cacggaaatg ttgaatactc atactcttcc tttttcaata ttattgaagc   1740
atttatcagg gttattgtct catgagcgga tacatatttg aatgtattta gaaaaataaa   1800
caaatagggg ttccgcgcac atttccccga aaagtgccac ctgacaaact tggtaccata   1860
actagttcgg cgcgccaatc tcgcctattc atggtgtata aaagttcaac atccaaagct   1920
agaacttttg gaaagagaaa gaatgtccga ataggggacg gcgtgccgta ttgttggagt   1980
ggactagcag aaagtgagga aggcacagga tgagtttcct cgagacacat agcttcagcg   2040
tcgtgtaggc taggcagagg tgagttttct cgagacatac cttcagcgtc gtcttcactg   2100
tcacagtcaa ctgacagtaa tcgttgatcc ggagagattc aaaattcaat ctgtttggac   2160
ctggataaga cacaagagcg acatcctgac atgaacgccg taaacagcaa atcctggttg   2220
aacacgtatc cttttggggg cctccagcta cgacgctcgc cccagctggg gcttccttac   2280
tatacacagc gcatatttca cggttgccag aaccatgggc gatcctaaaa agaaacgtaa   2340
ggtcatcgat aaggagaccg ccgctgccaa gttcgagaga cagcacatgg acagcatcga   2400
tatcgccgac cccattcgtt cgcgcacacc aagtcctgcc cgcgagcttc tgcccggacc   2460
ccaacccgat ggggttcagc cgactgcaga tcgtggggtg tctccgcctg ccggcggccc   2520
cctggatggc ttgccggctc ggcggacgat gtcccggacc cggctgccat ctcccctgc    2580 ccctcacct gcgttctcgg cgggcagctt cagtgacctg ttacgtcagt tcgatccgtc    2640 acttttaat acatcgcttt ttgattcatt gcctcccttc ggcgctcacc atacagaggc    2700
tgccacaggc gagtgggatg aggtgcaatc gggtctgcgg gcagccgacg ccccccacc    2760 caccatgcgc gtggctgtca ctgccgcgcg gccccgcgc gccaagccgg cgccgcgacg    2820
acgtgctgcg caaccctccg acgcttcgcc ggcggcgcag gtggatctac gcacgctcgg   2880
```

```
ctacagccag cagcaacagg agaagatcaa accgaaggtt cgttcgacag tggcgcagca    2940
ccacgaggca ctggtcggcc acgggtttac acacgcgcac atcgttgcgt taagccaaca    3000
cccggcagcg ttagggaccg tcgctgtcaa gtatcaggac atgatcgcag cgttgccaga    3060
ggcgacacac gaagcgatcg ttggcgtcgg caaacagtgg tccggcgcac gcgtctggga    3120
ggccttgctc acggtggcgg gagagttgag aggtccaccg ttacagttgg acacaggcca    3180
acttctcaag attgcaaaac gtggcggcgt gaccgcagtg gaggcagtgc atgcatggcg    3240
caatgcactg acgggtgccc cgctcaactt gaccccggag caggtggtgg ccatcgccag    3300
ccacgatggc ggcaagcagg cgctggagac ggtccagcgg ctgttgccgg tgctgtgcca    3360
ggcccacggc ttgaccccgg agcaggtggt ggccatcgcc agccacgatg gcggcaagca    3420
ggcgctggag acggtccagc ggctgttgcc ggtgctgtgc caggcccacg gcttgacccc    3480
ccagcaggtg gtggccatcg ccagcaataa tggtggcaag caggcgctgg agacggtcca    3540
gcggctgttg ccggtgctgt gccaggccca cggcttgacc cccagcaggt ggtggccat    3600 cgccagcaat aatggtggca agcaggcgct ggagacggtc agcggctgt tgccggtgct    3660 gtgccaggcc cacggcttga ccccggagca ggtggtggcc atcgccagca atattggtgg    3720
caagcaggcg ctggagacgg tgcaggcgct gttgccggtg ctgtgccagg cccacggctt    3780
gaccccggag caggtggtgg ccatcgccag caatattggt ggcaagcagg cgctggagac    3840
ggtgcaggcg ctgttgccgg tgctgtgcca ggcccacggc ttgaccccc agcaggtggt    3900 ggccatcgcc agcaatggcg gtggcaagca ggcgctggag acggtccagc ggctgttgcc    3960
ggtgctgtgc caggcccacg gcttgacccc ggagcaggtg gtggccatcg ccagccacga    4020
tggcggcaag caggcgctgg agacggtcca gcggctgttg ccggtgctgt gccaggccca    4080
cggcttgacc ccgagcagg tggtggccat cgccagcaat attggtggca agcaggcgct    4140
ggagacggtg caggcgctgt tgccggtgct gtgccaggcc cacggcttga ccccggagca    4200
ggtggtggcc atcgccagcc acgatggcgg caagcaggcg ctggagacgg tccagcggct    4260
gttgccggtg ctgtgccagg cccacggctt gaccccggag caggtggtgg ccatcgccag    4320
ccacgatggc ggcaagcagg cgctggagac ggtccagcgg ctgttgccgg tgctgtgcca    4380
ggcccacggc ttgaccccgg agcaggtggt ggccatcgcc agccacgatg gcggcaagca    4440
ggcgctggag acggtccagc ggctgttgcc ggtgctgtgc caggcccacg gcttgacccc    4500
ccagcaggtg gtggccatcg ccagcaataa tggtggcaag caggcgctgg agacggtcca    4560
gcggctgttg ccggtgctgt gccaggccca cggcttgacc ccggagcagg tggtggccat    4620
cgccagcaat attggtggca agcaggcgct ggagacggtg caggcgctgt tgccggtgct    4680
gtgccaggcc cacggcttga ccccccagca ggtggtggcc atcgccagca ataatggtgg    4740
caagcaggcg ctggagacgg tccagcggct gttgccggtg ctgtgccagg cccacggctt    4800 gaccccctcag caggtggtgg ccatcgccag caatggcggc ggcaggcggcgcc gctggagag    4860 cattgttgcc cagttatctc gccctgatcc ggcgttggcc gcgttgacca acgaccacct    4920
cgtcgccttg gcctgcctcg gcgggcgtcc tgcgctggat gcagtgaaaa agggattggg    4980
ggatcctatc agccgttccc agctggtgaa gtccgagctg gaggagaaga atccgagtt    5040 gaggcacaag ctgaagtacg tgccccacga gtacatcgag ctgatcgaga tcgcccggaa    5100 cagcaccccag gaccgtatcc tggagatgaa ggtgatggag ttcttcatga aggtgtacgg    5160 ctacagggc aagcacctgg gcggctccag gaagcccgac ggcgccatct acaccgtggg    5220 ctccccccatc gactacggcg tgatcgtgga caccaaggcc tactccggcg gctacaacct    5280
```

```
gcccatcggc caggccgacg aaatgcagag gtacgtggag gagaaccaga ccaggaacaa    5340
gcacatcaac cccaacgagt ggtggaaggt gtacccctcc agcgtgaccg agttcaagtt    5400
cctgttcgtg tccggccact tcaagggcaa ctacaaggcc cagctgacca ggctgaacca    5460
catcaccaac tgcaacggcg ccgtgctgtc cgtggaggag ctcctgatcg gcggcgagat    5520
gatcaaggcc ggcaccctga ccctggagga ggtgaggagg aagttcaaca acggcgagat    5580
caacttcgcg gccgactgat aactcgagcg atcctctaga cgagctcctc gagcctgcag    5640
cagctgaagc tttaagatcc aatggcaagg accaagtgct ggaacttgtt ttgctttagc    5700
agatctagat cgagctacct cgactttggc tgggacactt tcagtgagga caagaagctt    5760
cagaagcgtg ctatcgaact caaccaggga cgtgcggcac aaatgggcat ccttgctctc    5820
atggtgcacg aacagttggg agtctctatc cttccttaaa aatttaattt tcattagttg    5880
cagtcactcc gctttggttt cacagtcagg aataacacta gctcgtcttc atatcctgca    5940
```

<210> SEQ ID NO 6  
<211> LENGTH: 50  
<212> TYPE: DNA  
<213> ORGANISM: artificial sequence  
<220> FEATURE:  
<223> OTHER INFORMATION: UGPase target
<400> SEQUENCE: 6

```
tgccgccttc gagtcgacct atggtagtct cgtctcgggt gattccggaa               50
```

<210> SEQ ID NO 7  
<211> LENGTH: 20  
<212> TYPE: DNA  
<213> ORGANISM: artificial sequence  
<220> FEATURE:  
<223> OTHER INFORMATION: Screen TALEN_For
<400> SEQUENCE: 7

```
aatctcgcct attcatggtg                                                20
```

<210> SEQ ID NO 8  
<211> LENGTH: 21  
<212> TYPE: DNA  
<213> ORGANISM: artificial sequence  
<220> FEATURE:  
<223> OTHER INFORMATION: ScreenHA_Rev
<400> SEQUENCE: 8

```
taatctggaa catcgtatgg g                                              21
```

<210> SEQ ID NO 9  
<211> LENGTH: 21  
<212> TYPE: DNA  
<213> ORGANISM: artificial sequence  
<220> FEATURE:  
<223> OTHER INFORMATION: Screen Stag_Rev
<400> SEQUENCE: 9

```
tgtctctcga acttggcagc g                                              21
```

<210> SEQ ID NO 10  
<211> LENGTH: 63  
<212> TYPE: DNA  
<213> ORGANISM: Artificial Sequence  
<220> FEATURE:  
<223> OTHER INFORMATION: primer  
<220> FEATURE:

```
<221> NAME/KEY: misc_feature
<222> LOCATION: (31)..(32)
<223> OTHER INFORMATION: primers UGP_for;  n is a or c or t or g
<220> FEATURE:
<221> NAME/KEY: misc_feature
<222> LOCATION: (33)..(40)
<223> OTHER INFORMATION: n is a, c, g, or t

<400> SEQUENCE: 10
ccatctcatc cctgcgtgtc tccgactcag nnnnnnnnnn gttgaatcgg aatcgctaac    60
tcg                                                                 63

<210> SEQ ID NO 11
<211> LENGTH: 52
<212> TYPE: DNA
<213> ORGANISM: Artificial Sequence
<220> FEATURE:
<223> OTHER INFORMATION: Primer

<400> SEQUENCE: 11
cctatcccct gtgtgccttg gcagtctcag gacttgtttg gcggtcaaat cc            52

<210> SEQ ID NO 12
<211> LENGTH: 23
<212> TYPE: DNA
<213> ORGANISM: artificial sequence
<220> FEATURE:
<223> OTHER INFORMATION: Deep seq UGP_for

<400> SEQUENCE: 12
gttgaatcgg aatcgctaac tcg                                            23

<210> SEQ ID NO 13
<211> LENGTH: 22
<212> TYPE: DNA
<213> ORGANISM: artificial sequence
<220> FEATURE:
<223> OTHER INFORMATION: Deep seq UGP_Rev

<400> SEQUENCE: 13
gacttgtttg gcggtcaaat cc                                             22

<210> SEQ ID NO 14
<211> LENGTH: 747
<212> TYPE: DNA
<213> ORGANISM: Phaeodactylum tricornutum

<400> SEQUENCE: 14
atggaagcgc atccgttggt tcccattggc gcctgcctac tctacggact cttgatggtg    60
gcgggacagg cctactttcg cacacgcgaa ccactccggg cgcggacctc cctcgcggcc   120
tggaatctct ttctggccct cttttccctc gtcggcatgc tccggacctt tccccagctt   180
gtacacaacc tcgcgacgct cacgctccgg gaaaatctct cgccaatccc gcaagccacc   240
tacggatccg gatccaccgg attgtgggta caactcttta ttctgtccaa attccctgaa   300
ctcattgata cagtattcat cattgtcaac aagaagaaac tcatcttctt acactggtac   360
catcacatta cggtcctcct ctactgctgg cacagttacg tcaccaaatc cccgccggga   420
attttctttg tcgtcatgaa ctacaccgtc cacgcctcca tgtacggata ctactttctc   480
atggccatcc gagcccgacc ccgttggctc aatcccatga ttgtcacgac tatgcaaata   540
tcgcaaatgg tcgtgggcgt cgccgtcacc ctccttggct tttactactc ggcacgtgcc   600
gccgaccacc aatcctgtcg aattaaacgg gaaaacaaca ccgccgcctt tgtcatgtac   660
```

```
ggatcctatc tatttctctt tctgcagttc tttgtgggac gctacgttgg cacccaatcc    720
ccagtcgcgt ccaaaaagac ggcctaa                                        747

<210> SEQ ID NO 15
<211> LENGTH: 5922
<212> TYPE: DNA
<213> ORGANISM: artificial sequence
<220> FEATURE:
<223> OTHER INFORMATION: pCLS19746 (TALEN Elongase)

<400> SEQUENCE: 15
gggtacgttt aaacgtatta attaagacct agcatgtgag caaaaggcca gcaaaaggcc     60
aggaaccgta aaaaggccgc gttgctggcg ttttttccata ggctccgccc ccctgacgag    120
catcacaaaa atcgacgctc aagtcagagg tggcgaaacc cgacaggact ataaagatac    180
caggcgtttc cccctggaag ctccctcgtg cgctctcctg ttccgaccct gccgcttacc    240
ggatacctgt ccgcctttct cccttcggga agcgtggcgc tttctcatag ctcacgctgt    300
aggtatctca gttcggtgta ggtcgttcgc tccaagctgg gctgtgtgca cgaaccccc     360 gttcagcccg accgctgcgc cttatccggt aactatcgtc ttgagtccaa cccggtaaga    420
cacgacttat cgccactggc agcagccact ggtaacagga ttagcagagc gaggtatgta    480
ggcggtgcta cagagttctt gaagtggtgg cctaactacg gctacactag aaggacagta    540
tttggtatct gcgctctgct gaagccagtt accttcggaa aaagagttgg tagctcttga    600
tccggcaaac aaaccaccgc tggtagcggt ggttttttttg tttgcaagca gcagattacg    660
cgcagaaaaa aaggatctca agaagatcct ttgatctttt ctacggggtc tgacgctcag    720
tggaacgaaa actcacgtta agggatttttg gtcatgagat tatcaaaaag gatcttcacc    780
tagatccttt taaattaaaa atgaagtttt aaatcaatct aaagtatata tgagtaaact    840
tggtctgaca gttaccaatg cttaatcagt gaggcaccta tctcagcgat ctgtctattt    900
cgttcatcca tagttgcctg actccccgtc gtgtagataa ctacgatacg ggagggctta    960
ccatctggcc ccagtgctgc aatgataccg cgagacccac gctcaccggc tccagattta   1020
tcagcaataa accagccagc cggaagggcc gagcgcagaa gtggtcctgc aactttatcc   1080
gcctccatcc agtctattaa ttgttgccgg gaagctagag taagtagttc gccagttaat   1140
agtttgcgca acgttgttgc cattgctaca ggcatcgtgg tgtcacgctc gtcgtttggt   1200
atggcttcat tcagctccgg ttcccaacga tcaaggcgag ttacatgatc ccccatgttg   1260
tgcaaaaaag cggttagctc cttcggtcct ccgatcgttg tcagaagtaa gttggccgca   1320
gtgttatcac tcatggttat ggcagcactg cataattctc ttactgtcat gccatccgta   1380
agatgctttt ctgtgactgg tgagtactca accaagtcat tctgagaata gtgtatgcgg   1440
cgaccgagtt gctcttgccc ggcgtcaata cgggataata ccgcgccaca tagcagaact   1500
ttaaaagtgc tcatcattgg aaaacgttct cggggcgaaa actctcaag atcttaccg    1560 ctgttgagat ccagttcgat gtaacccact cgtgcaccca actgatcttc agcatctttt   1620
actttcacca gcgtttctgg gtgagcaaaa acaggaaggc aaaatgccgc aaaaaaggga   1680 taagggcga cacggaaatg ttgaatactc atactcttcc ttttcaata ttattgaagc    1740 atttatcagg gttattgtct catgagcgga tacatatttg aatgtattta gaaaaataaa   1800
caaatagggg ttccgcgcac atttccccga aaagtgccac ctgacaaact tggtaccata   1860
actagttcgg cgcgccaatc tcgcctatte atggtgtata aaagttcaac atccaaagct   1920
```

```
agaactttg gaaagagaaa gaatgtccga atagggcacg gcgtgccgta ttgttggagt    1980
ggactagcag aaagtgagga aggcacagga tgagtttcct cgagacacat agcttcagcg    2040
tcgtgtaggc taggcagagg tgagtttcct cgagacatac cttcagcgtc gtcttcactg    2100
tcacagtcaa ctgacagtaa tcgttgatcc ggagagattc aaaattcaat ctgtttggac    2160
ctggataaga cacaagagcg acatcctgac atgaacgccg taaacagcaa atcctggttg    2220
aacacgtatc cttttggggg cctccagcta cgacgctcgc cccagctggg gcttccttac    2280
tatacacagc gcatatttca cggttgccag aaccatgggc gatcctaaaa agaaacgtaa    2340
ggtcatcgat tacccatacg atgttccaga ttacgctatc gatatcgccg acccattcg    2400
ttcgcgcaca ccaagtcctg cccgcgagct tctgcccgga ccccaacccg atggggttca    2460
gccgactgca gatcgtgggg tgtctccgcc tgcggcggc cccctggatg gcttgccggc    2520
tcggcggacg atgtcccgga cccggctgcc atctccccct gcccctcac ctgcgttctc    2580
ggcgggcagc ttcagtgacc tgttacgtca gttcgatccg tcactttta atacatcgct    2640
ttttgattca ttgcctccct tcggcgctca ccatacagag gctgccacag gcgagtggga    2700
tgaggtgcaa tcgggtctgc gggcagccga cgcccccca cccaccatgc gcgtggctgt    2760
cactgccgcg cggcccccgc gcgccaagcc ggcgccgcga cgacgtgctg cgcaaccctc    2820
cgacgcttcg ccggcggcgc aggtggatct acgcacgctc ggctacagcc agcagcaaca    2880
ggagaagatc aaaccgaagg ttcgttcgac agtggcgcag caccacgagg cactggtcgg    2940
ccacgggttt acacacgcgc acatcgttgc gttaagccaa caccccggcag cgttagggac    3000
cgtcgctgtc aagtatcagg acatgatcgc agcgttgcca gaggcgacac acgaagcgat    3060
cgttggcgtc ggcaaacagt ggtccggcgc acgcgctctg gaggccttgc tcacggtggc    3120
gggagagttg agaggtccac cgttacagtt ggacacaggc caacttctca agattgcaaa    3180
acgtggcggc gtgaccgcag tggaggcagt gcatgcatgg cgcaatgcac tgacgggtgc    3240
cccgctcaac ttgaccccgg agcaggtggt ggccatcgcc agccacgatg gcggcaagca    3300
ggcgctggag acggtccagc ggctgttgcc ggtgctgtgc caggcccacg gcttgacccc    3360
ccagcaggtg gtgccatcg ccagcaatgg cggtggcaag caggcgctgg agacggtcca    3420
gcggctgttg ccggtgctgt gccaggccca cggcttgacc cccagcagg tggtggccat    3480
cgccagcaat ggcggtggca agcaggcgct ggagacggtc cagcggctgt tgccggtgct    3540
gtgccaggcc cacggcttga cccccagca ggtggtggcc atcgccagca atggcggtgg    3600
caagcaggcg ctggagacgg tccagcggct gttgccggtg ctgtgccagg cccacggctt    3660
gacccccag caggtggtgg ccatcgccag caatggcggt ggcaagcagg cgctggagac    3720
ggtccagcgc ctgttgccgg tgctgtgcca ggcccacggc ttgacccccg gagcaggtgg    3780
tggccatcgcc agccacgatg gcggcaagca ggcgctggag acggtccagc ggctgttgcc    3840
ggtgctgtgc caggcccacg gcttgacccc ggagcaggtg gtggccatcg ccagccacga    3900
tggcggcaag caggcgctgg agacggtcca gcggctgttg ccggtgctgt gccaggccca    3960
cggcttgacc ccggagcagg tggtggccat cgccagccac gatggcggca agcaggcgct    4020
ggagacggtc cagcggctgt tgccggtgct gtgccaggcc cacggcttga cccccagca    4080
ggtggtggcc atcgccagca atggcggtgg caagcaggcg ctggagacgg tccagcggct    4140
gttgccggtg ctgtgccagg cccacggctt gaccccggag caggtggtgg ccatcgccag    4200
ccacgatggc ggcaagcagg cgctggagac ggtccagcgg ctgttgccgg tgctgtgcca    4260
ggcccacggc ttgacccccc agcaggtggt ggccatcgcc agcaataatg gtggcaagca    4320
```

```
ggcgctggag acggtccagc ggctgttgcc ggtgctgtgc caggcccacg gcttgacccc      4380
ccagcaggtg gtggccatcg ccagcaatgg cgtggcaag caggcgctgg agacggtcca       4440
gcggctgttg ccggtgctgt gccaggccca cggcttgacc ccggagcagg tggtggccat      4500
cgccagccac gatggcggca agcaggcgct ggagacggtc cagcggctgt tgccggtgct      4560
gtgccaggcc cacggcttga ccccccagca ggtggtggcc atcgccagca ataatggtgg      4620
caagcaggcg ctggagacgg tccagcggct gttgccggtg ctgtgccagg cccacggctt      4680
gaccccccag caggtggtgg ccatcgccag caataatggt ggcaagcagg cgctggagac      4740
ggtccagcgg ctgttgccgg tgctgtgcca ggcccacggc ttgacccctc agcaggtggt      4800
ggccatcgcc agcaatggcg gcggcaggcc ggcgctggag agcattgttg cccagttatc      4860
tcgccctgat ccggcgttgg ccgcgttgac caacgaccac ctcgtcgcct ggcctgcct      4920
cggcgggcgt cctgcgctgg atgcagtgaa aaagggattg ggggatccta tcagccgttc      4980
ccagctggtg aagtccgagc tggaggagaa gaaatccgag ttgaggcaca agctgaagta      5040
cgtgccccac gagtacatcg agctgatcga gatcgcccgg aacagcaccc aggaccgtat      5100
cctggagatg aaggtgatgg agttcttcat gaaggtgtac ggctacaggg gcaagcacct      5160
gggcggctcc aggaagcccg acggcgccat ctacaccgtg gctcccccca tcgactacgg      5220
cgtgatcgtg gacaccaagg cctactccgg cggctacaac ctgcccatcg gccaggccga      5280
cgaaatgcag aggtacgtgg aggagaacca gaccaggaac aagcacatca ccccaacga       5340
gtggtggaag gtgtacccct ccagcgtgac cgagttcaag ttcctgttcg tgtccggcca      5400
cttcaagggc aactacaagg cccagctgac caggctgaac cacatcacca actgcaacgg      5460
cgccgtgctg tccgtggagg agctcctgat cggcggcgag atgatcaagg ccggcaccct      5520
gacccctggag gaggtgagga ggaagttcaa caacggcgag atcaacttcg cggccgactg      5580
ataactcgag cgatcctcta gacgagctcc tcgagcctgc agcagctgaa gctttaagat      5640
ccaatggcaa ggaccaagtg ctggaacttg ttttgcttta gcagatctag atcgagctac      5700
ctcgactttg gctgggacac tttcagtgag acaagaagc ttcagaagcg tgctatcgaa       5760
ctcaaccagg gacgtgcggc acaaatgggc atccttgctc tcatggtgca cgaacagttg      5820
ggagtctcta tccttcctta aaaatttaat tttcattagt tgcagtcact ccgctttggt      5880
ttcacagtca ggaataacac tagctcgtct tcatatcctg ca                        5922
```

<210> SEQ ID NO 16
<211> LENGTH: 5940
<212> TYPE: DNA
<213> ORGANISM: artificial sequence
<220> FEATURE:
<223> OTHER INFORMATION: pCLS19750 (TALEN Elongase)

<400> SEQUENCE: 16

```
gggtacgttt aaacgtatta attaagacct agcatgtgag caaaaggcca gcaaaaggcc       60
aggaaccgta aaaaggccgc gttgctggcg ttttttccata ggctccgccc ccctgacgag      120
catcacaaaa atcgacgctc aagtcagagg tggcgaaacc cgacaggact ataaagatac      180
caggcgtttc cccctggaag ctccctcgtg cgctctcctg ttccgaccct gccgcttacc      240
ggatacctgt ccgcctttct cccttcggga agcgtggcgc tttctcatag ctcacgctgt      300
aggtatctca gttcggtgta ggtcgttcgc tccaagctgg gctgtgtgca cgaacccccc      360
gttcagcccg accgctgcgc cttatccggt aactatcgtc ttgagtccaa cccggtaaga      420
```

```
cacgacttat cgccactggc agcagccact ggtaacagga ttagcagagc gaggtatgta    480
ggcggtgcta cagagttctt gaagtggtgg cctaactacg gctacactag aaggacagta    540
tttggtatct gcgctctgct gaagccagtt accttcggaa aaagagttgg tagctcttga    600
tccggcaaac aaaccaccgc tggtagcggt ggttttttg tttgcaagca gcagattacg    660
cgcagaaaaa aaggatctca agaagatcct ttgatctttt ctacggggtc tgacgctcag    720
tggaacgaaa actcacgtta agggattttg gtcatgagat tatcaaaaag gatcttcacc    780
tagatccttt taaattaaaa atgaagtttt aaatcaatct aaagtatata tgagtaaact    840
tggtctgaca gttaccaatg cttaatcagt gaggcaccta tctcagcgat ctgtctattt    900
cgttcatcca tagttgcctg actccccgtc gtgtagataa ctacgatacg ggagggctta    960
ccatctggcc ccagtgctgc aatgataccg cgagacccac gctcaccggc tccagattta   1020
tcagcaataa accagccagc cggaagggcc gagcgcagaa gtggtcctgc aactttatcc   1080
gcctccatcc agtctattaa ttgttgccgg gaagctagag taagtagttc gccagttaat   1140
agtttgcgca acgttgttgc cattgctaca ggcatcgtgg tgtcacgctc gtcgtttggt   1200
atggcttcat tcagctccgg ttcccaacga tcaaggcgag ttacatgatc ccccatgttg   1260
tgcaaaaaag cggttagctc cttcggtcct ccgatcgttg tcagaagtaa gttggccgca   1320
gtgttatcac tcatggttat ggcagcactg cataattctc ttactgtcat gccatccgta   1380
agatgctttt ctgtgactgg tgagtactca accaagtcat tctgagaata gtgtatgcgg   1440
cgaccgagtt gctcttgccc ggcgtcaata cgggataata ccgcgccaca tagcagaact   1500
ttaaaagtgc tcatcattgg aaaacgttct tcggggcgaa aactctcaag gatcttaccg   1560
ctgttgagat ccagttcgat gtaacccact cgtgcaccca actgatcttc agcatctttt   1620
actttcacca gcgtttctgg gtgagcaaaa acaggaaggc aaaatgccgc aaaaaaggga   1680
ataagggcga cacggaaatg ttgaatactc atactcttcc ttttttcaata ttattgaagc   1740
atttatcagg gttattgtct catgagcgga tacatatttg aatgtattta gaaaaataaa   1800
caaatagggg ttccgcgcac atttccccga aaagtgccac ctgacaaact tggtaccata   1860
actagttcgg cgcgccaatc tcgcctattc atggtgtata aaagttcaac atccaaagct   1920
agaactttg gaaagagaaa gaatgtccga atagggcacg gcgtgccgta ttgttggagt   1980
ggactagcag aaagtgagga aggcacagga tgagtttcct cgagacacat agcttcagcg   2040
tcgtgtaggc taggcagagg tgagttttct cgagacatac cttcagcgtc gtcttcactg   2100
tcacagtcaa ctgacagtaa tcgttgatcc ggagagattc aaaattcaat ctgtttggac   2160
ctggataaga cacaagagcg acatcctgac atgaacgccg taaacagcaa atcctggttg   2220
aacacgtatc cttttggggg cctccagcta cgacgctcgc cccagctggg gcttccttac   2280
tatacacagc gcatatttca cggttgccag aaccatgggc gatcctaaaa agaaacgtaa   2340
ggtcatcgat aaggagaccg ccgctgccaa gttcgagaga cagcacatgg acagcatcga   2400
tatcgccgac cccattcgtt cgcgcacacc aagtcctgcc cgcgagcttc tgcccggacc   2460
ccaacccgat ggggttcagc cgactgcaga tcgtggggtg tctccgcctg ccggcggccc   2520
cctggatggc ttgccggctc ggcggacgat gtccgggacc cggctgccat ctcccctgc    2580
cccctcacct gcgttctcgg cgggcagctt cagtgacctg ttacgtcagt tcgatccgtc   2640
acttttttaat acatcgcttt ttgattcatt gcctcccttc ggcgctcacc atacagaggc   2700
tgccacaggc gagtgggatg aggtgcaatc gggtctgcgg gcagccgacg ccccccccacc   2760
caccatgcgc gtggctgtca ctgccgcgcg gccccgcgc gccaagccgg cgccgcgacg   2820
```

```
acgtgctgcg caaccctccg acgcttcgcc ggcggcgcag gtggatctac gcacgctcgg    2880
ctacagccag cagcaacagg agaagatcaa accgaaggtt cgttcgacag tggcgcagca    2940
ccacgaggca ctggtcggcc acgggtttac acacgcgcac atcgttgcgt taagccaaca    3000
cccggcagcg ttagggaccg tcgctgtcaa gtatcaggac atgatcgcag cgttgccaga    3060
ggcgacacac gaagcgatcg ttggcgtcgg caaacagtgg tccggcgcac gcgctctgga    3120
ggccttgctc acggtggcgg gagagttgag aggtccaccg ttacagttgg acacaggcca    3180
acttctcaag attgcaaaac gtggcggcgt gaccgcagtg gaggcagtgc atgcatggcg    3240
caatgcactg acgggtgccc cgctcaactt gaccccccag caggtggtgg ccatcgccag    3300
caatggcggt ggcaagcagg cgctggagac ggtccagcgg ctgttgccgg tgctgtgcca    3360
ggcccacggc ttgaccccccc agcaggtggt ggccatcgcc agcaataatg gtggcaagca    3420
ggcgctggag acggtccagc ggctgttgcc ggtgctgtgc caggcccacg gcttgacccc    3480
ccagcaggtg gtgccatcg ccagcaatgg cggtggcaag caggcgctgg agacggtcca    3540
gcggctgttg ccggtgctgt gccaggccca cggcttgacc cccagcagg tggtggccat    3600 cgccagcaat aatggtggca agcaggcgct ggagacggtc agcggctgt tgccggtgct    3660 gtgccaggcc cacggcttga ccccccagca ggtggtggcc atcgccagca atggcggtgg    3720
caagcaggcg ctggagacgg tccagcggct gttgccggtg ctgtgccagg cccacggctt    3780 gacccccggag caggtggtgg ccatcgccag caatattggt ggcaagcagg cgctggagac    3840 ggtgcaggc ctgttgccgg tgctgtgcca ggcccacggc ttgaccccgg agcaggtggt    3900
ggccatcgcc agccacgatg gcggcaagca ggcgctggag acggtccagc ggctgttgcc    3960
ggtgctgtgc caggcccacg gcttgacccc ggagcaggtg gtggccatcg ccagcaatat    4020
tggtggcaag caggcgctgg agacggtgca ggcgctgttg ccggtgctgt gccaggccca    4080
cggcttgacc ccggagcagg tggtggccat cgccagcaat attggtggca agcaggcgct    4140
ggagacggtg caggcgctgt tgccggtgct gtgccaggcc cacggcttga ccccccagca    4200
ggtggtggcc atcgccagca ataatggtgg caagcaggcg ctggagacgg tccagcggct    4260
gttgccggtg ctgtgccagg cccacggctt gaccccggag caggtggtgg ccatcgccag    4320
ccacgatggc ggcaagcagg cgctggagac ggtccagcgg ctgttgccgg tgctgtgcca    4380
ggcccacggc ttgaccccccc agcaggtggt ggccatcgcc agcaatggcg gtggcaagca    4440
ggcgctggag acggtccagc ggctgttgcc ggtgctgtgc caggcccacg gcttgacccc    4500
ccagcaggtg gtgccatcg ccagcaataa tggtggcaag caggcgctgg agacggtcca    4560
gcggctgttg ccggtgctgt gccaggccca cggcttgacc cccagcagg tggtggccat    4620 cgccagcaat aatggtggca agcaggcgct ggagacggtc agcggctgt tgccggtgct    4680 gtgccaggcc cacggcttga ccccccagca ggtggtggcc atcgccagca ataatggtgg    4740
caagcaggcg ctggagacgg tccagcggct gttgccggtg ctgtgccagg cccacggctt    4800
gacccctcag caggtggtgg ccatcgccag caatggcggc ggcaggccgg cgctggagag    4860
cattgttgcc cagttatctc gccctgatcc ggcgttggcc gcgttgacca acgaccacct    4920
cgtcgccttg gcctgcctcg gcgggcgtcc tgcgctggat gcagtgaaaa agggattggg    4980
ggatcctatc agccgttccc agctggtgaa gtccgagctg aggagaaga aatccgagtt    5040 gaggcacaag ctgaagtacg tgccccacga gtacatcgag ctgatcgaga tcgcccggaa    5100
cagcacccag gaccgtatcc tggagatgaa ggtgatggag ttcttcatga aggtgtacgg    5160
```

```
ctacaggggc aagcacctgg gcggctccag gaagcccgac ggcgccatct acaccgtggg    5220
ctcccccatc gactacggcg tgatcgtgga caccaaggcc tactccggcg gctacaacct    5280
gcccatcggc caggccgacg aaatgcagag gtacgtggag gagaaccaga ccaggaacaa    5340
gcacatcaac cccaacgagt ggtggaaggt gtaccccctcc agcgtgaccg agttcaagtt    5400
cctgttcgtg tccggccact tcaagggcaa ctacaaggcc cagctgacca ggctgaacca    5460
catcaccaac tgcaacggcg ccgtgctgtc cgtggaggag ctcctgatcg gcggcgagat    5520
gatcaaggcc ggcaccctga ccctggagga ggtgaggagg aagttcaaca acggcgagat    5580
caacttcgcg gccgactgat aactcgagcg atcctctaga cgagctcctc gagcctgcag    5640
cagctgaagc tttaagatcc aatggcaagg accaagtgct ggaacttgtt ttgctttagc    5700
agatctagat cgagctacct cgactttggc tgggacactt tcagtgagga caagaagctt    5760
cagaagcgtg ctatcgaact caaccaggga cgtgcggcac aaatgggcat ccttgctctc    5820
atggtgcacg aacagttggg agtctctatc cttccttaaa aatttaattt tcattagttg    5880
cagtcactcc gctttggttt cacagtcagg aataacacta gctcgtcttc atatcctgca    5940
```

<210> SEQ ID NO 17
<211> LENGTH: 49
<212> TYPE: DNA
<213> ORGANISM: artificial sequence
<220> FEATURE:
<223> OTHER INFORMATION: Elongase target

<400> SEQUENCE: 17
tcttttccct cgtcggcatg ctccggacct ttccccagct tgtacacaa                49

<210> SEQ ID NO 18
<211> LENGTH: 59
<212> TYPE: DNA
<213> ORGANISM: artificial sequence
<220> FEATURE:
<223> OTHER INFORMATION: Primer
<220> FEATURE:
<221> NAME/KEY: misc_feature
<222> LOCATION: (31)..(32)
<223> OTHER INFORMATION: primer Elongase_For ; n is a or c or t or g
<220> FEATURE:
<221> NAME/KEY: misc_feature
<222> LOCATION: (33)..(40)
<223> OTHER INFORMATION: n is a, c, g, or t

<400> SEQUENCE: 18
ccatctcatc cctgcgtgtc tccgactcag nnnnnnnnnn aagcgcatcc gttggttcc     59

<210> SEQ ID NO 19
<211> LENGTH: 52
<212> TYPE: DNA
<213> ORGANISM: artificial sequence
<220> FEATURE:
<223> OTHER INFORMATION: primer Elongase_Rev

<400> SEQUENCE: 19
cctatcccct gtgtgccttg gcagtctcag tcaatgagtt cactggaaag gg            52

<210> SEQ ID NO 20
<211> LENGTH: 19
<212> TYPE: DNA
<213> ORGANISM: artificial sequence
<220> FEATURE:
<223> OTHER INFORMATION: Deep seq Elongase_For

<400> SEQUENCE: 20

```
aagcgcatcc gttggttcc                                                19
```

<210> SEQ ID NO 21
<211> LENGTH: 22
<212> TYPE: DNA
<213> ORGANISM: artificial sequence
<220> FEATURE:
<223> OTHER INFORMATION: Deep seq Elongase_Rev

<400> SEQUENCE: 21

```
tcaatgagtt cactggaaag gg                                            22
```

<210> SEQ ID NO 22
<211> LENGTH: 1161
<212> TYPE: DNA
<213> ORGANISM: Phaeodactylum tricornutum

<400> SEQUENCE: 22

```
atggactcaa atcctcaaaa tagttctgac caactcgata agtatgcat catcggtagc    60
ggtaactggg gaagtgccat tgcgacccta gttggtcgca actgcgagcg cttgcccttt   120
ttcgaatcgc aggtcaacat gtgggtcttt gaggaaatgg ttgaattgga agatggttcc   180
caaaagaagc tcaccgaaat catcaactct cgccacgaaa acgttaagta cctcccaggc   240
attcccctcc cttccaacgt tgttgcgact cctgatctag cagaagcctg tcgcgatgcc   300
acgctcttga tctttgtcct accccaccaa ttcttaccgc gactacttcc cgtcattcgc   360
gagtcggcgc acccaacctg tcgggggggtt agtctcatca aagggcttga cttcgactcg   420
gaacgcaaac ttccaatcct tatttccaac acaatcgctg acgccatggg aacctgaattt   480
caatgcggcg ttctgatggg agcgaacgtt gcctccgagg ttgctctggg tcaaatgtgc   540
gagtccacct tggcgtctcc ctttggtcca ccagcagatg agctgacacg tctcgtcttt   600
gacgctccct ccttccgagt gcagcacgtg ccagacgttg cgggtgccga agtctgcggt   660
gcgcttaaga acgtagttgc tctcggcgca ggttttgttg atggcgttgg actcggaagc   720
aatactaagg cggctctgct tagagtggga cttcgagaga tggccaagtt ttgccacatg   780
ttctttgacg gcgttcaaga taatacccttt acgcagagct gtggcatggc agatttaatc   840
acgacatgct acggtggaag gaatcgcaaa tgtgcggaag cttttgcgaa ggaacgtctt   900
ggatcggacg ggctctgcga cgaggctatg gcgtgtgaac aaaagtggga gaagattgaa   960
gccaaacttc tcaacggcca aaagctgcaa ggaactctaa cggcgaaaga agttcacgcc  1020
atacttgact ctcgagggt ccttaacgca tttcctctaa tcaaaacgat ccatgagatt  1080
tcttttaaag ggaaacctgt acaacagatt gtggatggta ttattgatac gaacgagcac  1140
ggagctagct cgcacttgta a                                           1161
```

<210> SEQ ID NO 23
<211> LENGTH: 5922
<212> TYPE: DNA
<213> ORGANISM: artificial sequence
<220> FEATURE:
<223> OTHER INFORMATION: pCLS23159 (TALEN G3PDH)

<400> SEQUENCE: 23

```
gggtacgttt aaacgtatta attaagacct agcatgtgag caaaaggcca gcaaaaggcc    60
aggaaccgta aaaaggccgc gttgctggcg ttttttccata ggctccgccc ccctgacgag   120
catcacaaaa atcgacgctc aagtcagagg tggcgaaacc cgacaggact ataaagatac   180
```

```
caggcgtttc ccccctggaag ctccctcgtg cgctctcctg ttccgaccct gccgcttacc      240
ggatacctgt ccgcctttct cccttcggga agcgtggcgc tttctcatag ctcacgctgt      300
aggtatctca gttcggtgta ggtcgttcgc tccaagctgg gctgtgtgca cgaaccccccc     360
gttcagcccg accgctgcgc cttatccggt aactatcgtc ttgagtccaa cccggtaaga      420
cacgacttat cgccactggc agcagccact ggtaacagga ttagcagagc gaggtatgta      480
ggcggtgcta cagagttctt gaagtggtgg cctaactacg gctacactag aaggacagta      540
tttggtatct gcgctctgct gaagccagtt accttcggaa aaagagttgg tagctcttga      600
tccggcaaac aaaccaccgc tggtagcggt ggttttttg tttgcaagca gcagattacg       660
cgcagaaaaa aaggatctca agaagatcct ttgatctttt ctacggggtc tgacgctcag      720
tggaacgaaa actcacgtta agggattttg gtcatgagat tatcaaaaag gatcttcacc      780
tagatccttt taaattaaaa atgaagtttt aaatcaatct aaagtatata tgagtaaact      840
tggtctgaca gttaccaatg cttaatcagt gaggcaccta tctcagcgat ctgtctattt      900
cgttcatcca tagttgcctg actccccgtc gtgtagataa ctacgatacg ggagggctta      960
ccatctggcc ccagtgctgc aatgataccg cgagacccac gctcaccggc tccagattta     1020
tcagcaataa accagccagc cggaagggcc gagcgcagaa gtggtcctgc aactttatcc     1080
gcctccatcc agtctattaa ttgttgccgg gaagctagag taagtagttc gccagttaat     1140
agtttgcgca acgttgttgc cattgctaca ggcatcgtgg tgtcacgctc gtcgtttggt     1200
atggcttcat tcagctccgg ttcccaacga tcaaggcgag ttacatgatc ccccatgttg     1260
tgcaaaaaag cggttagctc cttcggtcct ccgatcgttg tcagaagtaa gttggccgca     1320
gtgttatcac tcatggttat ggcagcactg cataattctc ttactgtcat gccatccgta     1380
agatgctttt ctgtgactgg tgagtactca accaagtcat tctgagaata gtgtatgcgg     1440
cgaccgagtt gctcttgccc ggcgtcaata cgggataata ccgcgccaca tagcagaact     1500
ttaaaagtgc tcatcattgg aaaacgttct cggggcgaaa actctcaagg atcttaccg      1560
ctgttgagat ccagttcgat gtaacccact cgtgcaccca actgatcttc agcatctttt     1620
actttcacca gcgtttctgg gtgagcaaaa acaggaaggc aaaatgccgc aaaaaaggga     1680
ataagggcga cacggaaatg ttgaatactc atactcttcc ttttcaata ttattgaagc      1740
atttatcagg gttattgtct catgagcgga tacatatttg aatgtattta gaaaataaa      1800
caaataggggg ttccgcgcac atttccccga aaagtgccac ctgacaaact tggtaccata     1860
actagttcgg cgcgccaatc tcgcctattc atggtgtata aaagttcaac atccaaagct     1920
agaactttg gaaagagaaa gaatgtccga atagggcacg gcgtgccgta ttgttggagt      1980
ggactagcag aaagtgagga aggcacagga tgagtttcct cgagacacat agcttcagcg     2040
tcgtgtaggc taggcagagg tgagttttct cgagacatac cttcagcgtc gtcttcactg     2100
tcacagtcaa ctgacagtaa tcgttgatcc ggagagattc aaaattcaat ctgtttggac     2160
ctggataaga cacaagagcg acatcctgac atgaacgccg taaacagcaa atcctggttg     2220
aacacgtatc cttttggggg cctccagcta cgacgctcgc cccagctggg gcttccttac     2280
tatacacagc gcatatttca cggttgccag aaccatgggc gatcctaaaa agaaacgtaa     2340
ggtcatcgat tacccatacg atgttccaga ttacgctatc gatatcgccg accccattcg     2400
ttcgcgcaca ccaagtcctg cccgcgagct tctgcccgga ccccaacccg atggggttca     2460
gccgactgca gatcgtgggg tgtctccgcc tgccggcggc ccctggatg gcttgccggc      2520
tcggcggacg atgtcccgga cccggctgcc atctccccct gccccctcac ctgcgttctc     2580
```

```
ggcgggcagc ttcagtgacc tgttacgtca gttcgatccg tcactttta atacatcgct      2640 tttttgattca ttgcctccct tcggcgctca ccatacagag gctgccacag gcgagtggga    2700
tgaggtgcaa tcgggtctgc gggcagccga cgcccccca cccaccatgc gcgtggctgt     2760
cactgccgcg cggcccccgc gcgccaagcc ggcgccgcga cgacgtgctg cgcaaccctc    2820
cgacgcttcg ccggcggcgc aggtggatct acgcacgctc ggctacagcc agcagcaaca    2880
ggagaagatc aaaccgaagg ttcgttcgac agtggcgcag caccacgagg cactggtcgg    2940
ccacggtttt acacacgcgc acatcgttgc gttaagccaa caccccggcag cgttagggac   3000 cgtcgctgtc aagtatcagg acatgatcgc agcgttgcca gaggcgacac acgaagcgat    3060
cgttggcgtc ggcaaacagt ggtccggcgc acgcgctctg gaggccttgc tcacggtggc    3120
gggagagttg agaggtccac cgttacagtt ggacacaggc caacttctca agattgcaaa    3180
acgtggcggc gtgaccgcag tggaggcagt gcatgcatgg cgcaatgcac tgacgggtgc    3240
cccgctcaac ttgaccccgg agcaggtggt ggccatcgcc agccacgatg gcggcaagca    3300
ggcgctggag acggtccagc ggctgttgcc ggtgctgtgc caggcccacg gcttgacccc    3360
ccagcaggtg gtgccatcg ccagcaatgg cggtggcaag caggcgctgg agacggtcca     3420
gcggctgttg ccggtgctgt gccaggccca cggcttgacc cccagcagg tggtggccat     3480 cgccagcaat aatggtggca agcaggcgct ggagacggtc cagcggctgt tgccggtgct    3540
gtgccaggcc cacggcttga ccccggagca ggtggtggcc atcgccagca atattggtgg   3600
caagcaggcg ctggagacgg tgcaggcgct gttgccggtg ctgtgccagg cccacggctt    3660
gaccccggag caggtggtgg ccatcgccag ccacgatggc ggcaagcagg cgctggagac    3720
ggtccagcgg ctgttgccgg tgctgtgcca ggcccacggc ttgaccccgg agcaggtggt    3780
ggccatcgcc agccacgatg gcggcaagca ggcgctggag acggtccagc ggctgttgcc    3840
ggtgctgtgc caggcccacg gcttgacccc ggagcaggtg gtggccatcg ccagcaatat   3900
tggtggcaag caggcgctgg agacggtgca ggcgctgttg ccggtgctgt gccaggccca    3960
cggcttgacc ccggagcagg tggtggccat cgccagcaat attggtggca agcaggcgct    4020
ggagacggtg caggcgctgt tgccggtgct gtgccaggcc cacggcttga ccccggagca    4080
ggtggtggcc atcgccagcc acgatggcgg caagcaggcg ctggagacgg tccagcggct    4140
gttgccggtg ctgtgccagg cccacggctt gaccccccag caggtggtgg ccatcgccag    4200
caatggcggt ggcaagcagg cgctggagac ggtccagcgg ctgttgccgg tgctgtgcca    4260
ggcccacggc ttgaccccgg agcaggtggt ggccatcgcc agccacgatg gcggcaagca    4320
ggcgctggag acggtccagc ggctgttgcc ggtgctgtgc caggcccacg gcttgacccc    4380
ccagcaggtg gtgccatcg ccagcaataa tggtggcaag caggcgctgg agacggtcca     4440
gcggctgttg ccggtgctgt gccaggccca cggcttgacc ccggagcagg tggtggccat    4500
cgccagcaat attggtggca agcaggcgct ggagacggtg caggcgctgt tgccggtgct    4560
gtgccaggcc cacggcttga cccccagca ggtggtggcc atcgccagca atggcggtgg    4620
caagcaggcg ctggagacgg tccagcggct gttgccggtg ctgtgccagg cccacggctt    4680
gaccccggag caggtggtgg ccatcgccag caatattggt ggcaagcagg cgctggagac    4740
ggtgcaggcg ctgttgccgg tgctgtgcca ggcccacggc ttgacccctc agcaggtggt    4800
ggccatcgcc agcaatggcg gcggcaggcc ggcgctggag agcattgttg cccagttatc    4860
tcgccctgat ccggcgttgg ccgcgttgac caacgaccac ctcgtcgcct tggcctgcct    4920
```

| | |
|---|---:|
| cggcgggcgt cctgcgctgg atgcagtgaa aaagggattg gggatcccta tcagccgttc | 4980 |
| ccagctggtg aagtccgagc tggaggagaa gaaatccgag ttgaggcaca agctgaagta | 5040 |
| cgtgccccac gagtacatcg agctgatcga gatcgcccgg aacagcaccc aggaccgtat | 5100 |
| cctggagatg aaggtgatgg agttcttcat gaaggtgtac ggctacaggg gcaagcacct | 5160 |
| gggcggctcc aggaagcccg acggcgccat ctacaccgtg gctcccccca tcgactacgg | 5220 |
| cgtgatcgtg gacaccaagg cctactccgg cggctacaac ctgcccatcg gccaggccga | 5280 |
| cgaaatgcag aggtacgtgg aggagaacca gaccaggaac aagcacatca cccccaacga | 5340 |
| gtggtggaag gtgtaccccc tccagcgtga ccgagttcaag ttcctgttcg tgtccggcca | 5400 |
| cttcaagggc aactacaagg cccagctgac caggctgaac cacatcacca actgcaacgg | 5460 |
| cgccgtgctg tccgtggagg agctcctgat cggcggcgag atgatcaagg ccggcacccct | 5520 |
| gaccctggag gaggtgagga ggaagttcaa caacggcgag atcaacttcg cggccgactg | 5580 |
| ataactcgag cgatcctcta gacgagctcc tcgagcctgc agcagctgaa gctttaagat | 5640 |
| ccaatggcaa ggaccaagtg ctggaacttg ttttgcttta gcagatctag atcgagctac | 5700 |
| ctcgactttg gctgggacac tttcagtgag gacaagaagc ttcagaagcg tgctatcgaa | 5760 |
| ctcaaccagg gacgtgcggc acaaatgggc atccttgctc tcatggtgca cgaacagttg | 5820 |
| ggagtctcta tccttcctta aaaatttaat tttcattagt tgcagtcact ccgctttggt | 5880 |
| ttcacagtca ggaataacac tagctcgtct tcatatcctg ca | 5922 |

<210> SEQ ID NO 24
<211> LENGTH: 5940
<212> TYPE: DNA
<213> ORGANISM: artificial sequence
<220> FEATURE:
<223> OTHER INFORMATION: pCLS23163 (TALEN G3PDH)

<400> SEQUENCE: 24

| | |
|---|---:|
| gggtacgttt aaacgtatta attaagacct agcatgtgag caaaaggcca gcaaaaggcc | 60 |
| aggaaccgta aaaaggccgc gttgctggcg ttttttccata ggctccgccc ccctgacgag | 120 |
| catcacaaaa atcgacgctc aagtcagagg tggcgaaacc cgacaggact ataaagatac | 180 |
| caggcgtttc cccctggaag ctccctcgtg cgctctcctg ttccgaccct gccgcttacc | 240 |
| ggatacctgt ccgcctttct cccttcggga agcgtggcgc tttctcatag ctcacgctgt | 300 |
| aggtatctca gttcggtgta ggtcgttcgc tccaagctgg gctgtgtgca cgaaccccc | 360 |
| gttcagcccg accgctgcgc cttatccggt aactatcgtc ttgagtccaa cccggtaaga | 420 |
| cacgacttat cgccactggc agcagccact ggtaacagga ttagcagagc gaggtatgta | 480 |
| ggcggtgcta cagagttctt gaagtggtgg cctaactacg gctacactag aaggacagta | 540 |
| tttggtatct gcgctctgct gaagccagtt accttcggaa aaagagttgg tagctcttga | 600 |
| tccggcaaac aaaccaccgc tggtagcggt ggttttttg tttgcaagca gcagattacg | 660 |
| cgcagaaaaa aaggatctca agaagatcct ttgatctttt ctacggggtc tgacgctcag | 720 |
| tggaacgaaa actcacgtta agggattttg gtcatgagat tatcaaaaag gatcttcacc | 780 |
| tagatccttt taaattaaaa atgaagtttt aaatcaatct aaagtatata tgagtaaact | 840 |
| tggtctgaca gttaccaatg cttaatcagt gaggcaccta tctcagcgat ctgtctattt | 900 |
| cgttcatcca tagttgcctg actccccgtc gtgtagataa ctacgatacg ggagggctta | 960 |
| ccatctggcc ccagtgctgc aatgataccg cgagacccac gctcaccggc tccagattta | 1020 |
| tcagcaataa accagccagc cggaagggcc gagcgcagaa gtggtcctgc aactttatcc | 1080 |

```
gcctccatcc agtctattaa ttgttgccgg gaagctagag taagtagttc gccagttaat   1140
agtttgcgca acgttgttgc cattgctaca ggcatcgtgg tgtcacgctc gtcgtttggt   1200
atggcttcat tcagctccgg ttcccaacga tcaaggcgag ttacatgatc ccccatgttg   1260
tgcaaaaaag cggttagctc cttcggtcct ccgatcgttg tcagaagtaa gttggccgca   1320
gtgttatcac tcatggttat ggcagcactg cataattctc ttactgtcat gccatccgta   1380
agatgctttt ctgtgactgg tgagtactca accaagtcat tctgagaata gtgtatgcgg   1440
cgaccgagtt gctcttgccc ggcgtcaata cgggataata ccgcgccaca tagcagaact   1500
ttaaaagtgc tcatcattgg aaaacgttct cggggcgaaa actctcaag gatcttaccg    1560 ctgttgagat ccagttcgat gtaacccact cgtgcaccca actgatcttc agcatctttt   1620
actttcacca gcgtttctgg gtgagcaaaa acaggaaggc aaaatgccgc aaaaaaggga   1680
ataagggcga cacggaaatg ttgaatactc atactcttcc tttttcaata ttattgaagc   1740
atttatcagg gttattgtct catgagcgga tacatatttg aatgtattta gaaaaataaa   1800
caaatagggg ttccgcgcac atttccccga aaagtgccac ctgacaaact tggtaccata   1860
actagttcgg cgcgccaatc tcgcctattc atggtgtata aaagttcaac atccaaagct   1920
agaacttttg gaaagagaaa gaatgtccga ataggggcacg gcgtgccgta ttgttggagt   1980
ggactagcag aaagtgagga aggcacagga tgagtttcct cgagacacat agcttcagcg   2040
tcgtgtaggc taggcagagg tgagttttct cgagacatac cttcagcgtc gtcttcactg   2100
tcacagtcaa ctgacagtaa tcgttgatcc ggagagattc aaaattcaat ctgtttggac   2160
ctggataaga cacaagagcg acatcctgac atgaacgccg taaacagcaa atcctggttg   2220
aacacgtatc cttttggggg cctccagcta cgacgctcgc cccagctggg gcttccttac   2280
tatacacagc gcatatttca cggttgccag aaccatgggc gatcctaaaa agaaacgtaa   2340
ggtcatcgat aaggagaccg ccgctgccaa gttcgagaga cagcacatgg acagcatcga   2400
tatcgccgac cccattcgtt cgcgcacacc aagtcctgcc cgcgagcttc tgcccggacc   2460
ccaacccgat ggggttcagc cgactgcaga tcgtggggtg tctccgcctg ccggcggccc   2520
cctggatggc ttgccggctc ggcggacgat gtccggacc cggctgccat ctcccctgc     2580 cccctcacct gcgttctcgg cgggcagctt cagtgacctg ttacgtcagt tcgatccgtc   2640
actttttaat acatcgcttt ttgattcatt gcctcccttc ggcgctcacc atacagaggc   2700
tgccacaggc gagtgggatg aggtgcaatc gggtctgcgg gcagccgacg ccccccacc    2760 caccatgcgc gtggctgtca ctgccgcgcg gccccgcgc gccaagccgg cgccgcgacg    2820
acgtgctgcg caaccctccg acgcttcgcc ggcggcgcag gtggatctac gcacgctcgg   2880
ctacagccag cagcaacagg agaagatcaa accgaaggtt cgttcgacag tggcgcagca   2940
ccacgaggca ctggtcggcc acgggtttac acacgcgcac atcgttgcgt taagccaaca   3000
cccggcagcg ttagggaccg tcgctgtcaa gtatcaggac atgatcgcag cgttgccaga   3060
ggcgacacac gaagcgatcg ttggcgtcgg caaacagtgg tccggcgcac gcgctctgga   3120
ggccttgctc acggtggcgg gagagttgag aggtccaccg ttacagttgg acacaggcca   3180
acttctcaag attgcaaaac gtggcggcgt gaccgcagtg gaggcagtgc atgcatggcg   3240
caatgcactg acgggtgccc cgctcaactt gacccccag caggtggtgg ccatcgccag    3300
caatggcggt ggcaagcagg cgctggagac ggtccagcgg ctgttgccgg tgctgtgcca   3360
ggcccacggc ttgaccccgg agcaggtggt ggccatcgcc agccacgatg gcggcaagca   3420
```

```
ggcgctggag acggtccagc ggctgttgcc ggtgctgtgc caggcccacg gcttgacccc    3480
ggagcaggtg gtggccatcg ccagccacga tggcggcaag caggcgctgg agacggtcca    3540
gcggctgttg ccggtgctgt gccaggccca cggcttgacc ccggagcagg tggtggccat    3600
cgccagccac gatggcggca agcaggcgct ggagacggtc cagcggctgt tgccggtgct    3660
gtgccaggcc cacggcttga ccccggagca ggtggtggcc atcgccagcc acgatggcgg    3720
caagcaggcg ctggagacgg tccagcggct gttgccggtg ctgtgccagg cccacggctt    3780
gaccccggag caggtggtgg ccatcgccag caatattggt ggcaagcagg cgctggagac    3840
ggtgcaggcg ctgttgccgg tgctgtgcca ggcccacggc ttgacccccc agcaggtggt    3900
ggccatcgcc agcaataatg gtggcaagca ggcgctggag acggtccagc ggctgttgcc    3960
ggtgctgtgc caggcccacg gcttgacccc ccagcaggtg gtggccatcg ccagcaatgg    4020
cggtggcaag caggcgctgg agacggtcca gcggctgttg ccggtgctgt gccaggccca    4080
cggcttgacc ccccagcagg tggtggccat cgccagcaat ggcggtggca agcaggcgct    4140
ggagacggtc cagcggctgt tgccggtgct gtgccaggcc cacggcttga ccccggagca    4200
ggtggtggcc atcgccagca atattggtgg caagcaggcg ctggagacgg tgcaggcgct    4260
gttgccggtg ctgtgccagg cccacggctt gaccccggag caggtggtgg ccatcgccag    4320
ccacgatggc ggcaagcagg cgctggagac ggtccagcgg ctgttgccgg tgctgtgcca    4380
ggcccacggc ttgaccccgg agcaggtggt ggccatcgcc agccacgatg gcggcaagca    4440
ggcgctggag acggtccagc ggctgttgcc ggtgctgtgc caggcccacg gcttgacccc    4500
ccagcaggtg gtggccatcg ccagcaataa tggtggcaag caggcgctgg agacggtcca    4560
gcggctgttg ccggtgctgt gccaggccca cggcttgacc ccggagcagg tggtggccat    4620
cgccagccac gatggcggca agcaggcgct ggagacggtc cagcggctgt tgccggtgct    4680
gtgccaggcc cacggcttga cccccccagca ggtggtggcc atcgccagca atggcggtgg    4740
caagcaggcg ctggagacgg tccagcggct gttgccggtg ctgtgccagg cccacggctt    4800 gaccccctcag caggtggtgg ccatcgccag caatggcggc ggcaggccgg cgctggagag    4860
cattgttgcc cagttatctc gccctgatcc ggcgttggcc gcgttgacca acgaccacct    4920
cgtcgccttg gcctgcctcg gcgggcgtcc tgcgctggat gcagtgaaaa agggattggg    4980
ggatcctatc agccgttccc agctggtgaa gtccgagctg gaggagaaga atccgagtt    5040 gaggcacaag ctgaagtacg tgccccacga gtacatcgag ctgatcgaga tcgcccggaa    5100 cagcaccccag gaccgtatcc tggagatgaa ggtgatggag ttcttcatga aggtgtacgg    5160 ctacagggc aagcacctgg gcggctccag gaagcccgac ggcgccatct acaccgtggg    5220
ctcccccatc gactacggcg tgatcgtgga caccaaggcc tactccggcg gctacaacct    5280
gcccatcggc caggccgacg aaatgcagag gtacgtggag gagaaccaga ccaggaacaa    5340
gcacatcaac cccaacgagt ggtggaaggt gtaccctctc agcgtgaccg agttcaagtt    5400
cctgttcgtg tccggccact tcaagggcaa ctacaaggcc cagctgacca ggctgaacca    5460
catcaccaac tgcaacggcg ccgtgctgtc cgtggaggag ctcctgatcg gcggcgagat    5520
gatcaaggcc ggcaccctga ccctggagga ggtgaggagg aagttcaaca acggcgagat    5580
caacttcgcg gccgactgat aactcgagcg atcctctaga cgagctcctc gagcctgcag    5640
cagctgaagc tttaagatcc aatggcaagg accaagtgct ggaacttgtt ttgctttagc    5700
agatctagat cgagctacct cgactttggc tgggacactt tcagtgagga caagaagctt    5760
cagaagcgtg ctatcgaact caaccaggga cgtgcggcac aaatgggcat ccttgctctc    5820
```

```
atggtgcacg aacagttggg agtctctatc cttccttaaa aatttaattt tcattagttg    5880
cagtcactcc gctttggttt cacagtcagg aataacacta gctcgtcttc atatcctgca    5940
```

<210> SEQ ID NO 25
<211> LENGTH: 50
<212> TYPE: DNA
<213> ORGANISM: artificial sequence
<220> FEATURE:
<223> OTHER INFORMATION: G3PDH target

<400> SEQUENCE: 25

```
ttctgaccaa ctcgataaag tatgcatcat cggtagcggt aactggggaa               50
```

<210> SEQ ID NO 26
<211> LENGTH: 26
<212> TYPE: DNA
<213> ORGANISM: artificial sequence
<220> FEATURE:
<223> OTHER INFORMATION: ScreenHA_For

<400> SEQUENCE: 26

```
acccatacga tgttccagat tacgct                                         26
```

<210> SEQ ID NO 27
<211> LENGTH: 24
<212> TYPE: DNA
<213> ORGANISM: artificial sequence
<220> FEATURE:
<223> OTHER INFORMATION: Screen TALEN_Rev

<400> SEQUENCE: 27

```
aatcttgaga agttggcctg tgtc                                           24
```

<210> SEQ ID NO 28
<211> LENGTH: 62
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (31)..(32)
<223> OTHER INFORMATION: primer G3PDH_For ; n is a or c or t or g
<220> FEATURE:
<221> NAME/KEY: misc_feature
<222> LOCATION: (33)..(40)
<223> OTHER INFORMATION: n is a, c, g, or t

<400> SEQUENCE: 28

```
ccatctcatc cctgcgtgtc tccgactcag nnnnnnnnnn tctgctactg ctcatccgca    60
cc                                                                   62
```

<210> SEQ ID NO 29
<211> LENGTH: 53
<212> TYPE: DNA
<213> ORGANISM: artificial sequence
<220> FEATURE:
<223> OTHER INFORMATION: primer G3PDH_Rev

<400> SEQUENCE: 29

```
cctatcccct gtgtgccttg gcagtctcag tcgcgacagg cttctgctag atc            53
```

<210> SEQ ID NO 30
<211> LENGTH: 1308
<212> TYPE: DNA

<213> ORGANISM: Phaeodactylum tricornutum

<400> SEQUENCE: 30

| | | | | | |
|---|---|---|---|---|---|
| atgaagcttc | atatcgcacc | acctcttatt | atctcggcct | acgtgttttc | tgtatccatt | 60 |
| ttccacaaca | ctgttaatgc | cttttcgttg | cgcataccga | gtaccacag | gactgttttc | 120 |
| cttccgcaag | tgacgttgaa | tgccaaaaga | tggatggtag | caacgggggt | agaaacaaac | 180 |
| gctgctgtgg | caactccaga | aaatgacgaa | atccatcctc | gacgggattg | gactcacgac | 240 |
| gagccgccca | agttgagcga | agtgaagcgc | atgcttcccc | aagaagcctt | ccacattgat | 300 |
| acagcaacgt | cacttttta | ttttgcggtg | gattttatcg | ctgtagcatc | cactatggga | 360 |
| tttctgaact | ccgtcgtctc | atccgatatc | tacctttcct | tccctatctg | gggcaagttc | 420 |
| ttggctgtag | cccctttaca | gattttgacc | ggttttgcga | tgtggtgcat | gtggtgtatc | 480 |
| ggccacgatg | ccggtcacac | tactgtatcc | aaagaccggc | ggttcggcgc | tcttattaat | 540 |
| agggtagttg | gcgaagtggc | gcattccgcg | atttgcttaa | cgccttcgt | tccctgggcc | 600 |
| aagtctcatc | tgaagcatca | catgggacac | aaccacttga | cgcgtgacta | ctcgcatcaa | 660 |
| tggtttatcc | gagaagaacg | agagtcgcta | catccactta | ttcaactgag | tcatgcgacg | 720 |
| cgaaatttac | agttaccgat | actttacctc | gtttatctct | tatttggggt | tcccgatgga | 780 |
| ggacacgtcg | tttttacgg | acgcatgtgg | gagcagtcta | ccgcgaagga | aaaggccgat | 840 |
| gccgcggtgt | ccgttatcgt | atcccttgtc | acggccggtt | ctctgtggat | caatatgggt | 900 |
| ttggcaaatt | tcttcgttgt | ttgcatggtc | ccgtggttgg | tcctgtcatt | ttggctcttc | 960 |
| atggtcacct | atctacagca | ccactccgac | atggttac | tctatacgga | cgagacctgg | 1020 |
| agctttgaac | ggggcgcctt | tcaaactgtt | gatcgtgatt | atggaacgtg | gatcaatcgc | 1080 |
| atgtcacatc | acatgatgga | tgggcatttg | gtccatcacc | tgtttttcac | tcgggttccg | 1140 |
| cattacaggc | tcgaagaagc | gacgaaatcc | ttatatgcag | tcatggctgc | gcgagggcag | 1200 |
| tcacacctga | ttaaaacgat | tgatacgccc | gactttacgc | aggagattgc | caaacaattc | 1260 |
| gacaaaaact | ggttctttgt | caacgaaaat | cagattgtac | gcaagtaa | | 1308 |

<210> SEQ ID NO 31
<211> LENGTH: 5922
<212> TYPE: DNA
<213> ORGANISM: artificial sequence
<220> FEATURE:
<223> OTHER INFORMATION: pCLS23158 (TALEN Omega3 desaturase)

<400> SEQUENCE: 31

| | | | | | |
|---|---|---|---|---|---|
| gggtacgttt | aaacgtatta | attaagacct | agcatgtgag | caaaaggcca | gcaaaaggcc | 60 |
| aggaaccgta | aaaaggccgc | gttgctggcg | ttttccata | ggctccgccc | ccctgacgag | 120 |
| catcacaaaa | atcgacgctc | aagtcagagg | tggcgaaacc | cgacaggact | ataaagatac | 180 |
| caggcgtttc | cccctggaag | ctccctcgtg | cgctctcctg | ttccgaccct | gccgcttacc | 240 |
| ggatacctgt | ccgcctttct | cccttcggga | agcgtggcgc | tttctcatag | ctcacgctgt | 300 |
| aggtatctca | gttcggtgta | ggtcgttcgc | tccaagctgg | gctgtgtgca | cgaaccccc | 360 |
| gttcagcccg | accgctgcgc | cttatccggt | aactatcgtc | ttgagtccaa | cccggtaaga | 420 |
| cacgacttat | cgccactggc | agcagccact | ggtaacagga | ttagcagagc | gaggtatgta | 480 |
| ggcggtgcta | cagagttctt | gaagtggtgg | cctaactacg | gctacactag | aaggacagta | 540 |
| tttggtatct | gcgctctgct | gaagccagtt | accttcggaa | aaagagttgg | tagctcttga | 600 |
| tccggcaaac | aaaccaccgc | tggtagcggt | ggttttttg | tttgcaagca | gcagattacg | 660 |

```
cgcagaaaaa aaggatctca agaagatcct ttgatctttt ctacggggtc tgacgctcag    720
tggaacgaaa actcacgtta agggattttg gtcatgagat tatcaaaaag gatcttcacc    780
tagatccttt taaattaaaa atgaagtttt aaatcaatct aaagtatata tgagtaaact    840
tggtctgaca gttaccaatg cttaatcagt gaggcaccta tctcagcgat ctgtctattt    900
cgttcatcca tagttgcctg actccccgtc gtgtagataa ctacgatacg ggagggctta    960
ccatctggcc ccagtgctgc aatgataccg cgagacccac gctcaccggc tccagattta   1020
tcagcaataa accagccagc cggaagggcc gagcgcagaa gtggtcctgc aactttatcc   1080
gcctccatcc agtctattaa ttgttgccgg gaagctagag taagtagttc gccagttaat   1140
agtttgcgca acgttgttgc cattgctaca ggcatcgtgg tgtcacgctc gtcgtttggt   1200
atggcttcat tcagctccgg ttcccaacga tcaaggcgag ttacatgatc ccccatgttg   1260
tgcaaaaaag cggttagctc cttcggtcct ccgatcgttg tcagaagtaa gttggccgca   1320
gtgttatcac tcatggttat ggcagcactg cataattctc ttactgtcat gccatccgta   1380
agatgctttt ctgtgactgg tgagtactca accaagtcat tctgagaata gtgtatgcgg   1440
cgaccgagtt gctcttgccc ggcgtcaata cgggataata ccgcgccaca tagcagaact   1500
ttaaaagtgc tcatcattgg aaaacgttct tcggggcgaa aactctcaag gatcttaccg   1560
ctgttgagat ccagttcgat gtaacccact cgtgcaccca actgatcttc agcatctttt   1620
actttcacca gcgtttctgg gtgagcaaaa acaggaaggc aaaatgccgc aaaaaaggga   1680
ataagggcga cacggaaatg ttgaatactc atactcttcc tttttcaata ttattgaagc   1740
atttatcagg gttattgtct catgagcgga tacatatttg aatgtattta gaaaaataaa   1800 caaataggg ttccgcgcac atttccccga aaagtgccac ctgacaaact tggtaccata   1860
actagttcgg cgcgccaatc tcgcctattc atggtgtata aaagttcaac atccaaagct   1920
agaacttttg gaaagagaaa gaatgtccga ataggggacg gcgtgccgta ttgttggagt   1980
ggactagcag aaagtgagga aggcacagga tgagtttcct cgagacacat agcttcagcg   2040
tcgtgtaggc taggcagagg tgagttttct cgagacatac cttcagcgtc gtcttcactg   2100
tcacagtcaa ctgacagtaa tcgttgatcc ggagagattc aaaattcaat ctgtttggac   2160
ctggataaga cacaagagcg acatcctgac atgaacgccg taaacagcaa atcctggttg   2220
aacacgtatc cttttggggg cctccagcta cgacgctcgc cccagctggg gcttccttac   2280
tatacacagc gcatatttca cggttgccag aaccatgggc gatcctaaaa agaaacgtaa   2340
ggtcatcgat tacccatacg atgttccaga ttacgctatc gatatcgccg accccattcg   2400
ttcgcgcaca ccaagtcctg cccgcgagct tctgcccgga ccccaacccg atggggttca   2460
gccgactgca gatcgtgggg tgtctccgcc tgccggcggc ccctggatg gcttgccggc   2520 tcggcggacg atgtcccgga cccggctgcc atctcccct gccccctcac ctgcgttctc   2580
ggcgggcagc ttcagtgacc tgttacgtca gttcgatccg tcacttttta atacatcgct   2640 tttgattca ttgcctccct tcggcgctca ccatacagag gctgccacag gcgagtggga   2700
tgaggtgcaa tcgggtctgc gggcagccga cgcccccca cccaccatgc gcgtggctgt   2760
cactgccgcg cggcccccgc gcgccaagcc ggcgccgcga cgacgtgctg cgcaaccctc   2820
cgacgcttcg ccggcggcgc aggtggatct acgcacgctc ggctacagcc agcagcaaca   2880
ggagaagatc aaaccgaagg ttcgttcgac agtggcgcag caccacgagg cactggtcgg   2940
ccacgggttt acacacgcgc acatcgttgc gttaagccaa caccggcag cgttagggac   3000
```

```
cgtcgctgtc aagtatcagg acatgatcgc agcgttgcca gaggcgacac acgaagcgat    3060
cgttggcgtc ggcaaacagt ggtccggcgc acgcgctctg gaggccttgc tcacggtggc    3120
gggagagttg agaggtccac cgttacagtt ggacacaggc caacttctca agattgcaaa    3180
acgtggcggc gtgaccgcag tggaggcagt gcatgcatgg cgcaatgcac tgacgggtgc    3240
cccgctcaac ttgacccccc agcaggtggt ggccatcgcc agcaatggcg gtggcaagca    3300
ggcgctggag acgtccagc ggctgttgcc ggtgctgtgc caggcccacg gcttgacccc    3360
ccagcaggtg gtggccatcg ccagcaatgg cggtggcaag caggcgctgg agacggtcca    3420
gcggctgttg ccggtgctgt gccaggccca cggcttgacc cccagcagg tggtggccat    3480 cgccagcaat ggcggtggca agcaggcgct ggagacggtc agcggctgt tgccggtgct    3540 gtgccaggcc cacggcttga ccccggagca ggtggtggcc atcgccagcc acgatggcgg    3600
caagcaggcg ctggagacgg tccagcggct gttgccggtc tgtgccagg cccacggctt    3660 gaccccggag caggtggtgg ccatcgccag ccacgatggc ggcaagcagg cgctggagac    3720
ggtccagcgg ctgttgccgg tgctgtgcca ggcccacggc ttgaccccgg agcaggtggt    3780
ggccatcgcc agcaatattg gtggcaagca ggcgctggag acggtgcagg cgctgttgcc    3840
ggtgctgtgc caggcccacg gcttgacccc ggagcaggtg gtggccatcg ccagccacga    3900
tggcggcaag caggcgctgg agacggtcca gcggctgttg ccggtgctgt gccaggccca    3960
cggcttgacc ccggagcagg tggtggccat cgccagcaat attggtggca agcaggcgct    4020
ggagacggtg caggcgctgt gccggtgct gtgccaggcc cacggcttga ccccggagca    4080
ggtggtggcc atcgccagca atattggtgg caagcaggcg ctggagacgg tgcaggcgct    4140
gttgccggtg ctgtgccagg cccacggctt gaccccggag caggtggtgg ccatcgccag    4200
ccacgatggc ggcaagcagg cgctggagac ggtccagcgg ctgttgccgg tgctgtgcca    4260
ggcccacggc ttgaccccgg agcaggtggt ggccatcgcc agcaatattg gtggcaagca    4320
ggcgctggag acgtgcagg cgctgttgcc ggtgctgtgc caggcccacg gcttgacccc    4380
ggagcaggtg gtggccatcg ccagccacga tggcggcaag caggcgctgg agacggtcca    4440
gcggctgttg ccggtgctgt gccaggccca cggcttgacc cccagcagg tggtggccat    4500 cgccagcaat ggcggtggca agcaggcgct ggagacggtc agcggctgt tgccggtgct    4560 gtgccaggcc cacggcttga ccccccagca ggtggtggcc atcgccagca ataatggtgg    4620
caagcaggcg ctggagacgg tccagcggct gttgccggtg ctgtgccagg cccacggctt    4680
gaccccccag caggtggtgg ccatcgccag caatggcggt ggcaagcagg cgctggagac    4740
ggtccagcgg ctgttgccgg tgctgtgcca ggcccacggc ttgaccccctc agcaggtggt    4800 ggccatcgcc agcaatggcg gcggcaggcc ggcgctggag agcattgttg cccagttatc    4860
tcgccctgat ccggcgttgg ccgcgttgac caacgaccac ctcgtcgcct tggcctgcct    4920
cggcgggcgt cctgcgctgg atgcagtgaa aaagggattg ggggatccta tcagccgttc    4980
ccagctggtg aagtccgagc tggaggagaa gaaatccgag ttgaggcaca agctgaagta    5040
cgtgccccac gagtacatcg agctgatcga gatcgcccgg aacagcaccc aggaccgtat    5100
cctggagatg aaggtgatgg agttcttcat gaaggtgtac ggctacaggg gcaagcacct    5160
gggcggctcc aggaagcccg acggcgccat ctacaccgtg gcctccccca tcgactacgg    5220
cgtgatcgtg gacaccaagg cctactccgg cggctacaac ctgcccatcg gccaggccga    5280
cgaaatgcag aggtacgtgg aggagaacca gaccaggaac aagcacatca ccccaacga    5340 gtggtggaag gtgtacccct ccagcgtgac cgagttcaag ttcctgttcg tgtccggcca    5400
```

| | |
|---|---|
| cttcaagggc aactacaagg cccagctgac caggctgaac cacatcacca actgcaacgg | 5460 |
| cgccgtgctg tccgtggagg agctcctgat cggcggcgag atgatcaagg ccggcaccct | 5520 |
| gaccctggag gaggtgagga ggaagttcaa caacggcgag atcaacttcg cggccgactg | 5580 |
| ataactcgag cgatcctcta gacgagctcc tcgagcctgc agcagctgaa gctttaagat | 5640 |
| ccaatggcaa ggaccaagtg ctggaacttg ttttgcttta gcagatctag atcgagctac | 5700 |
| ctcgactttg gctgggacac tttcagtgag gacaagaagc ttcagaagcg tgctatcgaa | 5760 |
| ctcaaccagg gacgtgcggc acaaatgggc atccttgctc tcatggtgca cgaacagttg | 5820 |
| ggagtctcta tccttcctta aaaatttaat tttcattagt tgcagtcact ccgctttggt | 5880 |
| ttcacagtca ggaataacac tagctcgtct tcatatcctg ca | 5922 |

<210> SEQ ID NO 32
<211> LENGTH: 5940
<212> TYPE: DNA
<213> ORGANISM: artificial sequence
<220> FEATURE:
<223> OTHER INFORMATION: pCLS23162 (TALEN Omega3 desaturase)

<400> SEQUENCE: 32

| | |
|---|---|
| gggtacgttt aaacgtatta attaagacct agcatgtgag caaaaggcca gcaaaaggcc | 60 |
| aggaaccgta aaaaggccgc gttgctggcg ttttttccata ggctccgccc ccctgacgag | 120 |
| catcacaaaa atcgacgctc aagtcagagg tggcgaaacc cgacaggact ataaagatac | 180 |
| caggcgtttc ccctggaag ctccctcgtg cgctctcctg ttccgaccct gccgcttacc | 240 |
| ggatacctgt ccgcctttct cccttcggga agcgtggcgc tttctcatag ctcacgctgt | 300 |
| aggtatctca gttcggtgta ggtcgttcgc tccaagctgg gctgtgtgca cgaaccccc | 360 |
| gttcagcccg accgctgcgc cttatccggt aactatcgtc ttgagtccaa cccggtaaga | 420 |
| cacgacttat cgccactggc agcagccact ggtaacagga ttagcagagc gaggtatgta | 480 |
| ggcggtgcta cagagttctt gaagtggtgg cctaactacg gctacactag aaggacagta | 540 |
| tttggtatct gcgctctgct gaagccagtt accttcggaa aaagagttgg tagctcttga | 600 |
| tccggcaaac aaaccaccgc tggtagcggt ggtttttttg tttgcaagca gcagattacg | 660 |
| cgcagaaaaa aaggatctca agaagatcct ttgatctttt ctacggggtc tgacgctcag | 720 |
| tggaacgaaa actcacgtta agggattttg gtcatgagat tatcaaaaag gatcttcacc | 780 |
| tagatccttt taaattaaaa atgaagtttt aaatcaatct aaagtatata tgagtaaact | 840 |
| tggtctgaca gttaccaatg cttaatcagt gaggcaccta tctcagcgat ctgtctattt | 900 |
| cgttcatcca tagttgcctg actccccgtc gtgtagataa ctacgatacg ggagggctta | 960 |
| ccatctggcc ccagtgctgc aatgataccg cgagacccac gctcaccggc tccagattta | 1020 |
| tcagcaataa accagccagc cggaagggcc gagcgcagaa gtggtcctgc aactttatcc | 1080 |
| gcctccatcc agtctattaa ttgttgccgg gaagctagag taagtagttc gccagttaat | 1140 |
| agtttgcgca acgttgttgc cattgctaca ggcatcgtgg tgtcacgctc gtcgtttggt | 1200 |
| atggcttcat tcagctccgg ttcccaacga tcaaggcgag ttacatgatc ccccatgttg | 1260 |
| tgcaaaaaag cggttagctc cttcggtcct ccgatcgttg tcagaagtaa gttggccgca | 1320 |
| gtgttatcac tcatggttat ggcagcactg cataattctc ttactgtcat gccatccgta | 1380 |
| agatgctttt ctgtgactgg tgagtactca accaagtcat tctgagaata gtgtatgcgg | 1440 |
| cgaccgagtt gctcttgccc ggcgtcaata cgggataata ccgcgccaca tagcagaact | 1500 |

```
ttaaaagtgc tcatcattgg aaaacgttct tcggggcgaa aactctcaag gatcttaccg    1560
ctgttgagat ccagttcgat gtaacccact cgtgcaccca actgatcttc agcatctttt    1620
actttcacca gcgtttctgg gtgagcaaaa acaggaaggc aaaatgccgc aaaaaaggga    1680
ataagggcga cacggaaatg ttgaatactc atactcttcc tttttcaata ttattgaagc    1740
atttatcagg gttattgtct catgagcgga tacatatttg aatgtattta gaaaaataaa    1800
caaatagggg ttccgcgcac atttccccga aaagtgccac ctgacaaact tggtaccata    1860
actagttcgg cgcgccaatc tcgcctattc atggtgtata aaagttcaac atccaaagct    1920
agaacttttg gaaagagaaa gaatgtccga ataggcacg gcgtgccgta ttgttggagt    1980
ggactagcag aaagtgagga aggcacagga tgagtttcct cgagacacat agcttcagcg    2040
tcgtgtaggc taggcagagg tgagttttct cgagacatac cttcagcgtc gtcttcactg    2100
tcacagtcaa ctgacagtaa tcgttgatcc ggagagattc aaaattcaat ctgtttggac    2160
ctggataaga cacaagagcg acatcctgac atgaacgccg taaacagcaa atcctggttg    2220
aacacgtatc cttttggggg cctccagcta cgacgctcgc cccagctggg gcttccttac    2280
tatacacagc gcatatttca cggttgccag aaccatgggc gatcctaaaa agaaacgtaa    2340
ggtcatcgat aaggagaccg ccgctgccaa gttcgagaga cagcacatgg acagcatcga    2400
tatcgccgac cccattcgtt cgcgcacacc aagtcctgcc cgcgagcttc tgcccggacc    2460
ccaacccgat ggggttcagc cgactgcaga tcgtggggtg tctccgcctg ccggcggccc    2520
cctggatggc ttgccggctc ggcggacgat gtcccggacc cggctgccat ctcccctgc     2580 cccctcacct gcgttctcgg cgggcagctt cagtgacctg ttacgtcagt tcgatccgtc    2640 acttttaat acatcgcttt ttgattcatt gcctcccttc ggcgctcacc atacagaggc     2700
tgccacaggc gagtgggatg aggtgcaatc gggtctgcgg gcagccgacg ccccccccacc   2760 caccatgcgc gtggctgtca ctgccgcgcg gcccccgcgc gccaagccgg cgccgcgacg    2820
acgtgctgcg caaccctccg acgcttcgcc ggcggcgcag gtggatctac gcacgctcgg    2880
ctacagccag cagcaacagg agaagatcaa accgaaggtt cgttcgacag tggcgcagca    2940
ccacgaggca ctggtcggcc acgggtttac acacgcgcac atcgttgcgt taagccaaca    3000
cccggcagcg ttagggaccg tcgctgtcaa gtatcaggac atgatcgcag cgttgccaga    3060
ggcgacacac gaagcgatcg ttggcgtcgg caaacagtgg tccggcgcac gcgctctgga    3120
ggccttgctc acggtggcgg gagagttgag aggtccaccg ttacagttgg acacaggcca    3180
acttctcaag attgcaaaac gtggcggcgt gaccgcagtg gaggcagtgc atgcatggcg    3240
caatgcactg acgggtgccc cgctcaactt gaccccccag caggtggtgg ccatcgccag    3300
caataatggt ggcaagcagg cgctggagac ggtccagcgg ctgttgccgg tgctgtgcca    3360
ggcccacggc ttgaccccc agcaggtggt ggccatcgcc agcaataatg gtggcaagca    3420
ggcgctggag acggtccagc ggctgttgcc ggtgctgtgc caggcccacg gcttgacccc    3480
ccagcaggtg gtgccatcg ccagcaataa tggtggcaag caggcgctgg agacggtcca    3540
gcggctgttg ccggtgctgt gccaggccca cggcttgacc cccagcagg tggtggccat    3600 cgccagcaat ggcggtggca agcaggcgct ggagacggtc agcggctgt tgccggtgct    3660 gtgccaggcc cacggcttga ccccggagca ggtggtggcc atcgccagca atattggtgg    3720
caagcaggcg ctggagacgg tgcaggcgct gttgccggtg ctgtgccagg cccacggctt    3780
gaccccggag caggtggtgg ccatcgccag ccacgatggc ggcaagcagg cgctggagac    3840
ggtccagcgg ctgttgccgg tgctgtgcca ggcccacggc ttgacccccc agcaggtggt    3900
```

```
ggccatcgcc agcaatggcg gtggcaagca ggcgctggag acggtccagc ggctgttgcc   3960
ggtgctgtgc caggcccacg gcttgacccc ggagcaggtg gtggccatcg ccagccacga   4020
tggcggcaag caggcgctgg agacggtcca gcggctgttg ccggtgctgt gccaggccca   4080
cggcttgacc ccccagcagg tggtggccat cgccagcaat aatggtggca agcaggcgct   4140
ggagacggtc cagcggctgt tgccggtgct gtgccaggcc cacggcttga ccccccagca   4200
ggtggtggcc atcgccagca ataatggtgg caagcaggcg ctggagacgg tccagcggct   4260
gttgccggtg ctgtgccagg cccacggctt gaccccccag caggtggtgg ccatcgccag   4320
caatggcggt ggcaagcagg cgctggagac ggtccagcgg ctgttgccgg tgctgtgcca   4380
ggcccacggc ttgaccccgg agcaggtggt ggccatcgcc agcaatattg gtggcaagca   4440
ggcgctggag acggtgcagg cgctgttgcc ggtgctgtgc caggcccacg gcttgacccc   4500
ccagcaggtg gtggccatcg ccagcaatgg cggtggcaag caggcgctgg agacggtcca   4560
gcggctgttg ccggtgctgt gccaggccca cggcttgacc ccccagcagg tggtggccat   4620
cgccagcaat aatggtggca agcaggcgct ggagacggtc cagcggctgt tgccggtgct   4680
gtgccaggcc cacggcttga ccccggagca ggtggtggcc atcgccagcc acgatggcgg   4740
caagcaggcg ctggagacgg tccagcggct gttgccggtg ctgtgccagg cccacggctt   4800
gacccctcag caggtggtgg ccatcgccag caatggcggc ggcaggccgg cgctggagag   4860
cattgttgcc cagttatctc gccctgatcc ggcgttggcc gcgttgacca acgaccacct   4920
cgtcgccttg gcctgcctcg gcgggcgtcc tgcgctggat gcagtgaaaa agggattggg   4980
ggatcctatc agccgttccc agctggtgaa gtccgagctg gaggagaaga atccgagtt   5040 gaggcacaag ctgaagtacg tgccccacga gtacatcgag ctgatcgaga tcgcccggaa   5100
cagcacccag gaccgtatcc tggagatgaa ggtgatggag ttcttcatga aggtgtacgg   5160 ctacagggc aagcacctgg gcggctccag gaagcccgac ggcgccatct acaccgtggg   5220
ctcccccatc gactacggcg tgatcgtgga caccaaggcc tactccggcg gctacaacct   5280
gcccatcggc caggccgacg aaatgcagag gtacgtggag gagaaccaga ccaggaacaa   5340
gcacatcaac cccaacgagt ggtggaaggt gtacccctcc agcgtgaccg agttcaagtt   5400
cctgttcgtg tccggccact tcaagggcaa ctacaaggcc cagctgacca ggctgaacca   5460
catcaccaac tgcaacggcg ccgtgctgtc cgtggaggag ctcctgatcg gcggcgagat   5520
gatcaaggcc ggcacccctga ccctggagga ggtgaggagg aagttcaaca acggcgagat   5580
caacttcgcg gccgactgat aactcgagcg atcctctaga cgagctcctc gagcctgcag   5640
cagctgaagc tttaagatcc aatggcaagg accaagtgct ggaacttgtt ttgctttagc   5700
agatctagat cgagctacct cgactttggc tgggacactt tcagtgagga caagaagctt   5760
cagaagcgtg ctatcgaact caaccaggga cgtgcggcac aaatgggcat ccttgctctc   5820
atggtgcacg aacagttggg agtctctatc cttccttaaa aatttaattt tcattagttg   5880
cagtcactcc gctttggttt cacagtcagg aataacacta gctcgtcttc atatcctgca   5940
```

<210> SEQ ID NO 33
<211> LENGTH: 49
<212> TYPE: DNA
<213> ORGANISM: artificial sequence
<220> FEATURE:
<223> OTHER INFORMATION: Omega3 desaturase target

<400> SEQUENCE: 33 tttttccacaa cactgttaat gccttttcgt tgcgcatacc gagtaccca                49

<210> SEQ ID NO 34
<211> LENGTH: 61
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (31)..(32)
<223> OTHER INFORMATION: Deep seq Omega3 desaturase_For ; n is a or c or
   t or g
<220> FEATURE:
<221> NAME/KEY: misc_feature
<222> LOCATION: (33)..(40)
<223> OTHER INFORMATION: n is a, c, g, or t

<400> SEQUENCE: 34
ccatctcatc cctgcgtgtc tccgactcag nnnnnnnnnn gcgtgtgctc acctgttgtc    60
c                                                                   61

<210> SEQ ID NO 35
<211> LENGTH: 52
<212> TYPE: DNA
<213> ORGANISM: artificial sequence
<220> FEATURE:
<223> OTHER INFORMATION: Deep seqOmega3 desaturase_Rev

<400> SEQUENCE: 35
cctatcccct gtgtgccttg gcagtctcag aagcatgcgc ttcacttcgc tc            52

<210> SEQ ID NO 36
<211> LENGTH: 897
<212> TYPE: DNA
<213> ORGANISM: Phaeodactylum tricornutum

<400> SEQUENCE: 36
tctgaaaaca agcaattgcc ggtggtcttt gcccatggga tgggagattc gtgctttaat    60
tctggcatgc aacacgttgc gcagctggcc tccgaatggc tcagtgagga ctttggtccg   120
gacagatcga atgtgtatag cgtatgcgtt ccgaccggtg cgactcaagc agaagatacc   180
aagaacggtt actttctgag catggatgct tcggtggaag tctttgcgga aggtgttagg   240
gcggacccac gactgagcga tggctttcac gccattgggt tttcgcaggg caacaacgtc   300
attcggggct acattgccaa acataacacg cctaccgttg acacatttat atccatcaat   360
ggggtgaacg cagggatcgg tgctgtgccg tattgtcgtc ctagtgaaac tgccatgggt   420
gctgtgcgac tgggtggaat gtgcgattta ctcatggaac aggcctcgcg gagtgcctac   480
actgaatttg cacaagagca ttcctttcaa gccaactact ggcgcgatcc acggccaact   540
gcctttccgc tctaccaaaa gtacggacag ctcgctgctt ggaataacga agcgggacta   600
gtgaacgaaa ctctgaaaac gaactggggt aagacctccg ctttcgtgtg ggtgttggcc   660
accgaagatg gattggtgtg gcccaaagaa ggagagcaat gggggcagcc ggattcgaaa   720 gatcctttc atgtgatctt atccataaac gaaacgacct ggtacaaaga ggacttgttt   780
ggcctccgaa ctgcaaatga attgggaaag aattatttcg aatcgttcga gggggaccat   840
ttgcagtttg aatctgccga tctggaacga tgggtaaaga cctacctcaa gaactag     897

<210> SEQ ID NO 37
<211> LENGTH: 5922
<212> TYPE: DNA

<213> ORGANISM: artificial sequence
<220> FEATURE:
<223> OTHER INFORMATION: pCLS19744 (TALEN PPT)

<400> SEQUENCE: 37

```
gggtacgttt aaacgtatta attaagacct agcatgtgag caaaaggcca gcaaaaggcc      60
aggaaccgta aaaaggccgc gttgctggcg ttttttccata ggctccgccc ccctgacgag     120
catcacaaaa atcgacgctc aagtcagagg tggcgaaacc cgacaggact ataaagatac     180
caggcgtttc cccctggaag ctccctcgtg cgctctcctg ttccgaccct gccgcttacc     240
ggatacctgt ccgcctttct cccttcggga agcgtggcgc tttctcatag ctcacgctgt     300
aggtatctca gttcggtgta ggtcgttcgc tccaagctgg gctgtgtgca cgaaccccccc    360
gttcagcccg accgctgcgc cttatccggt aactatcgtc ttgagtccaa cccggtaaga    420
cacgacttat cgccactggc agcagccact ggtaacagga ttagcagagc gaggtatgta    480
ggcggtgcta cagagttctt gaagtggtgg cctaactacg gctacactag aaggacagta    540
tttggtatct gcgctctgct gaagccagtt accttcggaa aaagagttgg tagctcttga    600
tccggcaaac aaaccaccgc tggtagcggt ggtttttttg tttgcaagca gcagattacg    660
cgcagaaaaa aaggatctca agaagatcct ttgatctttt ctacggggtc tgacgctcag    720
tggaacgaaa actcacgtta agggattttg gtcatgagat tatcaaaaag gatcttcacc    780
tagatccttt taaattaaaa atgaagtttt aaatcaatct aaagtatata tgagtaaact    840
tggtctgaca gttaccaatg cttaatcagt gaggcaccta tctcagcgat ctgtctattt    900
cgttcatcca tagttgcctg actccccgtc gtgtagataa ctacgatacg ggagggctta    960
ccatctggcc ccagtgctgc aatgataccg cgagacccac gctcaccggc tccagattta   1020
tcagcaataa accagccagc cggaagggcc gagcgcagaa gtggtcctgc aactttatcc   1080
gcctccatcc agtctattaa ttgttgccgg gaagctagag taagtagttc gccagttaat   1140
agtttgcgca acgttgttgc cattgctaca ggcatcgtgg tgtcacgctc gtcgtttggt   1200
atggcttcat tcagctccgg ttcccaacga tcaaggcgag ttacatgatc ccccatgttg   1260
tgcaaaaaag cggttagctc cttcggtcct ccgatcgttg tcagaagtaa gttggccgca   1320
gtgttatcac tcatggttat ggcagcactg cataattctc ttactgtcat gccatccgta   1380
agatgctttt ctgtgactgg tgagtactca accaagtcat tctgagaata gtgtatgcgg   1440
cgaccgagtt gctcttgccc ggcgtcaata cgggataata ccgcgccaca tagcagaact   1500
ttaaaagtgc tcatcattgg aaaacgttct cggggcgaaa actctcaagg atcttaccg   1560
ctgttgagat ccagttcgat gtaacccact cgtgcaccca actgatcttc agcatctttt   1620
actttcacca gcgtttctgg gtgagcaaaa acaggaaggc aaaatgccgc aaaaaaggga   1680
ataagggcga cacggaaatg ttgaatactc atactcttcc ttttcaata ttattgaagc   1740
atttatcagg gttattgtct catgagcgga tacatatttg aatgtattta gaaaaataaa   1800
caaatagggg ttccgcgcac atttccccga aaagtgccac ctgacaaact tggtaccata   1860
actagttcgg cgcgccaatc tcgcctattc atggtgtata aagttcaac atccaaagct   1920
agaacttttg gaaagagaaa gaatgtccga atagggcacg gcgtgccgta ttgttggagt   1980
ggactagcag aaagtgagga aggcacagga tgagtttcct cgagacacat agcttcagcg   2040
tcgtgtaggc taggcagagg tgagttttct cgagacatac cttcagcgtc gtcttcactg   2100
tcacagtcaa ctgacagtaa tcgttgatcc ggagagattc aaaattcaat ctgtttggac   2160
ctggataaga cacaagagcg acatcctgac atgaacgccg taaacagcaa atcctggttg   2220
```

```
aacacgtatc cttttggggg cctccagcta cgacgctcgc cccagctggg gcttccttac    2280
tatacacagc gcatatttca cggttgccag aaccatgggc gatcctaaaa agaaacgtaa    2340
ggtcatcgat tacccatacg atgttccaga ttacgctatc gatatcgccg accccattcg    2400
ttcgcgcaca ccaagtcctg cccgcgagct tctgcccgga ccccaacccg atggggttca    2460
gccgactgca gatcgtgggg tgtctccgcc tgccggcggc cccctggatg gcttgccggc    2520
tcggcggacg atgtcccgga cccggctgcc atctcccccct gcccctcac ctgcgttctc    2580 ggcgggcagc ttcagtgacc tgttacgtca gttcgatccg tcacttttta atacatcgct    2640
ttttgattca ttgcctccct tcggcgctca ccatacagag gctgccacag gcgagtggga    2700
tgaggtgcaa tcgggtctgc gggcagccga cgccccccca cccaccatgc gcgtggctgt    2760
cactgccgcg cggcccccgc gcgccaagcc ggcgccgcga cgacgtgctg cgcaaccctc    2820
cgacgcttcg ccggcggcgc aggtggatct acgcacgctc ggctacagcc agcagcaaca    2880
ggagaagatc aaaccgaagg ttcgttcgac agtggcgcag caccacgagg cactggtcgg    2940
ccacggggtt acacacgcgc acatcgttgc gttaagccaa cacccggcag cgttagggac    3000
cgtcgctgtc aagtatcagg acatgatcgc agcgttgcca gaggcgacac acgaagcgat    3060
cgttggcgtc ggcaaacagt ggtccggcgc acgcgctctg gaggccttgc tcacggtggc    3120
gggagagttg agaggtccac cgttacagtt ggacacaggc caacttctca agattgcaaa    3180
acgtggcggc gtgaccgcag tggaggcagt gcatgcatgg cgcaatgcac tgacgggtgc    3240
cccgctcaac ttgacccccc agcaggtggt ggccatcgcc agcaataatg gtggcaagca    3300
ggcgctggag acggtccagc ggctgttgcc ggtgctgtgc caggcccacg gcttgacccc    3360
ccagcaggtg gtggccatcg ccagcaataa tggtggcaag caggcgctgg agacggtcca    3420
gcggctgttg ccggtgctgt gccaggccca cggcttgacc cccagcagg tggtggccat    3480 cgccagcaat ggcggtggca agcaggcgct ggagacggtc cagcggctgt tgccggtgct    3540
gtgccaggcc cacggcttga ccccggagca ggtggtggcc atcgccagcc acgatggcgg    3600
caagcaggcg ctggagacgg tccagcggct gttgccggtg ctgtgccagg cccacggctt    3660
gaccccccag caggtggtgg ccatcgccag caatggcggt ggcaagcagg cgctggagac    3720
ggtccagcgg ctgttgccgg tgctgtgcca ggcccacggc ttgaccccc agcaggtggt    3780 ggccatcgcc agcaatggcg gtggcaagca ggcgctggag acggtccagc ggctgttgcc    3840
ggtgctgtgc caggcccacg gcttgacccc ccagcaggtg gtggccatcg ccagcaatgg    3900
cggtggcaag caggcgctgg agacggtcca gcggctgttg ccggtgctgt gccaggccca    3960
cggcttgacc cccagcagg tggtggccat cgccagcaat aatggtggca agcaggcgct    4020
ggagacggtc cagcggctgt tgccggtgct gtgccaggcc cacggcttga ccccggagca    4080
ggtggtggcc atcgccagcc acgatggcgg caagcaggcg ctggagacgg tccagcggct    4140
gttgccggtg ctgtgccagg cccacggctt gaccccggag caggtggtgg ccatcgccag    4200
ccacgatggc ggcaagcagg cgctggagac ggtccagcgg ctgttgccgg tgctgtgcca    4260
ggcccacggc ttgaccccgg agcaggtggt ggccatcgcc agccacgatg gcggcaagca    4320
ggcgctggag acggtccagc ggctgttgcc ggtgctgtgc caggcccacg gcttgacccc    4380
ggagcaggtg gtggccatcg ccagcaatat tggtggcaag caggcgctgg agacggtgca    4440
ggcgctgttg ccggtgctgt gccaggccca cggcttgacc cccagcagg tggtggccat    4500 cgccagcaat ggcggtggca agcaggcgct ggagacggtc cagcggctgt tgccggtgct    4560
```

```
gtgccaggcc cacggcttga cccccagca ggtggtggcc atcgccagca ataatggtgg   4620
caagcaggcg ctggagacgg tccagcggct gttgccggtg ctgtgccagg cccacggctt   4680
gaccccccag caggtggtgg ccatcgccag caataatggt ggcaagcagg cgctggagac   4740
ggtccagcgc ctgttgccgg tgctgtgcca ggcccacggc ttgacccctc agcaggtggt   4800
ggccatcgcc agcaatggcg gcggcaggcc ggcgctggag agcattgttg cccagttatc   4860
tcgccctgat ccggcgttgg ccgcgttgac caacgaccac ctcgtcgcct tggcctgcct   4920
cggcgggcgt cctgcgctgg atgcagtgaa aaagggattg ggggatccta tcagccgttc   4980
ccagctggtg aagtccgagc tggaggagaa gaaatccgag ttgaggcaca gctgaagta    5040 cgtgccccac gagtacatcg agctgatcga gatcgcccgg aacagcaccc aggaccgtat   5100
cctggagatg aaggtgatgg agttcttcat gaaggtgtac ggctacaggg gcaagcacct   5160
gggcggctcc aggaagcccg acggcgccat ctacaccgtg gctcccca tcgactacgg    5220 cgtgatcgtg gacaccaagg cctactccgg cggctacaac ctgcccatcg gccaggccga   5280
cgaaatgcag aggtacgtgg aggagaacca gaccaggaac aagcacatca ccccaacga    5340 gtggtggaag gtgtaccccc tcagcgtgac cgagttcaag ttcctgttcg tgtccggcca   5400
cttcaagggc aactacaagg cccagctgac caggctgaac cacatcacca actgcaacgg   5460
cgccgtgctg tccgtggagg agctcctgat cggcggcgag atgatcaagg ccggcacccct   5520 gaccctggag gaggtgagga ggaagttcaa caacggcgag atcaacttcg cggccgactg   5580
ataactcgag cgatcctcta gacgagctcc tcgagcctgc agcagctgaa gctttaagat   5640
ccaatggcaa ggaccaagtg ctggaacttg ttttgcttta gcagatctag atcgagctac   5700
ctcgactttg gctgggacac tttcagtgag gacaagaagc ttcagaagcg tgctatcgaa   5760
ctcaaccagg gacgtgcggc acaaatgggc atccttgctc tcatggtgca cgaacagttg   5820
ggagtctcta tccttcctta aaaatttaat tttcattagt tgcagtcact ccgctttggt   5880
ttcacagtca ggaataacac tagctcgtct tcatatcctg ca                      5922

<210> SEQ ID NO 38
<211> LENGTH: 5940
<212> TYPE: DNA
<213> ORGANISM: artificial sequence
<220> FEATURE:
<223> OTHER INFORMATION: pCLS19748 (TALEN PPT)

<400> SEQUENCE: 38
gggtacgttt aaacgtatta attaagacct agcatgtgag caaaaggcca gcaaaaggcc     60
aggaaccgta aaaaggccgc gttgctggcg ttttttccata ggctccgccc ccctgacgag   120
catcacaaaa atcgacgctc aagtcagagg tggcgaaacc cgacaggact ataaagatac   180
caggcgtttc ccctggaag ctccctcgtg cgctctcctg ttccgaccct gccgcttacc    240
ggatacctgt ccgcctttct cccttcggga agcgtggcgc tttctcatag ctcacgctgt   300
aggtatctca gttcggtgta ggtcgttcgc tccaagctgg gctgtgtgca cgaaccccc     360 gttcagcccg accgctgcgc cttatccggt aactatcgtc ttgagtccaa cccggtaaga   420
cacgacttat cgccactggc agcagccact ggtaacagga ttagcagagc gaggtatgta    480
ggcggtgcta cagagttctt gaagtggtgg cctaactacg gctacactag aaggacagta   540
tttggtatct gcgctctgct gaagccagtt accttcggaa aaagagttgg tagctcttga   600
tccggcaaac aaaccaccgc tggtagcggt ggtttttttg tttgcaagca gcagattacg   660
cgcagaaaaa aaggatctca agaagatcct ttgatctttt ctacggggtc tgacgctcag   720
```

-continued

```
tggaacgaaa actcacgtta agggattttg gtcatgagat tatcaaaaag gatcttcacc      780
tagatccttt taaattaaaa atgaagtttt aaatcaatct aaagtatata tgagtaaact      840
tggtctgaca gttaccaatg cttaatcagt gaggcaccta tctcagcgat ctgtctattt      900
cgttcatcca tagttgcctg actccccgtc gtgtagataa ctacgatacg ggagggctta      960
ccatctggcc ccagtgctgc aatgataccg cgagacccac gctcaccggc tccagattta     1020
tcagcaataa accagccagc cggaagggcc gagcgcagaa gtggtcctgc aactttatcc     1080
gcctccatcc agtctattaa ttgttgccgg gaagctagag taagtagttc gccagttaat     1140
agtttgcgca acgttgttgc cattgctaca ggcatcgtgg tgtcacgctc gtcgtttggt     1200
atggcttcat tcagctccgg ttcccaacga tcaaggcgag ttacatgatc ccccatgttg     1260
tgcaaaaaag cggttagctc cttcggtcct ccgatcgttg tcagaagtaa gttggccgca     1320
gtgttatcac tcatggttat ggcagcactg cataattctc ttactgtcat gccatccgta     1380
agatgctttt ctgtgactgg tgagtactca accaagtcat tctgagaata gtgtatgcgg     1440
cgaccgagtt gctcttgccc ggcgtcaata cgggataata ccgcgccaca tagcagaact     1500
ttaaaagtgc tcatcattgg aaaacgttct cggggcgaaa actctcaagg atcttaccg     1560 ctgttgagat ccagttcgat gtaacccact cgtgcaccca actgatcttc agcatctttt     1620
actttcacca gcgtttctgg gtgagcaaaa acaggaaggc aaaatgccgc aaaaaaggga     1680
ataagggcga cacggaaatg ttgaatactc atactcttcc ttttttcaata ttattgaagc     1740 atttatcagg gttattgtct catgagcgga tacatatttg aatgtattta gaaaaataaa     1800
caaatagggg ttccgcgcac atttccccga aaagtgccac ctgacaaact tggtaccata     1860
actagttcgg cgcgccaatc tcgcctattc atggtgtata aaagttcaac atccaaagct     1920
agaacttttg gaaagagaaa gaatgtccga ataggggcacg gcgtgccgta ttgttggagt     1980
ggactagcag aaagtgagga aggcacagga tgagtttcct cgagacacat agcttcagcg     2040
tcgtgtaggc taggcagagg tgagttttct cgagacatac cttcagcgtc gtcttcactg     2100
tcacagtcaa ctgacagtaa tcgttgatcc ggagagattc aaaattcaat ctgtttggac     2160
ctggataaga cacaagagcg acatcctgac atgaacgccg taaacagcaa atcctggttg     2220
aacacgtatc cttttggggg cctccagcta cgacgctcgc cccagctggg gcttccttac     2280
tatacacagc gcatatttca cggttgccag aaccatgggc gatcctaaaa agaaacgtaa     2340
ggtcatcgat aaggagaccg ccgctgccaa gttcgagaga cagcacatgg acagcatcga     2400
tatcgccgac cccattcgtt cgcgcacacc aagtcctgcc cgcgagcttc tgcccggacc     2460
ccaacccgat ggggttcagc cgactgcaga tcgtggggtg tctccgcctg ccggcggccc     2520
cctggatggc ttgccggctc ggcggacgat gtccggacc cggctgccat ctcccctgc      2580 cccctcacct gcgttctcgg cgggcagctt cagtgacctg ttacgtcagt tcgatccgtc     2640 acttttaat acatcgcttt ttgattcatt gcctcccttc ggcgctcacc atacagaggc      2700
tgccacaggc gagtgggatg aggtgcaatc gggtctgcgg gcagccgacg cccccccacc     2760
caccatgcgc gtggctgtca ctgccgcgcg gccccccgcgc gccaagccgg cgccgcgacg     2820
acgtgctgcg caaccctccg acgcttcgcc ggcggcgcag gtggatctac gcacgctcgg     2880
ctacagccag cagcaacagg agaagatcaa accgaaggtt cgttcgacag tggcgcagca     2940
ccacgaggca ctggtcggcc acgggtttac acacgcgcac atcgttgcgt taagccaaca     3000
cccggcagcg ttagggaccg tcgctgtcaa gtatcaggac atgatcgcag cgttgccaga     3060
```

-continued

```
ggcgacacac gaagcgatcg ttggcgtcgg caaacagtgg tccggcgcac gcgctctgga    3120
ggccttgctc acggtggcgg gagagttgag aggtccaccg ttacagttgg acacaggcca    3180
acttctcaag attgcaaaac gtggcggcgt gaccgcagtg gaggcagtgc atgcatggcg    3240
caatgcactg acgggtgccc cgctcaactt gacccccag caggtggtgg ccatcgccag    3300
caataatggt ggcaagcagg cgctggagac ggtccagcgg ctgttgccgg tgctgtgcca    3360
ggcccacggc ttgaccccgg agcaggtggt ggccatcgcc agccacgatg gcggcaagca    3420
ggcgctggag acggtccagc ggctgttgcc ggtgctgtgc caggcccacg gcttgacccc    3480
ggagcaggtg gtggccatcg ccagcaatat tggtggcaag caggcgctgg agacggtgca    3540
ggcgctgttg ccggtgctgt gccaggccca cggcttgacc cccagcagg tggtggccat    3600 cgccagcaat ggcggtggca agcaggcgct ggagacggtc cagcggctgt tgccggtgct    3660
gtgccaggcc cacggcttga cccccagca ggtggtggcc atcgccagca ataatggtgg    3720
caagcaggcg ctggagacgg tccagcggct gttgccggtg ctgtgccagg cccacggctt    3780
gaccccggag caggtggtgg ccatcgccag ccacgatggc ggcaagcagg cgctggagac    3840
ggtccagcgg ctgttgccgg tgctgtgcca ggcccacggc ttgaccccgg agcaggtggt    3900
ggccatcgcc agccacgatg gcggcaagca ggcgctggag acggtccagc ggctgttgcc    3960
ggtgctgtgc caggcccacg gcttgacccc ggagcaggtg gtggccatcg ccagcaatat    4020
tggtggcaag caggcgctgg agacggtgca ggcgctgttg ccggtgctgt gccaggccca    4080
cggcttgacc cccagcagg tggtggccat cgccagcaat aatggtggca agcaggcgct    4140
ggagacggtc cagcggctgt tgccggtgct gtgccaggcc cacggcttga cccccggagca    4200 ggtggtggcc atcgccagca atattggtgg caagcaggcg ctggagacgg tgcaggcgct    4260
gttgccggtg ctgtgccagg cccacggctt gaccccggag caggtggtgg ccatcgccag    4320
caatattggt ggcaagcagg cgctggagac ggtgcaggcg ctgttgccgg tgctgtgcca    4380
ggcccacggc ttgaccccc agcaggtggt ggccatcgcc agcaatggcg gtggcaagca    4440
ggcgctggag acggtccagc ggctgttgcc ggtgctgtgc caggcccacg gcttgacccc    4500
ccagcaggtg tgccatcg ccagcaatgg cggtggcaag caggcgctgg agacggtcca    4560
gcggctgttg ccggtgctgt gccaggccca cggcttgacc ccggagcagg tggtggccat    4620
cgccagcaat attggtggca agcaggcgct ggagacggtg caggcgctgt tgccggtgct    4680
gtgccaggcc cacggcttga ccccggagca ggtggtggcc atcgccagca atattggtgg    4740
caagcaggcg ctggagacgg tgcaggcgct gttgccggtg ctgtgccagg cccacggctt    4800 gaccccctcag caggtggtgg ccatcgccag caatggcggc ggcaggccgg cgctggagag    4860
cattgttgcc cagttatctc gccctgatcc ggcgttggcc gcgttgacca acgaccacct    4920
cgtcgccttg gcctgcctcg gcgggcgtcc tgcgctggat gcagtgaaaa agggattggg    4980
ggatcctatc agccgttccc agctggtgaa gtccgagctg gaggagaaga atccgagtt    5040 gaggcacaag ctgaagtacg tgccccacga gtacatcgag ctgatcgaga tcgcccggaa    5100
cagcacccag gaccgtatcc tggagatgaa ggtgatggag ttcttcatga aggtgtacgg    5160 ctacagggc aagcacctgg gcggctccag gaagcccgac ggcgccatct acaccgtggg    5220
ctcccccatc gactacggcg tgatcgtgga caccaaggcc tactccggcg gctacaacct    5280
gcccatcggc caggccgacg aaaatgcgag agtacgtgga gagaaccaga ccaggaacaa    5340
gcacatcaac cccaacgagt ggtggaaggt gtacccctcc agcgtgaccg agttcaagtt    5400
cctgttcgtg tccggccact tcaagggcaa ctacaaggcc cagctgacca ggctgaacca    5460
```

```
catcaccaac tgcaacggcg ccgtgctgtc cgtggaggag ctcctgatcg gcggcgagat    5520
gatcaaggcc ggcaccctga ccctggagga ggtgaggagg aagttcaaca acggcgagat    5580
caacttcgcg gccgactgat aactcgagcg atcctctaga cgagctcctc gagcctgcag    5640
cagctgaagc tttaagatcc aatggcaagg accaagtgct ggaacttgtt ttgctttagc    5700
agatctagat cgagctacct cgactttggc tgggacactt tcagtgagga caagaagctt    5760
cagaagcgtg ctatcgaact caaccaggga cgtgcggcac aaatgggcat ccttgctctc    5820
atggtgcacg aacagttggg agtctctatc cttccttaaa aatttaattt tcattagttg    5880
cagtcactcc gctttggttt cacagtcagg aataacacta gctcgtcttc atatcctgca    5940
```

<210> SEQ ID NO 39
<211> LENGTH: 50
<212> TYPE: DNA
<213> ORGANISM: artificial sequence
<220> FEATURE:
<223> OTHER INFORMATION: PPT target

<400> SEQUENCE: 39

```
tggtctttgc ccatgggatg ggagattcgt gctttaattc tggcatgcaa                50
```

<210> SEQ ID NO 40
<211> LENGTH: 62
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (31)..(32)
<223> OTHER INFORMATION: Deep seq PPT_For ; n is a or c or t or g
<220> FEATURE:
<221> NAME/KEY: misc_feature
<222> LOCATION: (33)..(40)
<223> OTHER INFORMATION: n is a, c, g, or t

<400> SEQUENCE: 40

```
ccatctcatc cctgcgtgtc tccgactcag nnnnnnnnnn gaagaacagt cgcacctggt    60
gc                                                                    62
```

<210> SEQ ID NO 41
<211> LENGTH: 50
<212> TYPE: DNA
<213> ORGANISM: artificial sequence
<220> FEATURE:
<223> OTHER INFORMATION: Deep seq PPT_Rev

<400> SEQUENCE: 41

```
cctatcccct gtgtgccttg gcagtctcag tccgccctaa caccttccgc                50
```

<210> SEQ ID NO 42
<211> LENGTH: 933
<212> TYPE: DNA
<213> ORGANISM: Phaeodactylum tricornutum

<400> SEQUENCE: 42

```
atggcagcgc aggtcgacct caaaggcaag gtagcctttg tggctggtgt tgccgattcc    60
actggttacg gctgggcgat cgccaaagct ttggccgaag caggagccac aatcattgtc    120
ggaacgtggc ctccggtact caagatcttc caaatgggtt tgaaaaaggg acagttcaac    180
gaggactcca cactcgcgga tggttcccta atgacgatcg aaaaggtgta tcccctcgat    240
```

```
gccgtctttg atgccccaga cgacgtcccg gatgagatta aggaaaataa gcgttacgct      300
ggattggacg gatacaccat ttccgaagta gccaaagccg tcgaagccga ttacggaaaa      360
atcgatatcc tcgttcattc cctcgccaac ggtcccgaag tcaccaagcc cctcctcgaa      420
acgactcgca aaggatacct cgctgcttct tccgcctccg catactcggc agtctcgctc      480
ctgcaaaaat tcggccccat catgaacgaa ggcggcgcca tgctttcgtt gacgtacatt      540
gcctccgaaa aggtcattcc cggttacggc ggtggcatgt cctccgccaa ggctcagctg      600
gaaagcgaca cccgcaccct cgcctacgaa gccggtcgca agtggggtat tcgcgtcaac      660
accatttccg ccggtcctct caaatcccgg gcggcctccg caattggcaa agagcccggt      720
cagaaaacct ttatcgaata cgccattgat tattccaagg ccaacgcgcc gctcgaacag      780
gatttgtaca gcgacgatgt cggtaacgcc agtctcttt tgaccagccc catggcccga      840
accgttaccg gtgttaccct gtacgtggac aatggcctgc attctatggg tatggccttg      900
gatagcaaag cgatggaagg ctcgcgcgag taa                                  933
```

<210> SEQ ID NO 43
<211> LENGTH: 5922
<212> TYPE: DNA
<213> ORGANISM: artificial sequence
<220> FEATURE:
<223> OTHER INFORMATION: pCLS23157 (TALEN Enoyl_ACP_reductase)

<400> SEQUENCE: 43

```
gggtacgttt aaacgtatta attaagacct agcatgtgag caaaaggcca gcaaaggcc       60 aggaaccgta aaaaggccgc gttgctggcg ttttttccata ggctccgccc ccctgacgag     120
catcacaaaa atcgacgctc aagtcagagg tggcgaaacc cgacaggact ataaagatac     180
caggcgtttc cccctggaag ctccctcgtg cgctctcctg ttccgaccct gccgcttacc     240
ggatacctgt ccgcctttct cccttcggga agcgtggcgc tttctcatag ctcacgctgt     300
aggtatctca gttcggtgta ggtcgttcgc tccaagctgg gctgtgtgca cgaaccccc      360 gttcagcccg accgctgcgc cttatccggt aactatcgtc ttgagtccaa cccggtaaga     420
cacgacttat cgccactggc agcagccact ggtaacagga ttagcagagc gaggtatgta     480
ggcggtgcta cagagttctt gaagtggtgg cctaactacg gctacactag aaggacagta     540
tttggtatct gcgctctgct gaagccagtt accttcggaa aaagagttgg tagctcttga     600
tccggcaaac aaaccaccgc tggtagcggt ggttttttg tttgcaagca gcagattacg     660
cgcagaaaaa aaggatctca agaagatcct ttgatctttt ctacggggtc tgacgctcag     720
tggaacgaaa actcacgtta agggattttg gtcatgagat tatcaaaaag gatcttcacc     780
tagatccttt taaattaaaa atgaagtttt aaatcaatct aaagtatata tgagtaaact     840
tggtctgaca gttaccaatg cttaatcagt gaggcaccta tctcagcgat ctgtctattt     900
cgttcatcca tagttgcctg actccccgtc gtgtagataa ctacgatacg ggagggctta     960
ccatctggcc ccagtgctgc aatgataccg cgagacccac gctcaccggc tccagattta    1020
tcagcaataa accagccagc cggaagggcc gagcgcagaa gtggtcctgc aactttatcc    1080
gcctccatcc agtctattaa ttgttgccgg gaagctagag taagtagttc gccagttaat    1140
agtttgcgca acgttgttgc cattgctaca ggcatcgtgg tgtcacgctc gtcgtttggt    1200
atggcttcat tcagctccgg ttcccaacga tcaaggcgag ttacatgatc ccccatgttg    1260
tgcaaaaaag cggttagctc cttcggtcct ccgatcgttg tcagaagtaa gttggccgca    1320
gtgttatcac tcatggttat ggcagcactg cataattctc ttactgtcat gccatccgta    1380
```

```
agatgctttt ctgtgactgg tgagtactca accaagtcat tctgagaata gtgtatgcgg    1440
cgaccgagtt gctcttgccc ggcgtcaata cgggataata ccgcgccaca tagcagaact    1500
ttaaaagtgc tcatcattgg aaaacgttct tcggggcgaa aactctcaag gatcttaccg    1560
ctgttgagat ccagttcgat gtaacccact cgtgcaccca actgatcttc agcatctttt    1620
actttcacca gcgtttctgg gtgagcaaaa acaggaaggc aaaatgccgc aaaaaaggga    1680
ataagggcga cacggaaatg ttgaatactc atactcttcc tttttcaata ttattgaagc    1740
atttatcagg gttattgtct catgagcgga tacatatttg aatgtattta gaaaaataaa    1800
caaatagggg ttccgcgcac atttccccga aaagtgccac ctgacaaact tggtaccata    1860
actagttcgg cgcgccaatc tcgcctattc atggtgtata aaagttcaac atccaaagct    1920
agaacttttg gaaagagaaa gaatgtccga atagggcacg gcgtgccgta ttgttggagt    1980
ggactagcag aaagtgagga aggcacagga tgagtttcct cgagacacat agcttcagcg    2040
tcgtgtaggc taggcagagg tgagttttct cgagacatac cttcagcgtc gtcttcactg    2100
tcacagtcaa ctgacagtaa tcgttgatcc ggagagattc aaaattcaat ctgtttggac    2160
ctggataaga cacaagagcg acatcctgac atgaacgccg taaacagcaa atcctggttg    2220
aacacgtatc cttttggggg cctccagcta cgacgctcgc cccagctggg gcttccttac    2280
tatacacagc gcatatttca cggttgccag aaccatgggc gatcctaaaa agaaacgtaa    2340
ggtcatcgat tacccatacg atgttccaga ttacgctatc gatatcgccg accccattcg    2400
ttcgcgcaca ccaagtcctg cccgcgagct tctgcccgga ccccaacccg atggggttca    2460
gccgactgca gatcgtgggg tgtctccgcc tgccggcggc cccctggatg gcttgccggc    2520
tcggcggacg atgtcccgga cccggctgcc atctcccccct gccccctcac ctgcgttctc    2580
ggcgggcagc ttcagtgacc tgttacgtca gttcgatccg tcacttttta atacatcgct    2640
ttttgattca ttgcctccct tcggcgctca ccatacagag gctgccacag gcgagtggga    2700
tgaggtgcaa tcgggtctgc gggcagccga cgccccccca cccaccatgc gcgtggctgt    2760
cactgccgcg cggccccccgc gcgccaagcc ggcgccgcga cgacgtgctg cgcaaccctc    2820
cgacgcttcg ccggcggcgc aggtggatct acgcacgctc ggctacagcc agcagcaaca    2880
ggagaagatc aaaccgaagg ttcgttcgac agtggcgcag caccacgagg cactggtcgg    2940
ccacgggttt acacacgcgc acatcgttgc gttaagccaa caccccggcag cgttagggac    3000 cgtcgctgtc aagtatcagg acatgatcgc agcgttgcca gaggcgacac acgaagcgat    3060
cgttggcgtc ggcaaacagt ggtccggcgc acgcgctctg gaggccttgc tcacggtggc    3120
gggagagttg agaggtccac cgttacagtt ggacacaggc caacttctca agattgcaaa    3180
acgtggcggc gtgaccgcag tggaggcagt gcatgcatgg cgcaatgcac tgacgggtgc    3240
cccgctcaac ttgacccccc agcaggtggt ggccatcgcc agcaatggcg gtggcaagca    3300
ggcgctggag acggtccagc ggctgttgcc ggtgctgtgc caggcccacg gcttgacccc    3360
ggagcaggtg gtggccatcg ccagccacga tggcggcaag caggcgctgg agacggtcca    3420
gcggctgttg ccggtgctgt gccaggccca cggcttgacc ccggagcagg tggtggccat    3480
cgccagccac gatggcggca agcaggcgct ggagacggtc agcggctgt tgccggtgct    3540 gtgccaggcc cacggcttga ccccggagca ggtggtggcc atcgccagca atattggtgg    3600
caagcaggcg ctgagacgg tgcaggcgct gttgccggtg ctgtgccagg cccacggctt    3660
gaccccggag caggtggtgg ccatcgccag ccacgatggc ggcaagcagg cgctggagac    3720
```

```
ggtccagcgg ctgttgccgg tgctgtgcca ggcccacggc ttgacccccc agcaggtggt    3780
ggccatcgcc agcaatggcg gtggcaagca ggcgctggag acggtccagc ggctgttgcc    3840
ggtgctgtgc caggcccacg gcttgacccc ccagcaggtg gtggccatcg ccagcaataa    3900
tggtggcaag caggcgctgg agacggtcca gcggctgttg ccggtgctgt gccaggccca    3960
cggcttgacc cccagcagg tggtggccat cgccagcaat aatggtggca agcaggcgct    4020
ggagacggtc agcggctgt tgccggtgct gtgccaggcc cacggcttga ccccccagca    4080
ggtggtggcc atcgccagca atggcggtgg caagcaggcg ctggagacgg tccagcggct    4140
gttgccggtg ctgtgccagg cccacggctt gacccccag caggtggtgg ccatcgccag    4200
caatggcggt ggcaagcagg cgctggagac ggtccagcgg ctgttgccgg tgctgtgcca    4260
ggcccacggc ttgaccccgg agcaggtggt ggccatcgcc agcaatattg gtggcaagca    4320
ggcgctggag acggtcagg cgctgttgcc ggtgctgtgc caggcccacg gcttgacccc    4380
ggagcaggtg gtggccatcg ccagccacga tggcggcaag caggcgctgg agacggtcca    4440
gcggctgttg ccggtgctgt gccaggccca cggcttgacc cccagcagg tggtggccat    4500 cgccagcaat aatggtggca agcaggcgct ggagacggtc agcggctgt tgccggtgct    4560 gtgccaggcc acggcttga ccccccagca ggtggtggcc atcgccagca ataatggtgg    4620
caagcaggcg ctggagacgg tccagcggct gttgccggtg ctgtgccagg cccacggctt    4680
gacccccgag caggtggtgg ccatcgccag ccacgatggc ggcaagcagg cgctggagac    4740
ggtccagcgg ctgttgccgg tgctgtgcca ggcccacggc ttgaccccctc agcaggtggt    4800 ggccatcgcc agcaatggcg gcggcaggcc ggcgctggag agcattgttg cccagttatc    4860
tcgccctgat ccggcgttgg ccgcgttgac caacgaccac ctcgtcgcct tggcctgcct    4920
cggcgggcgt cctgcgctgg atgcagtgaa aaagggattg ggggatccta tcagccgttc    4980
ccagctggtg aagtccgagc tggaggagaa gaaatccgag ttgaggcaca agctgaagta    5040
cgtgccccac gagtacatcg agctgatcga gatcgcccgg aacagcaccc aggaccgtat    5100
cctggagatg aaggtgatgg agttcttcat gaaggtgtac ggctacaggg gcaagcacct    5160
gggcggctcc aggaagcccg acggcgccat ctacaccgtg ggctccccca tcgactacgg    5220
cgtgatcgtg gacaccaagg cctactccgg cggctacaac ctgcccatcg ccaggccga    5280 cgaaatgcag aggtacgtgg aggagaacca gaccaggaac aagcacatca cccccaacga    5340
gtggtggaag gtgtacccct ccagcgtgac cgagttcaag ttcctgttcg tgtccggcca    5400
cttcaagggc aactacaagg cccagctgac caggctgaac cacatcacca actgcaacgg    5460
cgccgtgctg tccgtggagg agctcctgat cggcggcgag atgatcaagg ccggcaccct    5520 gacccctggag gaggtgagga ggaagttcaa caacggcgag atcaacttcg cggccgactg    5580
ataactcgag cgatcctcta gacgagctcc tcgagcctgc agcagctgaa gctttaagat    5640
ccaatggcaa ggaccaagtg ctggaacttg ttttgcttta gcagatctag atcgagctac    5700
ctcgactttg gctgggacac tttcagtgag acaagaagc ttcagaagcg tgctatcgaa    5760
ctcaaccagg gacgtgcggc acaaatgggc atccttgctc tcatggtgca cgaacagttg    5820
ggagtctcta tccttcctta aaatttaat tttcattagt tgcagtcact ccgctttggt    5880
ttcacagtca ggaataacac tagctcgtct tcatatcctg ca                      5922
```

<210> SEQ ID NO 44
<211> LENGTH: 5940
<212> TYPE: DNA
<213> ORGANISM: artificial sequence
<220> FEATURE:
<223> OTHER INFORMATION: pCLS23161 (TALEN Enoyl_ACP_reductase)

<400> SEQUENCE: 44

| | |
|---|---|
| gggtacgttt aaacgtatta attaagacct agcatgtgag caaaaggcca gcaaaaggcc | 60 |
| aggaaccgta aaaggccgcg ttgctggcg ttttttccata ggctccgccc ccctgacgag | 120 |
| catcacaaaa atcgacgctc aagtcagagg tggcgaaacc cgacaggact ataaagatac | 180 |
| caggcgtttc ccctggaag ctccctcgtg cgctctcctg ttccgaccct gccgcttacc | 240 |
| ggatacctgt ccgcctttct cccttcggga agcgtggcgc tttctcatag ctcacgctgt | 300 |
| aggtatctca gttcggtgta ggtcgttcgc tccaagctgg gctgtgtgca cgaacccccc | 360 |
| gttcagcccg accgctgcgc cttatccggt aactatcgtc ttgagtccaa cccggtaaga | 420 |
| cacgacttat cgccactggc agcagccact ggtaacagga ttagcagagc gaggtatgta | 480 |
| ggcggtgcta cagagttctt gaagtggtgg cctaactacg gctacactag aaggacagta | 540 |
| tttggtatct gcgctctgct gaagccagtt accttcggaa aaagagttgg tagctcttga | 600 |
| tccggcaaac aaaccaccgc tggtagcggt ggtttttttg tttgcaagca gcagattacg | 660 |
| cgcagaaaaa aaggatctca agaagatcct ttgatctttt ctacggggtc tgacgctcag | 720 |
| tggaacgaaa actcacgtta agggattttg gtcatgagat tatcaaaaag gatcttcacc | 780 |
| tagatccttt taaattaaaa atgaagtttt aaatcaatct aaagtatata tgagtaaact | 840 |
| tggtctgaca gttaccaatg cttaatcagt gaggcaccta tctcagcgat ctgtctattt | 900 |
| cgttcatcca tagttgcctg actccccgtc gtgtagataa ctacgatacg ggagggctta | 960 |
| ccatctggcc ccagtgctgc aatgataccg cgagacccac gctcaccggc tccagattta | 1020 |
| tcagcaataa accagccagc cggaagggcc gagcgcagaa gtggtcctgc aactttatcc | 1080 |
| gcctccatcc agtctattaa ttgttgccgg gaagctagag taagtagttc gccagttaat | 1140 |
| agtttgcgca acgttgttgc cattgctaca ggcatcgtgg tgtcacgctc gtcgtttggt | 1200 |
| atggcttcat tcagctccgg ttcccaacga tcaaggcgag ttacatgatc ccccatgttg | 1260 |
| tgcaaaaaag cggttagctc cttcggtcct ccgatcgttg tcagaagtaa gttggccgca | 1320 |
| gtgttatcac tcatggttat ggcagcactg cataattctc ttactgtcat gccatccgta | 1380 |
| agatgctttt ctgtgactgg tgagtactca accaagtcat tctgagaata gtgtatgcgg | 1440 |
| cgaccgagtt gctcttgccc ggcgtcaata cgggataata ccgcgccaca tagcagaact | 1500 |
| ttaaaagtgc tcatcattgg aaaacgttct tcgggcgaa aactctcaag gatcttaccg | 1560 |
| ctgttgagat ccagttcgat gtaacccact cgtgcaccca actgatcttc agcatctttt | 1620 |
| actttcacca gcgtttctgg gtgagcaaaa acaggaaggc aaaatgccgc aaaaaaggga | 1680 |
| ataagggcga cacggaaatg ttgaatactc atactcttcc ttttcaata ttattgaagc | 1740 |
| atttatcagg gttattgtct catgagcgga tacatatttg aatgtattta gaaaaataaa | 1800 |
| caaataggg ttccgcgcac atttccccga aaagtgccac ctgacaaact tgtaccata | 1860 |
| actagttcgg cgcgccaatc tcgcctattc atggtgtata aagttcaac atccaaagct | 1920 |
| agaactttg gaaagagaaa gaatgtccga ataggggcacg gcgtgccgta ttgttggagt | 1980 |
| ggactagcag aaagtgagga aggcacagga tgagtttcct cgagacacat agcttcagcg | 2040 |
| tcgtgtaggc taggcagagg tgagttttct cgagacatac cttcagcgtc gtcttcactg | 2100 |
| tcacagtcaa ctgacagtaa tcgttgatcc ggagagattc aaaattcaat ctgtttggac | 2160 |
| ctggataaga cacaagagcg acatcctgac atgaacgccg taaacagcaa atcctggttg | 2220 |

| | |
|---|---|
| aacacgtatc cttttggggg cctccagcta cgacgctcgc cccagctggg gcttccttac | 2280 |
| tatacacagc gcatatttca cggttgccag aaccatgggc gatcctaaaa agaaacgtaa | 2340 |
| ggtcatcgat aaggagaccg ccgctgccaa gttcgagaga cagcacatgg acagcatcga | 2400 |
| tatcgccgac cccattcgtt cgcgcacacc aagtcctgcc cgcgagcttc tgcccggacc | 2460 |
| ccaacccgat ggggttcagc cgactgcaga tcgtggggtg tctccgcctg ccggcggccc | 2520 |
| cctggatggc ttgccggctc ggcggacgat gtcccggacc cggctgccat ctccccctgc | 2580 |
| cccctcacct gcgttctcgg cgggcagctt cagtgacctg ttacgtcagt tcgatccgtc | 2640 |
| acttttaat acatcgcttt ttgattcatt gcctcccttc ggcgctcacc atacagaggc | 2700 |
| tgccacaggc gagtgggatg aggtgcaatc gggtctgcgg gcagccgacg ccccccacc | 2760 |
| caccatgcgc gtggctgtca ctgccgcgcg gccccgcgc gccaagccgg cgccgcgacg | 2820 |
| acgtgctgcg caaccctccg acgcttcgcc ggcggcgcag gtggatctac gcacgctcgg | 2880 |
| ctacagccag cagcaacagg agaagatcaa accgaaggtt cgttcgacag tggcgcagca | 2940 |
| ccacgaggca ctggtcggcc acgggtttac acacgcgcac atcgttgcgt taagccaaca | 3000 |
| cccggcagcg ttagggaccg tcgctgtcaa gtatcaggac atgatcgcag cgttgccaga | 3060 |
| ggcgacacac gaagcgatcg ttggcgtcgg caaacagtgg tccggcgcac gcgctctgga | 3120 |
| ggccttgctc acggtggcgg gagagttgag aggtccaccg ttacagttgg acacaggcca | 3180 |
| acttctcaag attgcaaaac gtggcggcgt gaccgcagtg gaggcagtgc atgcatggcg | 3240 |
| caatgcactg acgggtgccc cgctcaactt gaccccggag caggtggtgg ccatcgccag | 3300 |
| ccacgatggc ggcaagcagg cgctggagac ggtccagcgg ctgttgccgg tgctgtgcca | 3360 |
| ggcccacggc ttgaccccgg agcaggtggt ggccatcgcc agccacgatg gcggcaagca | 3420 |
| ggcgctggag acggtccagc ggctgttgcc ggtgctgtgc caggcccacg gcttgacccc | 3480 |
| ccagcaggtg gtggccatcg ccagcaatgg cggtggcaag caggcgctgg agacggtcca | 3540 |
| gcggctgttg ccggtgctgt gccaggccca cggcttgacc cccagcagg tggtggccat | 3600 |
| cgccagcaat aatggtggca agcaggcgct ggagacggtc agcggctgt tgccggtgct | 3660 |
| gtgccaggcc cacggcttga ccccggagca ggtggtggcc atcgccagcc acgatggcgg | 3720 |
| caagcaggcg ctggagacgg tccagcggct gttgccggtg ctgtgccagg cccacggctt | 3780 |
| gaccccccag caggtggtgg ccatcgccag caatggcgt ggcaagcagg cgctggagac | 3840 |
| ggtccagcgg ctgttgccgg tgctgtgcca ggcccacggc ttgacccccc agcaggtggt | 3900 |
| ggccatcgcc agcaatggcg gtggcaagca ggcgctggag acggtccagc ggctgttgcc | 3960 |
| ggtgctgtgc caggcccacg gcttgacccc ggagcaggtg gtggccatcg ccagccacga | 4020 |
| tggcggcaag caggcgctgg agacggtcca gcggctgttg ccggtgctgt gccaggccca | 4080 |
| cggcttgacc cccagcagg tggtggccat cgccagcaat aatggtggca agcaggcgct | 4140 |
| ggagacggtc agcggctgt tgccggtgct gtgccaggcc cacggcttga ccccccagca | 4200 |
| ggtggtggcc atcgccagca ataatggtgg caagcaggcg ctggagacgg tccagcggct | 4260 |
| gttgccggtg ctgtgccagg cccacggctt gaccccggag caggtggtgg ccatcgccag | 4320 |
| ccacgatggc ggcaagcagg cgctggagac ggtccagcgg ctgttgccgg tgctgtgcca | 4380 |
| ggcccacggc ttgaccccgg agcaggtggt ggccatcgcc agccacgatg gcggcaagca | 4440 |
| ggcgctggag acggtccagc ggctgttgcc ggtgctgtgc caggcccacg gcttgacccc | 4500 |
| ggagcaggtg gtggccatcg ccagcaatat tggtggcaag caggcgctgg agacggtgca | 4560 |
| ggcgctgttg ccggtgctgt gccaggccca cggcttgacc ccggagcagg tggtggccat | 4620 |

-continued

```
cgccagcaat attggtggca agcaggcgct ggagacggtg caggcgctgt tgccggtgct    4680
gtgccaggcc cacggcttga ccccggagca ggtggtggcc atcgccagca atattggtgg    4740
caagcaggcg ctggagacgg tgcaggcgct gttgccggtg ctgtgccagg cccacggctt    4800 gaccccctcag caggtggtgg ccatcgccag caatggcggc ggcaggccgg cgctggagag    4860
cattgttgcc cagttatctc gccctgatcc ggcgttggcc gcgttgacca acgaccacct    4920
cgtcgccttg gcctgcctcg gcgggcgtcc tgcgctggat gcagtgaaaa agggattggg    4980
ggatcctatc agccgttccc agctggtgaa gtccgagctg gaggagaaga atccgagtt     5040 gaggcacaag ctgaagtacg tgccccacga gtacatcgag ctgatcgaga tcgcccggaa    5100
cagcacccag gaccgtatcc tggagatgaa ggtgatggag ttcttcatga aggtgtacgg    5160
ctacaggggc aagcacctgg gcggctccag gaagcccgac ggcgccatct acaccgtggg    5220
ctcccccatc gactacggcg tgatcgtgga caccaaggcc tactccggcg gctacaacct    5280
gcccatcggc caggccgacg aaatgcagag gtacgtggag gagaaccaga ccaggaacaa    5340
gcacatcaac cccaacgagt ggtggaaggt gtacccctcc agcgtgaccg agttcaagtt    5400
cctgttcgtg tccggccact tcaagggcaa ctacaaggcc cagctgacca ggctgaacca    5460
catcaccaac tgcaacggcg ccgtgctgtc cgtggaggag ctcctgatcg gcggcgagat    5520
gatcaaggcc ggcaccctga ccctggagga ggtgaggagg aagttcaaca acggcgagat    5580
caacttcgcg gccgactgat aactcgagcg atcctctaga cgagctcctc gagcctgcag    5640
cagctgaagc tttaagatcc aatggcaagg accaagtgct ggaacttgtt ttgctttagc    5700
agatctagat cgagctacct cgactttggc tgggacactt tcagtgagga caagaagctt    5760
cagaagcgtg ctatcgaact caaccaggga cgtgcggcac aaatgggcat ccttgctctc    5820
atggtgcacg aacagttggg agtctctatc cttccttaaa aatttaatttt tcattagttg    5880 cagtcactcc gctttggttt cacagtcagg aataacacta gctcgtcttc atatcctgca    5940
```

<210> SEQ ID NO 45
<211> LENGTH: 58
<212> TYPE: DNA
<213> ORGANISM: artificial sequence
<220> FEATURE:
<223> OTHER INFORMATION: Enoyl_ACP_reductase target

<400> SEQUENCE: 45

```
tgttgccgat tccactggtt acggctgggc gatcgccaaa gctttggccg aagcagga          58
```

<210> SEQ ID NO 46
<211> LENGTH: 63
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (31)..(32)
<223> OTHER INFORMATION: Deep seq Enoyl_ACP_reductase_For ; n is a or c
      or t or g
<220> FEATURE:
<221> NAME/KEY: misc_feature
<222> LOCATION: (33)..(40)
<223> OTHER INFORMATION: n is a, c, g, or t

<400> SEQUENCE: 46

```
ccatctcatc cctgcgtgtc tccgactcag nnnnnnnnnn ggactgtttc gctacggtac    60
atc                                                                   63
```

<210> SEQ ID NO 47
<211> LENGTH: 53
<212> TYPE: DNA
<213> ORGANISM: artificial sequence
<220> FEATURE:
<223> OTHER INFORMATION: Deep seq Enoyl_ACP_reductase_Rev

<400> SEQUENCE: 47
cctatcccct gtgtgccttg gcagtctcag gaaatggtgt atccgtccaa tcc        53

<210> SEQ ID NO 48
<211> LENGTH: 1629
<212> TYPE: DNA
<213> ORGANISM: Phaeodactylum tricornutum

<400> SEQUENCE: 48
ttttttttcc ctcggttcgg acttttttcc ctcgtcggtg gtccgtattg gatcaagtct      60
gtctgtgact tccgttagcg tcccatagtt tgttacactt ggctgtgaaa cgaatacgtt     120
cttggtctac ttactacaac gaagcaacca ccagcagcat gggtaaggga ggtcaacgag     180
ctgtagctcc caagagtgcc accagctcta ctggcagtgc tacccttagc caaagcaagg     240
aacaggtatg gacttcgtcg tacaaccctc tggcgaagga tgccccggag ctgccaacca     300
aaggccaaat caaggccgtc attccgaagg aatgtttcca acgctcagcc ttttggtcta     360
ccttctacct gatgcgcgat ctcgccatgg ctgccgcctt tgctacgga acctcacagg     420
tcctctccac cgaccttccc caagacgcca cgctcattct gccctgggct ctcggctggg     480
gcgtctacgc cttttggatg ggaaccattc tcaccgggcc ttgggtagtt gcgcacgaat     540
gtggacacgg cgcttactcc gactcccaga cgttcaatga cgttgtcggc tttatcgtcc     600
accaagcttt gctcgtcccc tactttgcct ggcagtacac ccacgcgaaa caccaccgtc     660
gtaccaacca tctggtggac ggcgagtcgc acgtcccttc taccgccaag gataacggcc     720
tcgggccgca caacgagcga aactccttct acgccgcgtg gcacgaggcc atgggagacg     780
gcgcctttgc cgtctttcaa gtctggtcgc acttgttcgt cggctggcct ctctacttgg     840
ccggtctggc cagtaccgga aagcttgcgc acgaaggttg gtggctggaa gaacggaacg     900
cgattgcgga tcactttcga cccagctctc ccatgttccc cgccaagatc cgtgccaaga     960
ttgcccttc cagcgcgacg gaactcgccg tgctcgctgg actcttgtat gtcggtacac    1020
aggtcggaca ccttcccgtc ctgctgtggt actggggacc gtacaccttt gtcaacgctt    1080
ggcttgtact ctacacgtgg ctgcagcata cggacccgtc catcccgcac tacggtgaag    1140
gcgagtggac ctgggtcaag ggcgcgctct ctaccattga tcgagactac ggcatcttcg    1200
atttctttca ccacaccatc ggttccacgc acgtggtaca ccattgttc cacgaaatgc    1260
cctggtacaa tgccggcatt gccacgcaaa aggtcaagga attttggaa ccccagggct    1320
tgtacaatta cgatccgacc ccctggtaca aggccatgtg cgcgcattgcc cggacctgtc    1380
actatgtgga gtcaaacgag ggtgtgcagt atttcaagag tatggaaaac gtgccgctga    1440
ctaaggatgt gcgaagcaaa gccgcatgag aaaaagtgcc accgacgcat aattttacaa    1500
tcctaccaac aagaccaaca ttatatggtt ttcgcttaaa agatagtttt ttctaccatc    1560
tgtgtagtcg gcacaactac gcgtcttagc ttggccgtca ccttgccggc tcgcgaggcc    1620
aaagttcgg                                                          1629

<210> SEQ ID NO 49

<211> LENGTH: 5922
<212> TYPE: DNA
<213> ORGANISM: artificial sequence
<220> FEATURE:
<223> OTHER INFORMATION: pCLS19743 (TALEN Delta12 desaturase FAD2)

<400> SEQUENCE: 49

| | | | | | |
|---|---|---|---|---|---|
| gggtacgttt | aaacgtatta | attaagacct | agcatgtgag | caaaaggcca | gcaaaaggcc | 60 |
| aggaaccgta | aaaaggccgc | gttgctggcg | ttttttccata | ggctccgccc | ccctgacgag | 120 |
| catcacaaaa | atcgacgctc | aagtcagagg | tggcgaaacc | cgacaggact | ataaagatac | 180 |
| caggcgtttc | cccctggaag | ctccctcgtg | cgctctcctg | ttccgaccct | gccgcttacc | 240 |
| ggatacctgt | ccgcctttct | cccttcggga | agcgtggcgc | tttctcatag | ctcacgctgt | 300 |
| aggtatctca | gttcggtgta | ggtcgttcgc | tccaagctgg | gctgtgtgca | cgaaccccc | 360 |
| gttcagcccg | accgctgcgc | cttatccggt | aactatcgtc | ttgagtccaa | cccggtaaga | 420 |
| cacgacttat | cgccactggc | agcagccact | ggtaacagga | ttagcagagc | gaggtatgta | 480 |
| ggcggtgcta | cagagttctt | gaagtggtgg | cctaactacg | gctacactag | aaggacagta | 540 |
| tttggtatct | gcgctctgct | gaagccagtt | accttcggaa | aaagagttgg | tagctcttga | 600 |
| tccggcaaac | aaaccaccgc | tggtagcggt | ggttttttttg | tttgcaagca | gcagattacg | 660 |
| cgcagaaaaa | aaggatctca | agaagatcct | ttgatctttt | ctacggggtc | tgacgctcag | 720 |
| tggaacgaaa | actcacgtta | agggattttg | gtcatgagat | tatcaaaaag | gatcttcacc | 780 |
| tagatccttt | taaattaaaa | atgaagtttt | aaatcaatct | aaagtatata | tgagtaaact | 840 |
| tggtctgaca | gttaccaatg | cttaatcagt | gaggcaccta | tctcagcgat | ctgtctattt | 900 |
| cgttcatcca | tagttgcctg | actccccgtc | gtgtagataa | ctacgatacg | ggagggctta | 960 |
| ccatctggcc | ccagtgctgc | aatgataccg | cgagacccac | gctcaccggc | tccagattta | 1020 |
| tcagcaataa | accagccagc | cggaagggcc | gagcgcagaa | gtggtcctgc | aactttatcc | 1080 |
| gcctccatcc | agtctattaa | ttgttgccgg | gaagctagag | taagtagttc | gccagttaat | 1140 |
| agtttgcgca | acgttgttgc | cattgctaca | ggcatcgtgg | tgtcacgctc | gtcgtttggt | 1200 |
| atggcttcat | tcagctccgg | ttcccaacga | tcaaggcgag | ttacatgatc | ccccatgttg | 1260 |
| tgcaaaaaag | cggttagctc | cttcggtcct | ccgatcgttg | tcagaagtaa | gttggccgca | 1320 |
| gtgttatcac | tcatggttat | ggcagcactg | cataattctc | ttactgtcat | gccatccgta | 1380 |
| agatgctttt | ctgtgactgg | tgagtactca | accaagtcat | tctgagaata | gtgtatgcgg | 1440 |
| cgaccgagtt | gctcttgccc | ggcgtcaata | cgggataata | ccgcgccaca | tagcagaact | 1500 |
| ttaaaagtgc | tcatcattgg | aaaacgttct | tcggggcgaa | aactctcaag | gatcttaccg | 1560 |
| ctgttgagat | ccagttcgat | gtaacccact | cgtgcaccca | actgatcttc | agcatctttt | 1620 |
| actttcacca | gcgtttctgg | gtgagcaaaa | acaggaaggc | aaaatgccgc | aaaaaaggga | 1680 |
| ataagggcga | cacggaaatg | ttgaatactc | atactcttcc | ttttttcaata | ttattgaagc | 1740 |
| atttatcagg | gttattgtct | catgagcgga | tacatatttg | aatgtattta | gaaaaataaa | 1800 |
| caaatagggg | ttccgcgcac | atttccccga | aaagtgccac | ctgacaaact | tggtaccata | 1860 |
| actagttcgg | cgcgccaatc | tcgcctattc | atggtgtata | aaagttcaac | atccaaagct | 1920 |
| agaactttttg | gaaagagaaa | gaatgtccga | atagggcacg | gcgtgccgta | ttgttggagt | 1980 |
| ggactagcag | aaagtgagga | aggcacagga | tgagttcct | cgagacacat | agcttcagcg | 2040 |
| tcgtgtaggc | taggcagagg | tgagttttct | cgagacatac | cttcagcgtc | gtcttcactg | 2100 |
| tcacagtcaa | ctgacagtaa | tcgttgatcc | ggagagattc | aaaattcaat | ctgtttggac | 2160 |

```
ctggataaga cacaagagcg acatcctgac atgaacgccg taaacagcaa atcctggttg   2220
aacacgtatc cttttggggg cctccagcta cgacgctcgc cccagctggg gcttccttac   2280
tatacacagc gcatatttca cggttgccag aaccatgggc gatcctaaaa agaaacgtaa   2340
ggtcatcgat tacccatacg atgttccaga ttacgctatc gatatcgccg accccattcg   2400
ttcgcgcaca ccaagtcctg cccgcgagct tctgcccgga ccccaacccg atggggttca   2460
gccgactgca gatcgtgggg tgtctccgcc tgccggcggc cccctggatg gcttgccggc   2520
tcggcggacg atgtcccgga cccggctgcc atctccccct gcccctcac ctgcgttctc   2580 ggcgggcagc ttcagtgacc tgttacgtca gttcgatccg tcactttta atacatcgct   2640 tttttgattca ttgcctccct tcggcgctca ccatacagag gctgccacag gcgagtggga   2700
tgaggtgcaa tcgggtctgc gggcagccga cgccccccca cccaccatgc gcgtggctgt   2760
cactgccgcg cggccccgc gcgccaagcc ggcgccgcga cgacgtgctg cgcaaccctc   2820
cgacgcttcg ccgcggcgc aggtggatct acgcacgctc ggctacagcc agcagcaaca   2880
ggagaagatc aaaccgaagg ttcgttcgac agtggcgcag caccacgagg cactggtcgg   2940
ccacgggttt acacacgcgc acatcgttgc gttaagccaa cacccggcag cgttagggac   3000
cgtcgctgtc aagtatcagg acatgatcgc agcgttgcca gaggcgacac acgaagcgat   3060
cgttggcgtc ggcaaacagt ggtccggcgc acgcgctctg gaggcttgc tcacggtggc   3120 gggagagttg agaggtccac cgttacagtt ggacacaggc caacttctca agattgcaaa   3180
acgtggcggc gtgaccgcag tggaggcagt gcatgcatgg cgcaatgcac tgacgggtgc   3240
cccgctcaac ttgaccccgg agcaggtggt ggccatcgcc agcaatattg gtggcaagca   3300
ggcgctggag acggtgcagg cgctgttgcc ggtgctgtgc caggcccacg gcttgacccc   3360
ccagcaggtg gtggccatcg ccagcaataa tggtggcaag caggcgctgg agacggtcca   3420
gcggctgttg ccggtgctgt gccaggccca cggcttgacc ccggagcagg tggtggccat   3480
cgccagccac gatggcggca agcaggcgct ggagacggtc agcggctgt tgccggtgct   3540 gtgccaggcc cacggcttga ccccccagca ggtggtggcc atcgccagca atggcgtgg   3600 caagcaggcg ctggagacgg tccagcggct gttgccggtg ctgtgccagg ccacggctt   3660 gacccccgag caggtggtgg ccatcgccag ccacgatggc ggcaagcagg cgctggagac   3720
ggtccagcgg ctgttgccgg tgctgtgcca ggcccacggc ttgaccccgg agcaggtggt   3780
ggccatcgcc agccacgatg cggcaagca ggcgctggag acggtccagc ggctgttgcc   3840
ggtgctgtgc caggcccacg gcttgacccc ggagcaggtg gtggccatcg ccagccacga   3900
tggcggcaag caggcgctgg agacggtcca gcggctgttg ccggtgctgt gccaggccca   3960
cggcttgacc ccggagcagg tggtggccat cgccagcaat attggtggca agcaggcgct   4020
ggagacggtg caggcgctgt tgccggtgct gtgccaggcc cacggcttga ccccggagca   4080
ggtggtggcc atcgccagca atattggtgg caagcaggcg ctggagacgg tgcaggcgct   4140
gttgccggtg ctgtgccagg cccacggctt gacccccag caggtggtgg ccatcgccag   4200
caataatggt ggcaagcagg cgctggagac ggtccagcgg ctgttgccgg tgctgtgcca   4260
ggcccacggc ttgaccccgg agcaggtggt ggccatcgcc agcaatattg gtggcaagca   4320
ggcgctggag acggtgcagg cgctgttgcc ggtgctgtgc caggcccacg gcttgacccc   4380
ccagcaggtg gtggccatcg ccagcaataa tggtggcaag caggcgctgg agacggtcca   4440
gcggctgttg ccggtgctgt gccaggccca cggcttgacc ccccagcagg tggtggccat   4500
```

```
cgccagcaat ggcggtggca agcaggcgct ggagacggtc cagcggctgt tgccggtgct    4560
gtgccaggcc cacggcttga ccccccagca ggtggtggcc atcgccagca ataatggtgg    4620
caagcaggcg ctggagacgg tccagcggct gttgccggtg ctgtgccagg cccacggctt    4680
gaccccggag caggtggtgg ccatcgccag ccacgatggc ggcaagcagg cgctggagac    4740
ggtccagcgg ctgttgccgg tgctgtgcca ggcccacggc ttgacccctc agcaggtggt    4800
ggccatcgcc agcaatggcg gcggcaggcc ggcgctggag agcattgttg cccagttatc    4860
tcgccctgat ccggcgttgg ccgcgttgac caacgaccac ctcgtcgcct tggcctgcct    4920
cggcgggcgt cctgcgctgg atgcagtgaa aaagggattg ggggatccta tcagccgttc    4980
ccagctggtg aagtccgagc tggaggagaa gaaatccgag ttgaggcaca agctgaagta    5040
cgtgccccac gagtacatcg agctgatcga gatcgcccgg aacagcaccc aggaccgtat    5100
cctggagatg aaggtgatgg agttcttcat gaaggtgtac ggctacaggg gcaagcacct    5160
gggcggctcc aggaagcccg acggcgccat ctacaccgtg gctcccccca tcgactacgg    5220
cgtgatcgtg gacaccaagg cctactccgg cggctacaac ctgccatcg gccaggccga    5280 cgaaatgcag aggtacgtgg aggagaacca gaccaggaac aagcacatca accccaacga    5340
gtggtggaag gtgtacccct ccagcgtgac cgagttcaag ttcctgttcg tgtccggcca    5400
cttcaagggc aactacaagg cccagctgac caggctgaac cacatcacca actgcaacgg    5460
cgccgtgctg tccgtggagg agctcctgat cggcggcgag atgatcaagg ccggcaccct    5520 gacccctggag gaggtgagga ggaagttcaa caacggcgag atcaacttcg cggccgactg    5580
ataactcgag cgatcctcta gacgagctcc tcgagcctgc agcagctgaa gctttaagat    5640
ccaatggcaa ggaccaagtg ctggaacttg ttttgcttta gcagatctag atcgagctac    5700
ctcgactttg gctgggacac tttcagtgag gacaagaagc ttcagaagcg tgctatcgaa    5760
ctcaaccagg gacgtgcggc acaaatgggc atccttgctc tcatggtgca gaacagttg    5820 ggagtctcta tccttcctta aaaatttaat tttcattagt tgcagtcact ccgctttggt    5880
ttcacagtca ggaataacac tagctcgtct tcatatcctg ca                      5922
```

<210> SEQ ID NO 50
<211> LENGTH: 5940
<212> TYPE: DNA
<213> ORGANISM: artificial sequence
<220> FEATURE:
<223> OTHER INFORMATION: pCLS19747 (TALEN Delta12 desaturase FAD2)

<400> SEQUENCE: 50

```
gggtacgttt aaacgtatta attaagacct agcatgtgag caaaaggcca gcaaaaggcc      60
aggaaccgta aaaaggccgc gttgctggcg ttttttccata ggctccgccc ccctgacgag     120
catcacaaaa atcgacgctc aagtcagagg tggcgaaacc cgacaggact ataaagatac     180
caggcgtttc ccctggaagc tccctcgtg cgctctcctg ttccgaccct gccgcttacc      240
ggatacctgt ccgcctttct cccttcggga agcgtggcgc tttctcatag ctcacgctgt      300
aggtatctca gttcggtgta ggtcgttcgc tccaagctgg gctgtgtgca cgaaccccccc    360 gttcagcccg accgctgcgc cttatccggt aactatcgtc ttgagtccaa cccggtaaga     420
cacgacttat cgccactggc agcagccact ggtaacagga ttagcagagc gaggtatgta      480
ggcggtgcta cagagttctt gaagtggtgg cctaactacg gctacactag aaggacagta     540
tttggtatct gcgctctgct gaagccagtt accttcggaa aaagagttgg tagctcttga    600
tccggcaaac aaaccaccgc tggtagcggt ggtttttttg tttgcaagca gcagattacg      660
```

```
cgcagaaaaa aaggatctca agaagatcct tgatcttttt ctacgggtc tgacgctcag      720 tggaacgaaa actcacgtta agggattttg gtcatgagat tatcaaaaag gatcttcacc    780
tagatccttt taaattaaaa atgaagtttt aaatcaatct aaagtatata tgagtaaact    840
tggtctgaca gttaccaatg cttaatcagt gaggcaccta tctcagcgat ctgtctattt    900
cgttcatcca tagttgcctg actccccgtc gtgtagataa ctacgatacg ggagggctta    960
ccatctggcc ccagtgctgc aatgataccg cgagacccac gctcaccggc tccagattta   1020
tcagcaataa accagccagc cggaagggcc gagcgcagaa gtggtcctgc aactttatcc   1080
gcctccatcc agtctattaa ttgttgccgg gaagctagag taagtagttc gccagttaat   1140
agtttgcgca acgttgttgc cattgctaca ggcatcgtgg tgtcacgctc gtcgtttggt   1200
atggcttcat tcagctccgg ttcccaacga tcaaggcgag ttacatgatc ccccatgttg   1260
tgcaaaaaag cggttagctc cttcggtcct ccgatcgttg tcagaagtaa gttggccgca   1320
gtgttatcac tcatggttat ggcagcactg cataattctc ttactgtcat gccatccgta   1380
agatgctttt ctgtgactgg tgagtactca accaagtcat tctgagaata gtgtatgcgg   1440
cgaccgagtt gctcttgccc ggcgtcaata cgggataata ccgcgccaca tagcagaact   1500
ttaaaagtgc tcatcattgg aaaacgttct cggggcgaaa actctcaag gatcttaccg   1560 ctgttgagat ccagttcgat gtaacccact cgtgcaccca actgatcttc agcatctttt   1620
actttcacca gcgtttctgg gtgagcaaaa acaggaaggc aaaatgccgc aaaaaaggga   1680
ataagggcga cacggaaatg ttgaatactc atactcttcc ttttcaata ttattgaagc   1740 atttatcagg gttattgtct catgagcgga tacatatttg aatgtattta gaaaaataaa   1800
caaatagggg ttccgcgcac atttccccga aaagtgccac ctgacaaact tggtaccata   1860
actagttcgg cgcgccaatc tcgcctattc atggtgtata aaagttcaac atccaaagct   1920
agaacttttg gaaagagaaa gaatgtccga ataggggacg gcgtgccgta ttgttggagt   1980
ggactagcag aaagtgagga aggcacagga tgagtttcct cgagacacat agcttcagcg   2040
tcgtgtaggc taggcagagg tgagttttct cgagacatac cttcagcgtc gtcttcactg   2100
tcacagtcaa ctgacagtaa tcgttgatcc ggagagattc aaaattcaat ctgtttggac   2160
ctggataaga cacaagagcg acatcctgac atgaacgccg taaacagcaa atcctggttg   2220
aacacgtatc cttttggggg cctccagcta cgacgctcgc cccagctggg gcttccttac   2280
tatacacagc gcatatttca cggttgccag aaccatgggc gatcctaaaa agaaacgtaa   2340
ggtcatcgat aaggagaccg ccgctgccaa gttcgagaga cagcacatgg acagcatcga   2400
tatcgccgac cccattcgtt cgcgcacacc aagtcctgcc cgcgagcttc tgcccggacc   2460
ccaacccgat ggggttcagc cgactgcaga tcgtggggtg tctccgcctg ccggcggccc   2520
cctggatggc ttgccggctc ggcggacgat gtcccggacc cggctgccat ctcccctgc   2580 cccctcacct gcgttctcgg cgggcagctt cagtgacctg ttacgtcagt tcgatccgtc   2640 acttttaat acatcgcttt ttgattcatt gcctcccttc ggcgctcacc atacagaggc   2700
tgccacaggc gagtgggatg aggtgcaatc gggtctgcgg gcagccgacg ccccccacc   2760 caccatgcgc gtggctgtca ctgccgcgcg gccccgcgc gccaagccgg cgccgcgacg   2820
acgtgctgcg caaccctccg acgcttcgcc ggcggcgcag gtggatctac gcacgctcgg   2880
ctacagccag cagcaacagg agaagatcaa accgaaggtt cgttcgacag tggcgcagca   2940
ccacgaggca ctggtcggcc acgggtttac acacgcgcac atcgttgcgt taagccaaca   3000
```

```
cccggcagcg ttagggaccg tcgctgtcaa gtatcaggac atgatcgcag cgttgccaga    3060
ggcgacacac gaagcgatcg ttggcgtcgg caaacagtgg tccggcgcac gcgctctgga    3120
ggccttgctc acggtggcgg gagagttgag aggtccaccg ttacagttgg acacaggcca    3180
acttctcaag attgcaaaac gtggcggcgt gaccgcagtg gaggcagtgc atgcatggcg    3240
caatgcactg acgggtgccc cgctcaactt gaccccccag caggtggtgg ccatcgccag    3300
caataatggt ggcaagcagg cgctggagac ggtccagcgg ctgttgccgg tgctgtgcca    3360
ggcccacggc ttgaccccccc agcaggtggt ggccatcgcc agcaataatg gtggcaagca    3420
ggcgctggag acggtccagc ggctgttgcc ggtgctgtgc caggcccacg gcttgacccc    3480
ggagcaggtg gtggccatcg ccagccacga tggcggcaag caggcgctgg agacggtcca    3540
gcggctgttg ccggtgctgt gccaggccca cggcttgacc cccagcagg tggtggccat    3600 cgccagcaat ggcggtggca agcaggcgct ggagacggtc agcggctgt tgccggtgct    3660 gtgccaggcc cacggcttga ccccggagca ggtggtggcc atcgccagca atattggtgg    3720
caagcaggcg ctggagacgg tgcaggcgct gttgccggtg ctgtgccagg cccacggctt    3780
gaccccggag caggtggtgg ccatcgccag caatattggt ggcaagcagg cgctggagac    3840
ggtgcaggcg ctgttgccgg tgctgtgcca ggcccacggc ttgaccccccc agcaggtggt    3900 ggccatcgcc agcaataatg gtggcaagca ggcgctggag acggtccagc ggctgttgcc    3960
ggtgctgtgc caggcccacg gcttgacccc cagcaggtg gtggccatcg ccagcaataa    4020
tggtggcaag caggcgctgg agacggtcca gcggctgttg ccggtgctgt gccaggccca    4080
cggcttgacc ccccagcagg tggtggccat cgccagcaat aatggtggca agcaggcgct    4140
ggagacggtc agcggctgt tgccggtgct gtgccaggcc cacggcttga ccccccagca    4200
ggtggtggcc atcgccagca atggcggtgg caagcaggcg ctggagacgg tccagcggct    4260
gttgccggtg ctgtgccagg cccacggctt gaccccggag caggtggtgg ccatcgccag    4320
caatattggt ggcaagcagg cgctggagac ggtgcaggcg ctgttgccgg tgctgtgcca    4380
ggcccacggc ttgaccccccc agcaggtggt ggccatcgcc agcaataatg gtggcaagca    4440
ggcgctggag acggtccagc ggctgttgcc ggtgctgtgc caggcccacg gcttgacccc    4500
ggagcaggtg gtggccatcg ccagccacga tggcggcaag caggcgctgg agacggtcca    4560
gcggctgttg ccggtgctgt gccaggccca cggcttgacc ccggagcagg tggtggccat    4620
cgccagcaat attggtggca agcaggcgct ggagacggtc agcggctgt tgccggtgct    4680 gtgccaggcc cacggcttga ccccggagca ggtggtggcc atcgccagcc acgatggcgg    4740
caagcaggcg ctggagacgg tccagcggct gttgccggtg ctgtgccagg cccacggctt    4800 gaccccctcag caggtggtgg ccatcgccag caatggcggc ggcaggccgg cgctggagag    4860
cattgttgcc cagttatctc gccctgatcc ggcgttggcc gcgttgacca acgaccacct    4920
cgtcgccttg gcctgcctcg gcgggcgtcc tgcgctggat gcagtgaaaa agggattggg    4980
ggatcctatc agccgttccc agctggtgaa gtccgagctg gaggagaaga atccgagtt    5040 gaggcacaag ctgaagtacg tgccccacga gtacatcgag ctgatcgaga tcgcccggaa    5100
cagcacccag gaccgtatcc tggagatgaa ggtgatggag ttcttcatga aggtgtacgg    5160
ctacaggggc aagcacctgg gcggctccag gaagcccgac ggcgccatct acaccgtggg    5220
ctcccccatc gactacggcg tgatcgtgga caccaaggcc tactccggcg gctacaacct    5280
gcccatcggc caggccgacg aaatgcagag gtacgtggag gagaaccaga ccaggaacaa    5340
gcacatcaac cccaacgagt ggtggaaggt gtaccccctcc agcgtgaccg agttcaagtt    5400
```

```
cctgttcgtg tccggccact tcaagggcaa ctacaaggcc cagctgacca ggctgaacca   5460
catcaccaac tgcaacggcg ccgtgctgtc cgtggaggag ctcctgatcg gcggcgagat   5520
gatcaaggcc ggcaccctga ccctggagga ggtgaggagg aagttcaaca acggcgagat   5580
caacttcgcg gccgactgat aactcgagcg atcctctaga cgagctcctc gagcctgcag   5640
cagctgaagc tttaagatcc aatggcaagg accaagtgct ggaacttgtt ttgctttagc   5700
agatctagat cgagctacct cgactttggc tgggacactt tcagtgagga caagaagctt   5760
cagaagcgtg ctatcgaact caaccaggga cgtgcggcac aaatgggcat ccttgctctc   5820
atggtgcacg aacagttggg agtctctatc cttccttaaa aatttaattt tcattagttg   5880
cagtcactcc gctttggttt cacagtcagg aataacacta gctcgtcttc atatcctgca   5940
```

<210> SEQ ID NO 51
<211> LENGTH: 50
<212> TYPE: DNA
<213> ORGANISM: artificial sequence
<220> FEATURE:
<223> OTHER INFORMATION: Delta12 desaturase target

<400> SEQUENCE: 51

```
tagctcccaa gagtgccacc agctctactg gcagtgctac ccttagccaa             50
```

<210> SEQ ID NO 52
<211> LENGTH: 61
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (31)..(32)
<223> OTHER INFORMATION: Deep seq Delta12 desaturase_For ; n is a or c
      or t or g
<220> FEATURE:
<221> NAME/KEY: misc_feature
<222> LOCATION: (33)..(40)
<223> OTHER INFORMATION: n is a, c, g, or t

<400> SEQUENCE: 52

```
ccatctcatc cctgcgtgtc tccgactcag nnnnnnnnnn ctcgtcggtg gtccgtattg   60
g                                                                  61
```

<210> SEQ ID NO 53
<211> LENGTH: 50
<212> TYPE: DNA
<213> ORGANISM: Artificial Sequence
<220> FEATURE:
<223> OTHER INFORMATION: Deep seqDelta12 desaturase_Rev

<400> SEQUENCE: 53

```
cctatcccct gtgtgccttg gcagtctcag tggcgagatc gcgcatcagg             50
```

<210> SEQ ID NO 54
<211> LENGTH: 389
<212> TYPE: DNA
<213> ORGANISM: Phaeodactylum tricornutum

<400> SEQUENCE: 54

```
ctgtgcgtcg gttgaatcgg aatcgctaac tcgcgttttc gatgacgacg acggccagtc   60
tacttattct ttgtgctact gtaggatctc tctgcatgtt ctctcactgt gaatttgcgt  120
tccttcaggc aaaatggaag ccggaggctg tgctccatcg gctattgcgg gtgattccgg  180
```

```
aatgattttg gaagactcta ttgcgcccgt ccccagctgg acaagaccgc ggagctggat      240
attgcaccca acgccaccct tcttgccgag acgtagttc  tcaaactcaa tggtggactc      300
ggcacgggta tgggtcgtgg acaaggccga agtccctcgt tgccagtcaa ggggacgga       360 cacctttgg  tattgtaccg ccaacaagt                                        389

<210> SEQ ID NO 55
<211> LENGTH: 421
<212> TYPE: DNA
<213> ORGANISM: Phaeodactylum tricornutum

<400> SEQUENCE: 55
ctgtgcgtcg gttgaatcgg aatcgctaac tcgcgttttc gatgacgacg acggccagtc       60
tacttattct ttgtgctact gtaggatctc tctgcatgtt ctctcactgt gaatttgcgt      120
tccttcaggc aaaaatggaa gccggaggct gtgctccatc ggcgattgcc gccttcgagt      180
cgacctatgg tagtctcgtc tcgggtgatt ccggaatgat tttggaagac tctattgcgc      240
ccgtccccca gctggacaag accgcggagc tggatattgc acccaacgcc acccttcttg      300
ccgagacggt agttctcaaa ctcaatggtg gactcggcac gggtatgggt ctggacaagg      360
ccaagtccct gttgccagtc aaggggacg  acaccttttt ggatttgacc gccaaacaag      420
t                                                                     421

<210> SEQ ID NO 56
<211> LENGTH: 397
<212> TYPE: DNA
<213> ORGANISM: Phaeodactylum tricornutum

<400> SEQUENCE: 56
tatcactcag aagcgcatcc gttggttccc attggcggct gcctactcta cggactcttg       60
atggtggcgg gacaggccta ctttcgcaca cgcgaaccac tccgggcgcg gacctccctc      120
gcggcctgga atctctttct ggccctcttt tccctcgtcg gcttgtacac aacctcgcga      180
cgctcacgct ccgggaaatc tctgcgccaa tccgcaagcc acctacggat ccggatccac      240
cggattgtgg gtacaactct ttattctgtc caaatttccc gtacgtttct ttttgccaga      300
catgtgtggg gcggtggtgg actcacatat atacatacac acacacacag atactgacac      360
ttgctggcct ttataccct  ttccagtgaa ctcattg                               397

<210> SEQ ID NO 57
<211> LENGTH: 419
<212> TYPE: DNA
<213> ORGANISM: Phaeodactylum tricornutum

<400> SEQUENCE: 57
tatcactcag aagcgcatcc gttggttccc attggcggct gcctactcta cggactcttg       60
atggtggcgg gacaggccta ctttcgcaca cgcgaaccac tccgggcgcg gacctccctc      120
gcggcctgga atctctttct ggccctcttt tccctcgtcg gcatgctccg gaccttccc       180 cagcttgtac acaacctcgc gacgctcacg ctccgggaaa tctctgcgc  caatccgcaa      240 gccacctacg gatccggatc caccggattg tgggtacaac tctttattct gtccaaattc      300
ccgtacgttt cttttgcca  gacatgtgtg gggcggtggt ggactcacat atatacatac      360
acacacacac agatactgac acttgctggc ctttataccc ctttccagtg aactcattg       419

<210> SEQ ID NO 58
```

```
<211> LENGTH: 404
<212> TYPE: DNA
<213> ORGANISM: Phaeodactylum tricornutum

<400> SEQUENCE: 58
tgtactactc tctgctactg ctcatccgca ccctcacatc ttgccctcat cgctcgaaaa      60
tcttcgtcgt cccgacattg ccatcgtcca gaagcctcac actcaccgca ctcgcaaaaa     120
gaccatggac tcaaatcctc aaaatagttc tgaccaactc gataaagcgg taactgggga     180
agtgccattg cgaccctagt tggtcgcaac tgcgagcgct tgcccttttt cgaatcgcag     240
gtcaacatgt gggtctttga ggaaatggtt gaattggaag atggttccca aagaagctc      300 accgaaatca tcaactctcg ccacgaaaac gttaagtacc tcccaggcat tcccctccct     360
tccaacgttg ttgcgactcc tgatctagca gaagcctgtc gcga                      404

<210> SEQ ID NO 59
<211> LENGTH: 420
<212> TYPE: DNA
<213> ORGANISM: Phaeodactylum tricornutum

<400> SEQUENCE: 59
tgtactactc tctgctactg ctcatccgca ccctcacatc ttgccctcat cgctcgaaaa      60
tcttcgtcgt cccgacattg ccatcgtcca gaagcctcac actcaccgca ctcgcaaaaa     120
gaccatggac tcaaatcctc aaaatagttc tgaccaactc gataaagtat gcatcatcgg     180
tagcggtaac tggggaagtg ccattgcgac cctagttggt cgcaactgcg agcgcttgcc     240 cttttcgaa tcgcaggtca acatgtgggt ctttgaggaa atggttgaat tggaagatgg     300
ttcccaaaag aagctcaccg aaatcatcaa ctctcgccac gaaaacgtta agtacctccc     360
aggcattccc ctcccttcca acgttgttgc gactcctgat ctagcagaag cctgtcgcga     420

<210> SEQ ID NO 60
<211> LENGTH: 288
<212> TYPE: DNA
<213> ORGANISM: Phaeodactylum tricornutum

<400> SEQUENCE: 60
tgcgtgtgcg gcgtgtgctc acctgttgtc ctaagctgcg agcctacagt tgccaatgaa      60
accaaacctt gtgccgtttt ttatcatcga caagccatta caaaagacta acgagttaga     120
gctttgaaga cgacacaatg aagcttcata tcgcaccacc tcttattatc tcggcctacg     180
tgttttctgt atccatttc cacaacactg ttaaatgacg aaatccatcc tcgacgggat     240
tggactcacg acgagccgcc caagttgagc gaagtgaagc gcatgctt                  288

<210> SEQ ID NO 61
<211> LENGTH: 412
<212> TYPE: DNA
<213> ORGANISM: Phaeodactylum tricornutum

<400> SEQUENCE: 61
tgcgtgtgcg gcgtgtgctc acctgttgtc ctaagctgcg agcctacagt tgccaatgaa      60
accaaacctt gtgccgtttt ttatcatcga caagccatta caaaagctaa cgagttagag     120
ctttgaagac gacacaatga agcttcatat cgcaccacct cttattatct cggcctacgt     180
gttttctgta tccatttcc acaacactgt taatgccttt tcgttgcgca taccgagtac     240
ccacaggact gttttccttc cgcaagtgac gttgaatgcc aaaagatgga tggtagcaac     300
gggggtagaa acaaacgctg ctgtggcaac tccagaaaat gacgaaatcc atcctcgacg     360
```

```
ggattggact cacgacgagc cgcccaagtt gagcgaagtg aagcgcatgc tt        412
```

<210> SEQ ID NO 62
<211> LENGTH: 327
<212> TYPE: DNA
<213> ORGANISM: Phaeodactylum tricornutum

<400> SEQUENCE: 62

```
tcgtcgctcg gaagaacagt cgcacctggt gcaagtaaga aatgcccgta gggcctctct    60
cgacatatca accacgaagc gccgtattca aggaggtaag gttggctctg aaaacaagca   120
attgccggtg gtctttgccg ctttaattct ggcatgcaac acgttgcgca gctggcctcc   180
gaatggctca gtgaggactt tggtccggac agatcgaatg tgtatagcgt atgcgttccg   240
accggtgcga ctcaagcaga agataccaag aacggttact tctgagcatg gatgcttcgg   300
tggaagtctt tgcggaaggt gttaggg                                       327
```

<210> SEQ ID NO 63
<211> LENGTH: 347
<212> TYPE: DNA
<213> ORGANISM: Phaeodactylum tricornutum

<400> SEQUENCE: 63

```
tcgtcgctcg gaagaacagt cgcacctggt gcaagtaaga aattcccgta gtgcctctct    60
cgacatatca accacgaagc gccgtattca aggaggtaag gttggctctg aaaacaagca   120
attgccggtg gtctttgccc atgggatggg agattcgtgc tttaattctg gcatgcaaca   180
cgttgcgcag ctggcctccg aatggctcag tgaggacttt ggtccggaca gatcgaatgt   240
gtatagcgta tgcgttccga ccggtgcgac tcaagcagaa gataccaaga acggttactt   300
tctgagcatg gatgcttcgg tggaagtctt tgcggaaggt gttaggg                 347
```

<210> SEQ ID NO 64
<211> LENGTH: 455
<212> TYPE: DNA
<213> ORGANISM: Phaeodactylum tricornutum

<400> SEQUENCE: 64

```
tgtatcacag ggactgtttc gctacggtac atcttatcgt ttgcacagag ataccagaac    60
tccgtctcat cgtctaccgt tgttgtcttt tagatgtcgg tcgtggttcg ttttctacca   120
gtcaggctgt cggattcagt tctgcttcaa caagaagtcg gaccgaactg cacatggcag   180
cgcaggtcga cctcaaaggc aaggtagcct tgtggctgg gttgccgat tccactggtt    240
acggcaagca ggagccacaa tcattgtcgg aacgtggcct ccggtactca agatcttcca   300
aatgggtttg aaaagggac agttcaacga ggactccaca ctcgcggatg ttccctaat    360
gacgatcgaa aaggtgtatc ccctcgatgc cgtctttgat gccccagacg acgtcccgga   420
tgagattaag gaaaataagc gttacgctgg attgg                              455
```

<210> SEQ ID NO 65
<211> LENGTH: 480
<212> TYPE: DNA
<213> ORGANISM: Phaeodactylum tricornutum

<400> SEQUENCE: 65

```
tgtatcacag ggactgtttc gctacggtac atcttatcgt ttgcactgag ataccagagt    60
atcgtctcat cgtctaccgt tgttgtcttt tagatgtcgg tcgtggttcg ttttctacca   120
```

-continued

```
gtcaggctgt cggattcagt tctgcttcaa caagaagtcg gaccgaactg cacatggcag    180
cgcaggtcga cctcaaaggc aaggtagcct ttgtggctgg tgttgccgat tccactggtt    240
acggctgggc gatcgccaaa gctttggccg aagcaggagc cacaatcatt gtcggaacgt    300
ggcctccggt actcaagatc ttccaaatgg gtttgaaaaa gggacagttc aacgaggact    360
ccacactcgc ggatggttcc ctaatgacga tcgaaaaggt gtatccctc gatgccgtct    420 ttgatgcccc agacgacgtc ccggatgaga ttaaggaaaa taagcgttac gctggattgg    480
```